United States Patent
Kurata et al.

(10) Patent No.: US 7,785,795 B2
(45) Date of Patent: Aug. 31, 2010

(54) METHOD OF ASSAYING NUCLEIC ACID USING LABELED NUCLEOTIDE

(75) Inventors: Shinya Kurata, Tokyo (JP); Kyoko Takatsu, Tokyo (JP); Kazunori Nakamura, Ibaraki (JP); Takahiro Kanagawa, Ibaraki (JP)

(73) Assignees: Kankyo Engineering Co., Ltd., Tokyo (JP); National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 12/421,983

(22) Filed: Apr. 10, 2009

(65) Prior Publication Data

US 2009/0233308 A1    Sep. 17, 2009

Related U.S. Application Data

(62) Division of application No. 10/514,558, filed as application No. PCT/JP03/06896 on May 30, 2003, now abandoned.

(30) Foreign Application Priority Data

May 31, 2002    (JP)    ............... 2002-160659

(51) Int. Cl.
    C12Q 1/68    (2006.01)
    C12P 19/34   (2006.01)
(52) U.S. Cl. ............... 435/6; 435/91.1; 435/91.2
(58) Field of Classification Search ............. 435/6, 435/91.1, 91.2
    See application file for complete search history.

(56) References Cited

U.S. PATENT DOCUMENTS 6,316,230 B1 * 11/2001 Egholm et al. ............. 435/91.1
7,118,871 B2 * 10/2006 Lawler ....................... 435/6

OTHER PUBLICATIONS

Morrison, L. (1995) Detection of Energy transfer and fluorescence quenching in Non isotopic probing blotting and sequencing (second edition) p. 429-471.*
U.S. Appl. No. 12/540,390, filed Aug. 13, 2009, Nakamura et al.

* cited by examiner

*Primary Examiner*—Kenneth R. Horlick
(74) *Attorney, Agent, or Firm*—Oblon, Spivak, McClelland, Maier & Neustadt, L.L.P.

(57) ABSTRACT

A novel method is provided to assay at least one nucleic acid. According to this method, a nucleic acid polymerization reaction is conducted in a nucleic acid polymerization reaction system, which contains (A) the at least one nucleic acid as a template, (B) at least one nucleotide monomer labeled with at least one label selected from the group consisting of (a) fluorescent dyes, (b) quenchers and (c) immune related substances with a fluorescent dye or quencher contained therein, and (C) at least one nucleic acid-synthesizing enzyme. The template nucleic acid or a nucleic acid, which has been synthesized using the template nucleic acid as a template, is then assayed from a change or an amount of a change in an optical character of the nucleic acid polymerization system. This method makes it possible to specifically and accurately assay at least one nucleic acid, which is contained in a single system and can be an unknown nucleic acid and/or a known nucleic acid, with excellent sensitivity, in short time and with ease.

12 Claims, 34 Drawing Sheets

SEQUENCE LISTING

```
<160> NUMBER OF SEQ ID NOS: 36

<210> SEQ ID NO 1
<211> LENGTH: 22
<212> TYPE: DNA
<213> ORGANISM: Artificial
<220> FEATURE:
<223> OTHER INFORMATION: Synthetic DNA

<400> SEQUENCE: 1
cagactcgac agtgtagacc cg                                              22

<210> SEQ ID NO 2
<211> LENGTH: 20
<212> TYPE: DNA
<213> ORGANISM: Artificial
<220> FEATURE:
<223> OTHER INFORMATION: Synthetic DNA

<400> SEQUENCE: 2
agagtttgat cctggctcag                                                 20

<210> SEQ ID NO 3
<211> LENGTH: 18
<212> TYPE: DNA
<213> ORGANISM: Artificial
<220> FEATURE:
<223> OTHER INFORMATION: Synthetic DNA

<400> SEQUENCE: 3
ttgcatgtgt taggcctg                                                   18

<210> SEQ ID NO 4
<211> LENGTH: 38
<212> TYPE: DNA
<213> ORGANISM: Artificial
<220> FEATURE:
<223> OTHER INFORMATION: Synthetic DNA

<400> SEQUENCE: 4
acacacacac acacttcggg tctacactgt cgagtctg                             38

<210> SEQ ID NO 5
```

```
<211> LENGTH: 52
<212> TYPE: DNA
<213> ORGANISM: Artificial
<220> FEATURE:
<223> OTHER INFORMATION: Synthetic DNA

<400> SEQUENCE: 5
tatctatcta tctatctatc tatctatctt cgggtctaca ctgtcgagtc tg          52

<210> SEQ ID NO 6
<211> LENGTH: 66
<212> TYPE: DNA
<213> ORGANISM: Artificial
<220> FEATURE:
<223> OTHER INFORMATION: Synthetic DNA

<400> SEQUENCE: 6
ttattcttat tcttattctt attcttattc ttattcttat tcttcgggtc tacactgtcg   60
agtctg                                                              66

<210> SEQ ID NO 7
<211> LENGTH: 79
<212> TYPE: DNA
<213> ORGANISM: Artificial
<220> FEATURE:
<223> OTHER INFORMATION: Synthetic DNA

<400> SEQUENCE: 7
ttatttcttt atttcttat tctttattt ctttatttct ttatttcttt atttcttcgg     60
gtctacactg tcgagtctg                                                79

<210> SEQ ID NO 8
<211> LENGTH: 86
<212> TYPE: DNA
<213> ORGANISM: Artificial
<220> FEATURE:
<223> OTHER INFORMATION: Synthetic DNA

<400> SEQUENCE: 8
ttattttctt tattttcttt attttcttta ttttctttat tttctttatt ttctttattt   60
tcttcgggtc tacactgtcg agtctg                                        86

<210> SEQ ID NO 9
<211> LENGTH: 92
<212> TYPE: DNA
<213> ORGANISM: Artificial
<220> FEATURE:
<223> OTHER INFORMATION: Synthetic DNA

<400> SEQUENCE: 9
ttatttcttt ttatttcttt tatttcttt tatttcttt tatttcttt tatttcttt       60 ttatttcttt cgggtctaca ctgtcgagtc tg                                 92

<210> SEQ ID NO 10
<211> LENGTH: 99
<212> TYPE: DNA
<213> ORGANISM: Artificial
<220> FEATURE:
<223> OTHER INFORMATION: Synthetic DNA

<400> SEQUENCE: 10
ttatttttct ttatttttc ttttatttt cttttatttt tctttatttt tcttttatt      60 tttcttttat ttttcttcgg gtctacactg tcgagtctg                          99
```

<210> SEQ ID NO 11
<211> LENGTH: 105
<212> TYPE: DNA
<213> ORGANISM: Artificial
<220> FEATURE:
<223> OTHER INFORMATION: Synthetic DNA

<400> SEQUENCE: 11
ttattttctt ttttatttt cttttatttt ttctttttat ttttctttt attttctttt    60 ttattttctt ttttatttt cttcgggtct acactgtcga gtctg    105

<210> SEQ ID NO 12
<211> LENGTH: 118
<212> TYPE: DNA
<213> ORGANISM: Artificial
<220> FEATURE:
<223> OTHER INFORMATION: Synthetic DNA

<400> SEQUENCE: 12 ttatttttc ttttttattt tttcttttt atttttctt ttttatttt tcttttttat    60 ttttctttt ttattttttc ttttttattt tttcttcggg tctacactgt cgagtctg    118

<210> SEQ ID NO 13
<211> LENGTH: 26
<212> TYPE: DNA
<213> ORGANISM: Artificial
<220> FEATURE:
<223> OTHER INFORMATION: Synthetic DNA

<400> SEQUENCE: 13
gcttcgggtc tacactgtcg agtctg    26

<210> SEQ ID NO 14
<211> LENGTH: 26
<212> TYPE: DNA
<213> ORGANISM: Artificial
<220> FEATURE:
<223> OTHER INFORMATION: Synthetic DNA

<400> SEQUENCE: 14
gctccgggtc tacactgtcg agtctg    26

<210> SEQ ID NO 15
<211> LENGTH: 22
<212> TYPE: DNA
<213> ORGANISM: Artificial
<220> FEATURE:
<223> OTHER INFORMATION: Synthetic DNA

<400> SEQUENCE: 15
gtgtaaccca taacccccaa ga    22

<210> SEQ ID NO 16
<211> LENGTH: 19
<212> TYPE: DNA
<213> ORGANISM: Artificial
<220> FEATURE:
<223> OTHER INFORMATION: Synthetic DNA

<400> SEQUENCE: 16
caccagcaga ccctcaagc    19

<210> SEQ ID NO 17

```
<211> LENGTH: 23
<212> TYPE: DNA
<213> ORGANISM: Artificial
<220> FEATURE:
<223> OTHER INFORMATION: Synthetic DNA

<400> SEQUENCE: 17
cccacactca cagttttcac ttc                                              23

<210> SEQ ID NO 18
<211> LENGTH: 23
<212> TYPE: DNA
<213> ORGANISM: Artificial
<220> FEATURE:
<223> OTHER INFORMATION: Synthetic DNA

<400> SEQUENCE: 18
cccacactca cagttttcac ttt                                              23

<210> SEQ ID NO 19
<211> LENGTH: 44
<212> TYPE: DNA
<213> ORGANISM: Artificial
<220> FEATURE:
<223> OTHER INFORMATION: Synthetic DNA

<400> SEQUENCE: 19
tgttcctgat gcagtgggca gctttagtct gcggcggtgt tctg                       44

<210> SEQ ID NO 20
<211> LENGTH: 45
<212> TYPE: DNA
<213> ORGANISM: Artificial
<220> FEATURE:
<223> OTHER INFORMATION: Synthetic DNA

<400> SEQUENCE: 20
tgctgggtcg gcacagcctg aagctgacct gaaatacctg gcctg                      45

<210> SEQ ID NO 21
<211> LENGTH: 18
<212> TYPE: DNA
<213> ORGANISM: Artificial
<220> FEATURE:
<223> OTHER INFORMATION: Synthetic DNA

<400> SEQUENCE: 21
tgcttgtggc ctctcgtg                                                    18

<210> SEQ ID NO 22
<211> LENGTH: 16
<212> TYPE: DNA
<213> ORGANISM: Artificial
<220> FEATURE:
<223> OTHER INFORMATION: Synthetic DNA

<400> SEQUENCE: 22
ggggtgggaa gctgtg                                                      16

<210> SEQ ID NO 23
<211> LENGTH: 23
<212> TYPE: DNA
<213> ORGANISM: Artificial
<220> FEATURE:
<223> OTHER INFORMATION: Synthetic DNA

<400> SEQUENCE: 23
```
tgatcttgct gggtcggcac agc                                         23

<210> SEQ ID NO 24
<211> LENGTH: 23
<212> TYPE: DNA
<213> ORGANISM: Artificial
<220> FEATURE:
<223> OTHER INFORMATION: Synthetic DNA

<400> SEQUENCE: 24
tgatcttgct gggtcggcac agt                                         23

<210> SEQ ID NO 25
<211> LENGTH: 25
<212> TYPE: DNA
<213> ORGANISM: Artificial
<220> FEATURE:
<223> OTHER INFORMATION: Synthetic DNA

<400> SEQUENCE: 25
acctgatttc cttactgcct cttgc                                       25

<210> SEQ ID NO 26
<211> LENGTH: 25
<212> TYPE: DNA
<213> ORGANISM: Artificial
<220> FEATURE:
<223> OTHER INFORMATION: Synthetic DNA

<400> SEQUENCE: 26
gtcctgcttg cttacctcgc ttagt                                       25

<210> SEQ ID NO 27
<211> LENGTH: 21
<212> TYPE: DNA
<213> ORGANISM: Artificial
<220> FEATURE:
<223> OTHER INFORMATION: Synthetic DNA

<400> SEQUENCE: 27
tgtgcctgtc ctgggagaga c                                           21

<210> SEQ ID NO 28
<211> LENGTH: 45
<212> TYPE: DNA
<213> ORGANISM: Artificial
<220> FEATURE:
<223> OTHER INFORMATION: Synthetic DNA

<400> SEQUENCE: 28
ttctaatacg actcactata gggagaccct tgccaggtga ttggc                 45

<210> SEQ ID NO 29
<211> LENGTH: 40
<212> TYPE: DNA
<213> ORGANISM: Artificial
<220> FEATURE:
<223> OTHER INFORMATION: Synthetic DNA

<400> SEQUENCE: 29
gcggtcccaa aagggtcagt gtttctgtgg tcacgaagtc                       40

<210> SEQ ID NO 30
<211> LENGTH: 18
<212> TYPE: DNA

```
<213> ORGANISM: Artificial
<220> FEATURE:
<223> OTHER INFORMATION: Synthetic DNA

<400> SEQUENCE: 30
ctctaatagt gctggctc                                                       18

<210> SEQ ID NO 31
<211> LENGTH: 18
<212> TYPE: DNA
<213> ORGANISM: Artificial
<220> FEATURE:
<223> OTHER INFORMATION: Synthetic DNA

<400> SEQUENCE: 31
ctctaatagt gctggctg                                                       18

<210> SEQ ID NO 32
<211> LENGTH: 46
<212> TYPE: DNA
<213> ORGANISM: Artificial
<220> FEATURE:
<223> OTHER INFORMATION: Synthetic DNA

<400> SEQUENCE: 32
ttctaatacg actcactata gggagacctt tgtagctggg aacttc                        46

<210> SEQ ID NO 33
<211> LENGTH: 41
<212> TYPE: DNA
<213> ORGANISM: Artificial
<220> FEATURE:
<223> OTHER INFORMATION: Synthetic DNA

<400> SEQUENCE: 33
gcggtcccaa aagggtcagt accaaaacct ggtaaatacg g                             41

<210> SEQ ID NO 34
<211> LENGTH: 19
<212> TYPE: DNA
<213> ORGANISM: Artificial
<220> FEATURE:
<223> OTHER INFORMATION: Synthetic DNA

<400> SEQUENCE: 34
gagatagcag acaacgtcc                                                      19

<210> SEQ ID NO 35
<211> LENGTH: 19
<212> TYPE: DNA
<213> ORGANISM: Artificial
<220> FEATURE:
<223> OTHER INFORMATION: Synthetic DNA

<400> SEQUENCE: 35
gagatagcag acaacgtcg                                                      19

<210> SEQ ID NO 36
<211> LENGTH: 92
<212> TYPE: DNA
<213> ORGANISM: Artificial
<220> FEATURE:
<223> OTHER INFORMATION: Synthetic DNA
```

```
<400> SEQUENCE: 36
ttgttttgtt ttgttttgtt ttgttttgtt ttgttttgtt ttgttttgtt ttgttttgtt        60
ttgttttgtt cgggtctaca ctgtcgagtc tg                                      92
```

METHOD OF ASSAYING NUCLEIC ACID USING LABELED NUCLEOTIDE

TECHNICAL FIELD

This invention relates to a method of assaying plural nucleic acids, and specifically to a method of assaying at least one of unknown nucleic acids and/or a known nucleic acids (target nucleic acid) by using a nucleotide labeled with a substance such as a fluorescent dye. In the case of plural nucleic acids, they can be assayed at the same time.

BACKGROUND ART

Numerous methods are known for the assay of a target nucleic acid by using a nucleic acid probe. Many examples can be mentioned including those represented by (1) methods making use of a probe which utilizes the FRET (fluorescence resonance energy transfer) phenomenon (see, for example, Morrison et al., Anal. Biochem., 183, 231-244, 1989, and Xiangnin Chen et al., Proc. Natl. Acad. Sci. USA, 94, 10756-10761, 1977); (2) and methods making use of a probe which utilizes the characteristic of a fluorescence dye that the intensity of fluorescence emission is quenched as a result of its interaction with a particular nucleic acid base (see, for example, KURATA et al., Nucleic Acids Research, 29(6), e34, 2001). These methods measures a change or the amount of a change in an optical character (fluorescence intensity) of a fluorescence dye or the like, with which a nucleic acid probe is labeled, by hybridizing the labeled nucleic acid probe with a target nucleic acid and/or amplifying the target nucleic acid in a homogeneous system. Such a nucleic acid probe will hereinafter be called "a nucleic acid probe for a homogeneous solution system" throughout the specification. As an alternative, it may also be called simply "a nucleic acid probe" in some instances.

However, a nucleic acid probe for a homogeneous solution system, said probe being required in any one of the above-described methods, requires an oligonucleotide to be labeled with a fluorescence substance and/or a quencher substance. On top of this requirement, there is no standardized method for the designing of the probe. These circumstances have led to a waste of time and money. There is also an outstanding demand for further improvements in the assay sensitivity, although the assay sensitivity has been increasingly improved. Moreover, plural nucleic acids, which exist in a single system in the natural world and include unknown nucleic acids and/or known nucleic acids, cannot be assayed at the same time, simply and easily, specifically, accurately, in a short time, and with excellent sensitivity.

With the foregoing circumstances in view, the present invention has as an object to provide a novel method which makes it possible to assay at least one of unknown nucleic acids and/or known nucleic acids, which exist in a single system, simply and easily, specifically, accurately, in a short time, and with excellent sensitivity.

DISCLOSURE OF THE INVENTION

As a result of an extensive investigation, the present inventors have found that, when a fluorescence-labeled nucleotide or quencher-labeled nucleotide is incorporated in a nucleic acid polymer in the course of synthesis of a nucleic acid, the fluorescence character of the fluorescence dye changes significantly compared with that before the incorporation. The present invention has been completed on the basis of the above finding.

Described specifically, the present invention provides:

1) A method of assaying at least one nucleic acid, which comprises: conducting a nucleic acid polymerization reaction in a nucleic acid polymerization reaction system comprising (A) the at least one nucleic acid as a template, (B) at least one nucleotide monomer labeled with at least one label selected from the group consisting of (a) fluorescent dyes, (b) quenchers and (c) immune related substances with a fluorescent dye or quencher contained therein, and (C) at least one nucleic acid-synthesizing enzyme; and assaying the template nucleic acid or a nucleic acid, which has been synthesized using the template nucleic acid as a template, from a change or an amount of a change in an optical character of the nucleic acid polymerization system.

In the above-described method of the present invention, it is preferred:

2) that the label is a combination of at least one donor fluorescent dye and at least one acceptor fluorescent dye;

3) that the label is a combination of at least one fluorescent dye and at least one quencher;

4) that the nucleic acid polymerization system further comprises (D) at least one nucleotide monomer not labeled with any label;

5) that the nucleic acid polymerization system further comprises (E) a nucleic acid primer capable of specifically hybridizing to said template nucleic acid and comprising at least one nucleotide monomer;

6) that in the above method 5), said nucleic acid primer is labeled with (E') a label as described above in 1);

7) that in the above method 1), said nucleic acid polymerization system further comprises a non-labeled nucleotide;

8) that in the above method 7), said fluorescence-labeled and/or non-labeled nucleotide comprises guanine (g) and/or said template nucleic acid comprises at least one guanine (g);

9) that in the above method 1), said nucleic acid polymerization system further comprises a non-labeled nucleotide and a fluorescence-labeled nucleic acid primer without any ingredient (B) as described above in 1);

10) that in the above method 9), said non-labeled nucleotide comprises a guanine (g) base; and 11) that in the above method 1), 7) and/or 9), said non-labeled nucleotide and/or labeled nucleotide is a triphosphate.

The present invention also provides 12) a method of assaying a nucleic acid, which comprises: conducting a nucleic acid polymerization reaction in a nucleic acid polymerization system comprising said nucleic acid as a template, at least one dideoxynucleotide monomer labeled with at least one fluorescent dye and/or at least one quencher, and a nucleic acid-synthesizing enzyme; and assaying said template nucleic acid or a nucleic acid polymer, which has been synthesized using said template nucleic acid as a template, from a change or an amount of a change in fluorescence intensity.

It is preferred in:

13) that in the above method 12), said nucleic acid polymerization system is a system further comprising a labeled nucleotide or a non-labeled nucleotide or both of them;

14) that in the above method 12, said nucleic acid polymerization system further comprises a non-labeled nucleic acid primer;

15) that in the above method 1, 7, 9 and/or 12, said nucleic acid polymerization system further comprises (F) a fluorescent dye capable of emitting fluorescence upon binding to a nucleic acid.

The present invention further provides 16) a method of assaying a nucleic acid, which comprises: conducting a nucleic acid polymerization reaction in a nucleic acid polymerization system comprising said nucleic acid as a template, a non-labeled dideoxynucleotide monomer, a labeled nucleotide, a non-labeled nucleic acid primer, at least one fluorescent dye cable of emitting fluorescence upon binding to a nucleic acid, and a nucleic acid-synthesizing enzyme; and assaying said template nucleic acid or a nucleic acid polymer, which has been synthesized using said template nucleic acid as a template, from a change or an amount of a change in fluorescence intensity.

It is also preferred:

17) that in the above method 12) and/or 16), said non-labeled dideoxynucleotide, labeled dideoxynucleotide, non-labeled nucleotide and/or labeled nucleotide is a triphosphate; and 18) that in the above method 1), 7), 9), 12) and/or 16), said nucleic acid-synthesizing enzyme is at least one enzyme selected from DNA polymerases, RNA polymerases, reverse transcriptases, and modifications thereof.

| | |
|---|---|
| -●- | Model 1 |
| -■- | Model 2 |

-continued

| | |
|---|---|
| -♦- | Model 3 |
| -▼- | Model 4 |
| -○- | Model 5 |
| -□- | Model 6 |
| -◇- | Model 7 |
| -Δ- | Model 8 |
| — | Model 9 |
| — | Model 10 |

Figure 11:
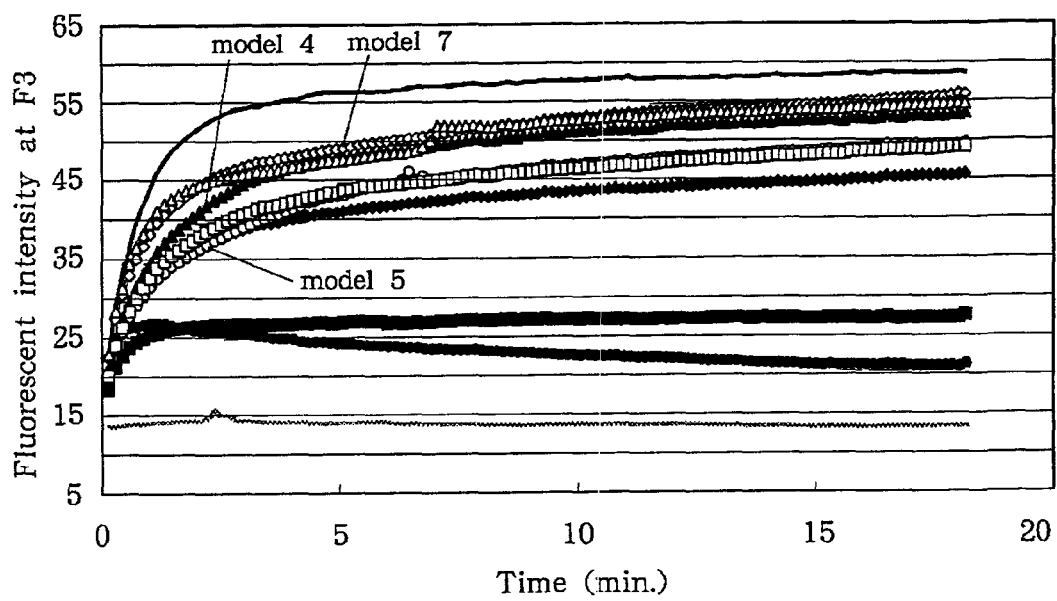

FIG. 11 illustrates an assay of a nucleic acid by making use of an interaction (FRET phenomenon) between fluorescent dye specific to a double-stranded nucleic acid (hereinafter referred to as "double-stranded-nucleic-acid-specific fluorescent dye") and a fluorescence-labeled nucleotide: changes in the fluorescence intensities at F3 of Models 1 to 10.

| | |
|---|---|
| -●- | Model 1 |
| -■- | Model 2 |
| -♦- | Model 3 |
| -▼- | Model 4 |
| -○- | Model 5 |
| -□- | Model 6 |
| -◇- | Model 7 |
| -Δ- | Model 8 |
| — | Model 9 |
| — | Model 10 |

Figure 12:
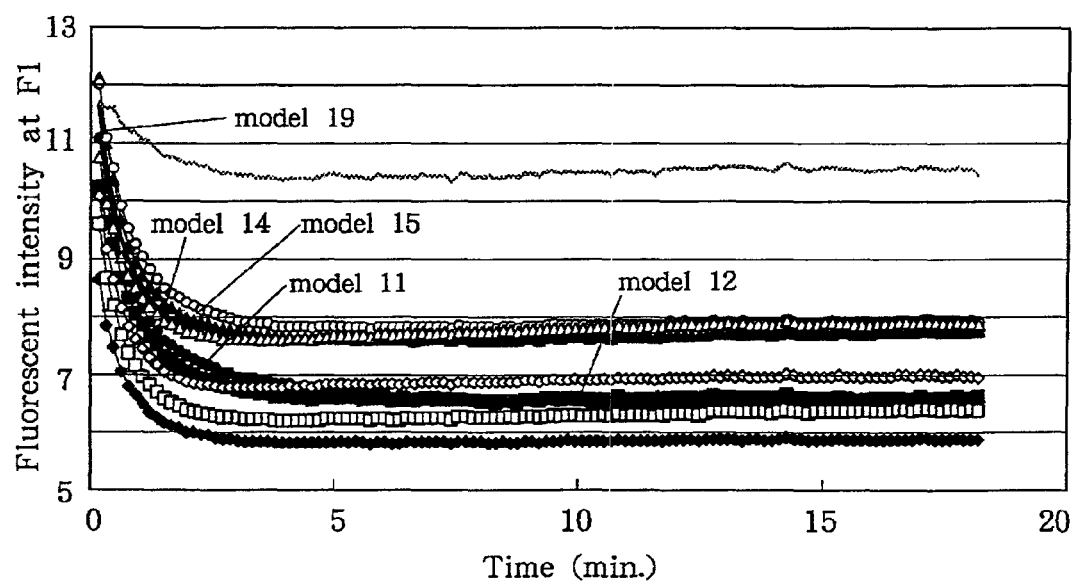

FIG. 12 illustrates an assay of a nucleic acid by making use of an interaction (FRET phenomenon) between fluorescent dye specific to a double-stranded nucleic acid (hereinafter referred to as "double-stranded-nucleic-acid-specific fluorescent dye") and a fluorescence-labeled nucleotide: changes in the fluorescence intensities at F1 of Models 11 to 20.

| | |
|---|---|
| -●- | Model 11 |
| -■- | Model 12 |
| -♦- | Model 13 |
| -▼- | Model 14 |
| -○- | Model 15 |
| -□- | Model 16 |
| -◇- | Model 17 |
| -Δ- | Model 18 |
| — | Model 19 |
| — | Model 20 |

Figure 13:
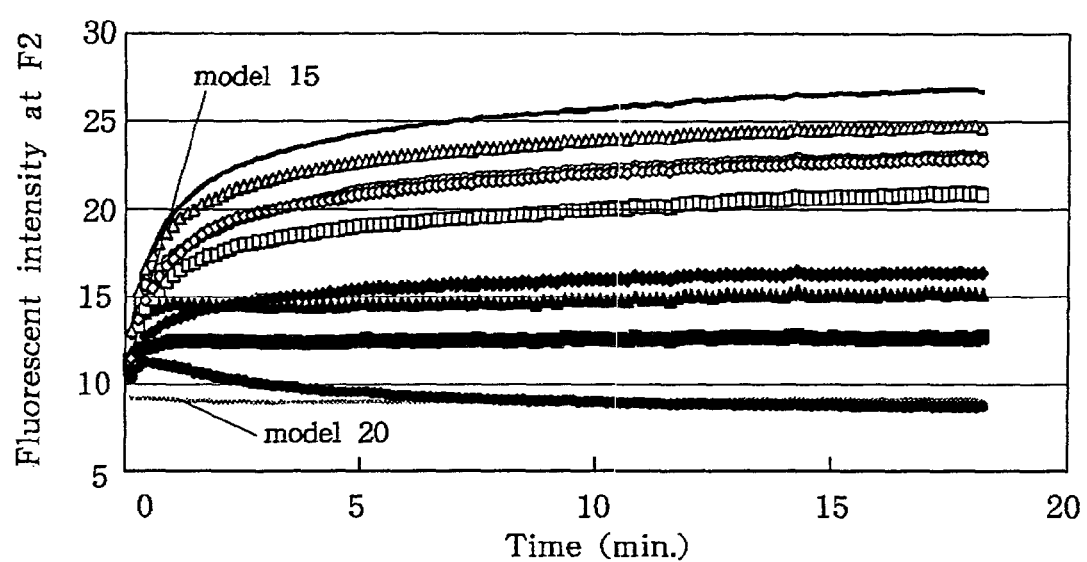

FIG. 13 illustrates an assay of a nucleic acid by making use of an interaction (FRET phenomenon) between fluorescent dye specific to a double-stranded nucleic acid (hereinafter referred to as "double-stranded-nucleic-acid-specific fluorescent dye") and a fluorescence-labeled nucleotide: changes in the fluorescence intensities at F2 of Models 11 to 20.

| | |
|---|---|
| -●- | Model 11 |
| -■- | Model 12 |
| -♦- | Model 13 |
| -▼- | Model 14 |
| -○- | Model 15 |
| -□- | Model 16 |
| -◇- | Model 17 |
| -Δ- | Model 18 |
| — | Model 19 |
| — | Model 20 |

Figure 14:
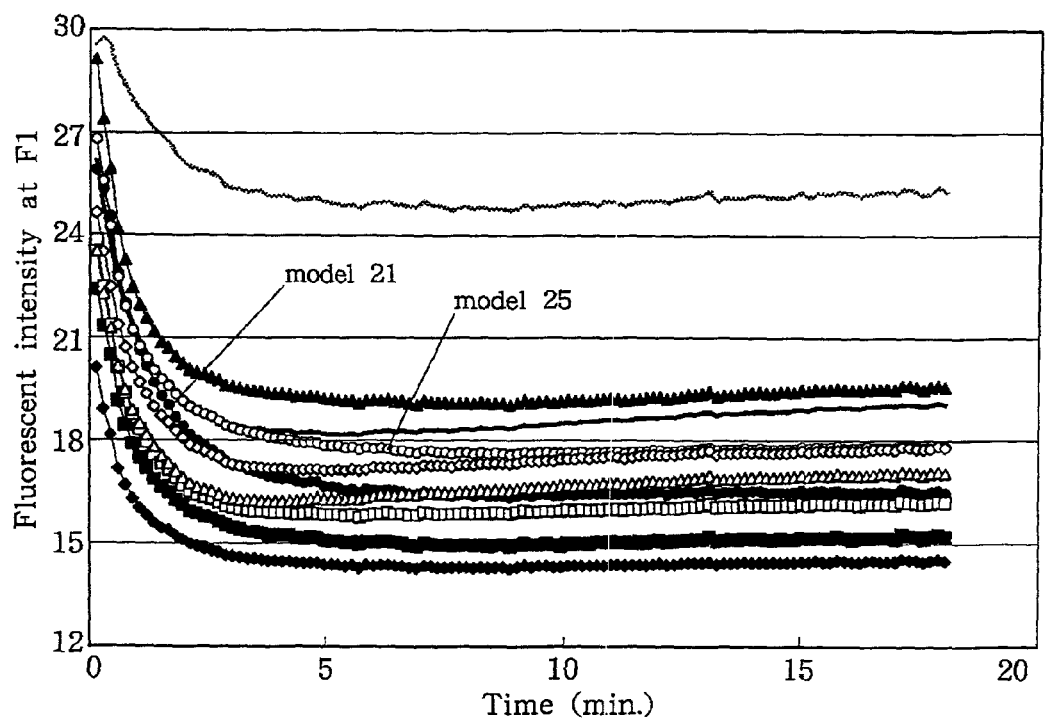

FIG. 14 illustrates an assay of a nucleic acid by making use of an interaction (FRET phenomenon) between fluorescent dye specific to a double-stranded nucleic acid (hereinafter referred to as "double-stranded-nucleic-acid-specific fluorescent dye") and a fluorescence-labeled nucleotide: changes in the fluorescence intensities at F1 of Models 21 to 30.

| | |
|---|---|
| -●- | Model 21 |
| -■- | Model 22 |
| -♦- | Model 23 |
| -▼- | Model 24 |
| -○- | Model 25 |
| -□- | Model 26 |
| -◇- | Model 27 |
| -△- | Model 28 |
| — | Model 29 |
| — | Model 30 |

Figure 15:
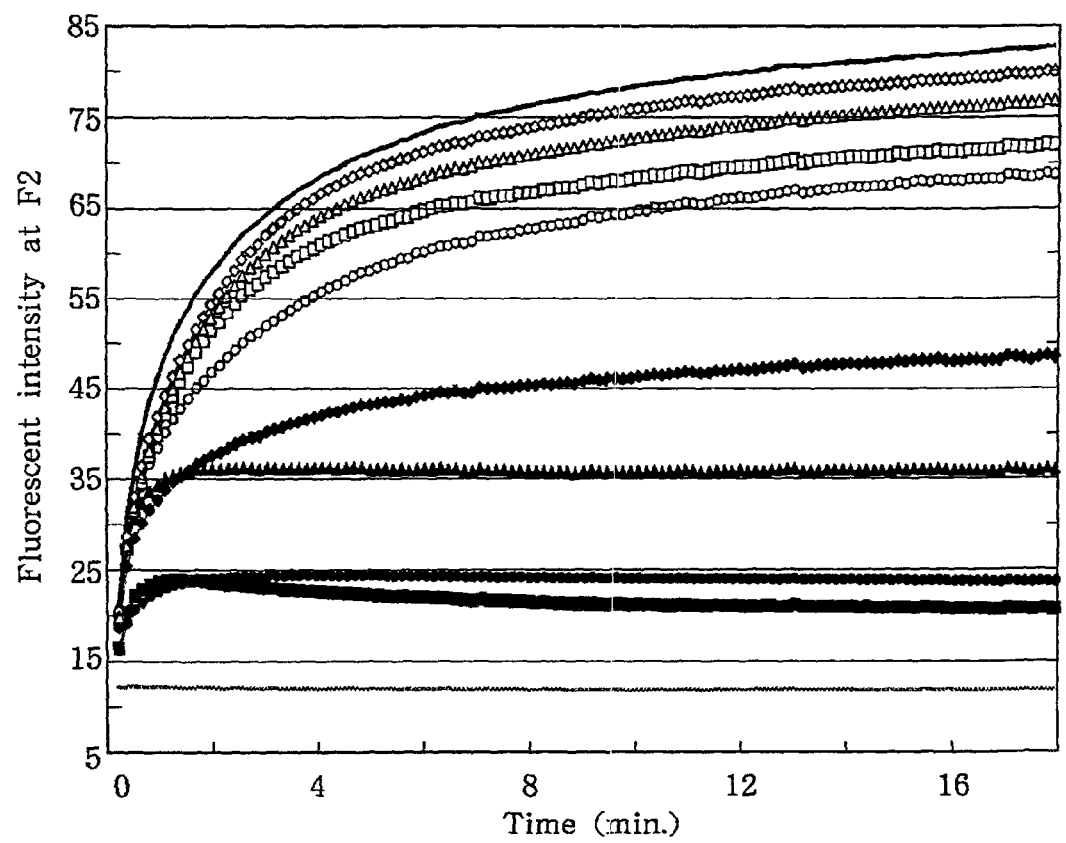

FIG. 15 illustrates an assay of a nucleic acid by making use of an interaction (FRET phenomenon) between fluorescent dye specific to a double-stranded nucleic acid (hereinafter referred to as "double-stranded-nucleic-acid-specific fluorescent dye") and a fluorescence-labeled nucleotide: changes in the fluorescence intensities at F2 of Models 21 to 30.

| | |
|---|---|
| -●- | Model 21 |
| -■- | Model 22 |
| -♦- | Model 23 |
| -▼- | Model 24 |
| -○- | Model 25 |
| -□- | Model 26 |
| -◇- | Model 27 |
| -△- | Model 28 |
| — | Model 29 |
| — | Model 30 |

Figure 16:
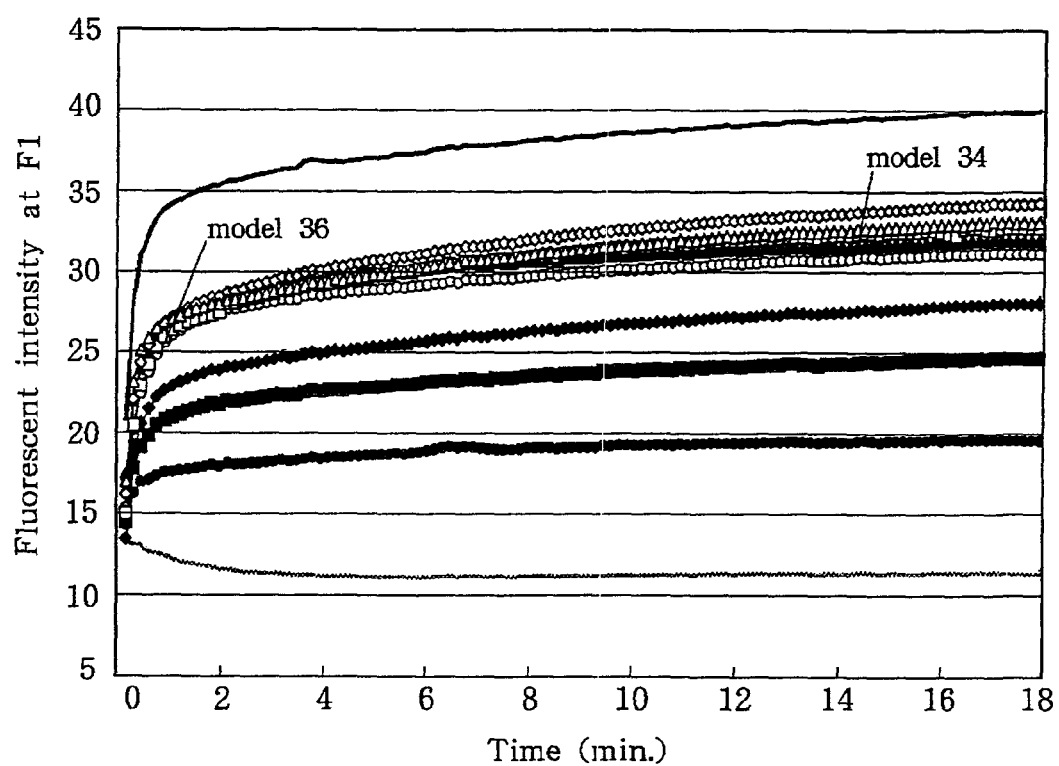

FIG. 16 illustrates an assay of a nucleic acid by making use of an interaction (FRET phenomenon) between fluorescent dye specific to a double-stranded nucleic acid (hereinafter referred to as "double-stranded-nucleic-acid-specific fluorescent dye") and a fluorescence-labeled nucleotide: changes in the fluorescence intensities at F1 of Models 31 to 40.

| | |
|---|---|
| -●- | Model 31 |
| -■- | Model 32 |
| -♦- | Model 33 |
| -▼- | Model 34 |
| -○- | Model 35 |
| -□- | Model 36 |
| -◇- | Model 37 |
| -△- | Model 38 |
| — | Model 39 |
| — | Model 40 |

Figure 17:
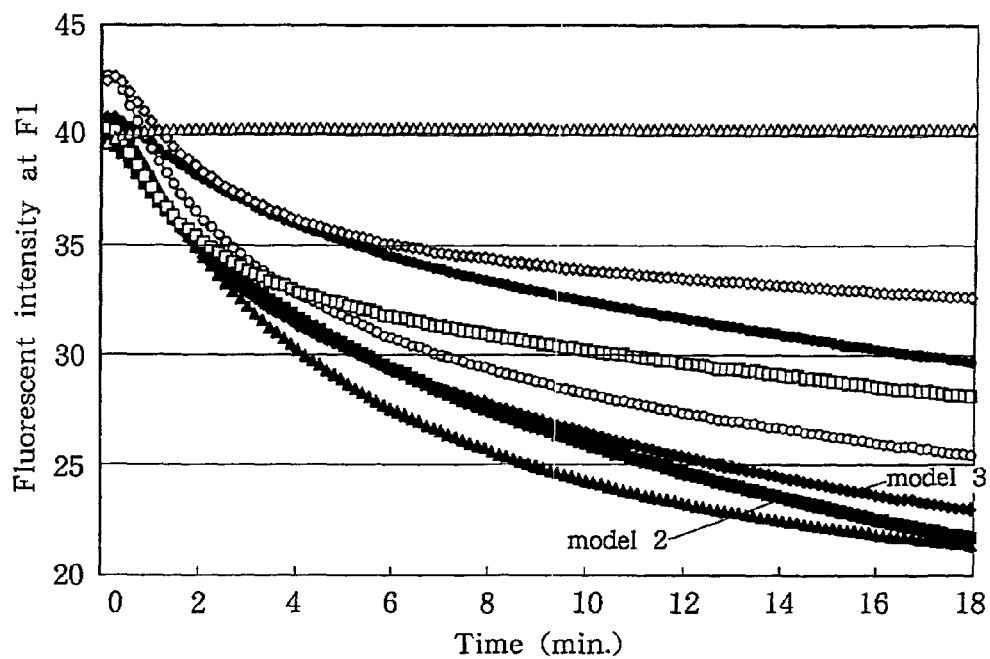

FIG. 17 illustrates an assay of a nucleic acid by making use of an interaction (FRET phenomenon) between two fluorescence-labeled nucleotides: changes in the fluorescence at F1 of Models 1 to 8.

| | |
|---|---|
| -●- | Model 1 |
| -■- | Model 2 |
| -♦- | Model 3 |
| -▼- | Model 4 |
| -○- | Model 5 |

-continued

| | |
|---|---|
| -□- | Model 6 |
| -◇- | Model 7 |
| -△- | Model 8 |

Figure 18:
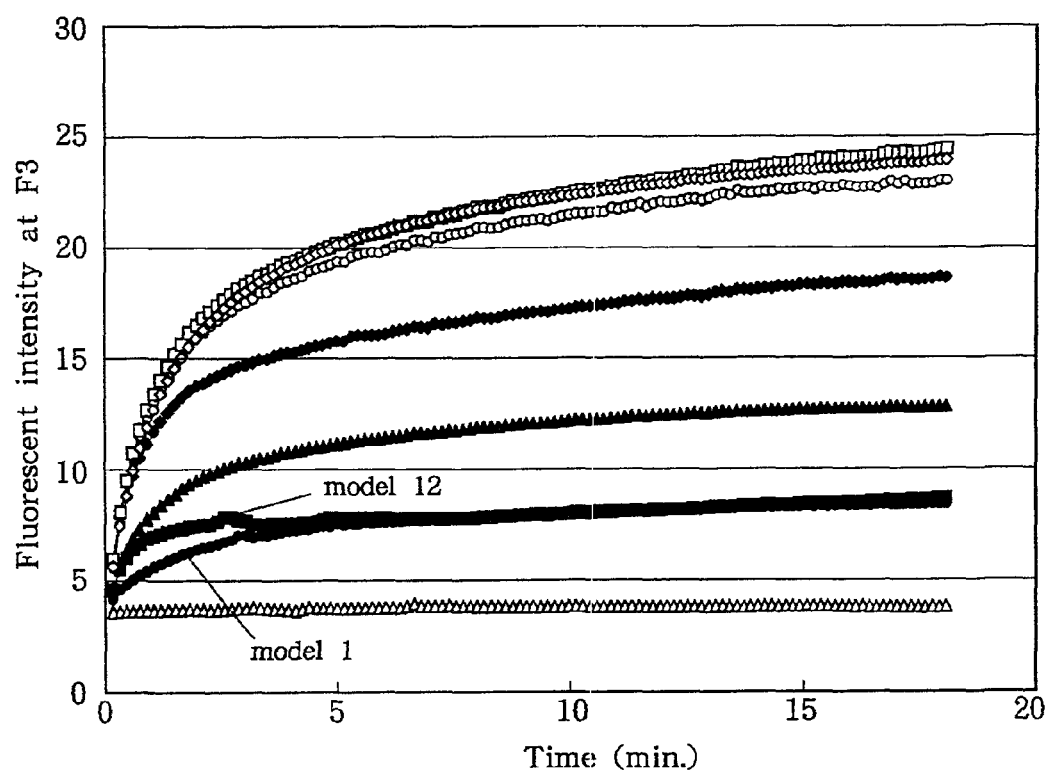

FIG. 18 illustrates an assay of a nucleic acid by making use of an interaction (FRET phenomenon) between two fluorescence-labeled nucleotides: changes in the fluorescence at F3 of Models 1 to 8.

| | |
|---|---|
| -●- | Model 1 |
| -■- | Model 2 |
| -♦- | Model 3 |
| -▼- | Model 4 |
| -○- | Model 5 |
| -□- | Model 6 |
| -◇- | Model 7 |
| -△- | Model 8 |

Figure 19:
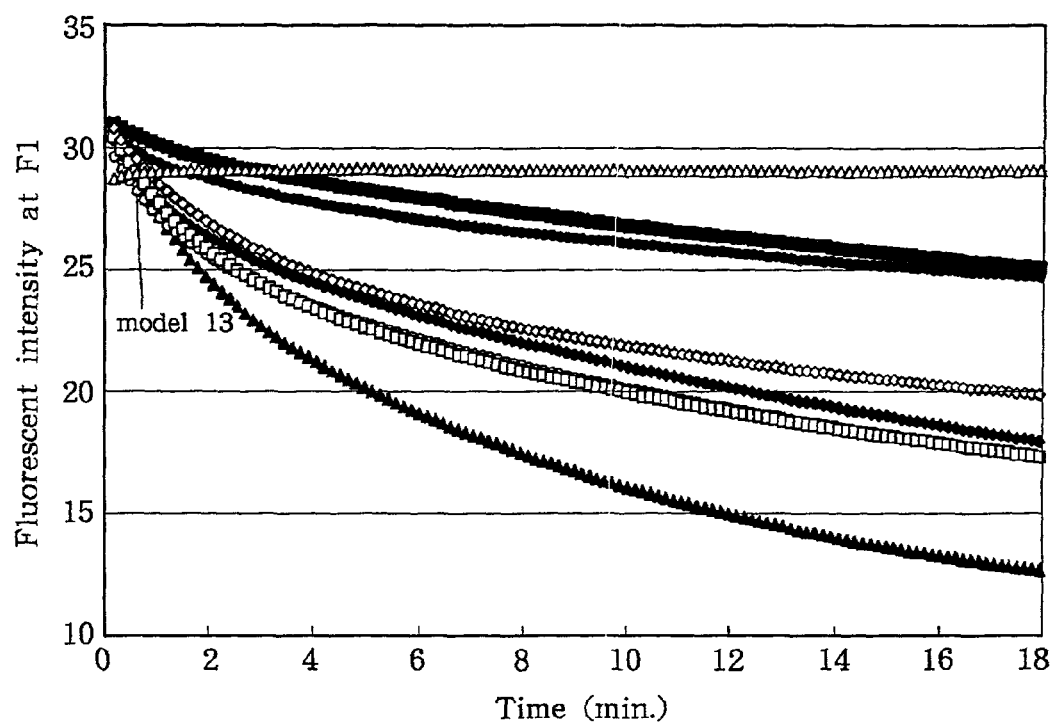

FIG. 19 illustrates an assay of a nucleic acid by making use of an interaction (FRET phenomenon) between two fluorescence-labeled nucleotides: changes in the fluorescence at F1 of Models 9 to 16.

| | |
|---|---|
| -●- | Model 9 |
| -■- | Model 10 |
| -♦- | Model 11 |
| -▼- | Model 12 |
| -○- | Model 13 |
| -□- | Model 14 |
| -◇- | Model 15 |
| -△- | Model 16 |

Figure 20:
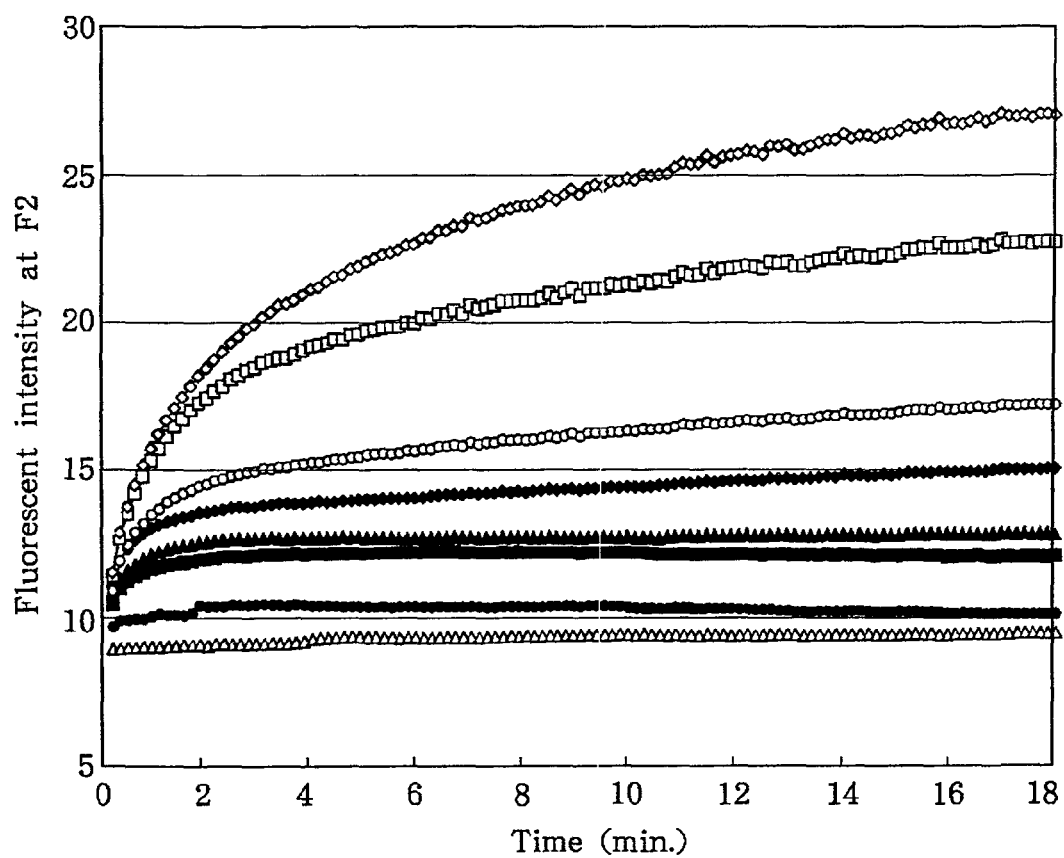

FIG. 20 illustrates an assay of a nucleic acid by making use of an interaction (FRET phenomenon) between two fluorescence-labeled nucleotides: changes in the fluorescence at F2 of Models 9 to 16.

| | |
|---|---|
| -●- | Model 9 |
| -■- | Model 10 |
| -♦- | Model 11 |
| -▼- | Model 12 |
| -○- | Model 13 |
| -□- | Model 14 |
| -◇- | Model 15 |
| -△- | Model 16 |

Figure 21:
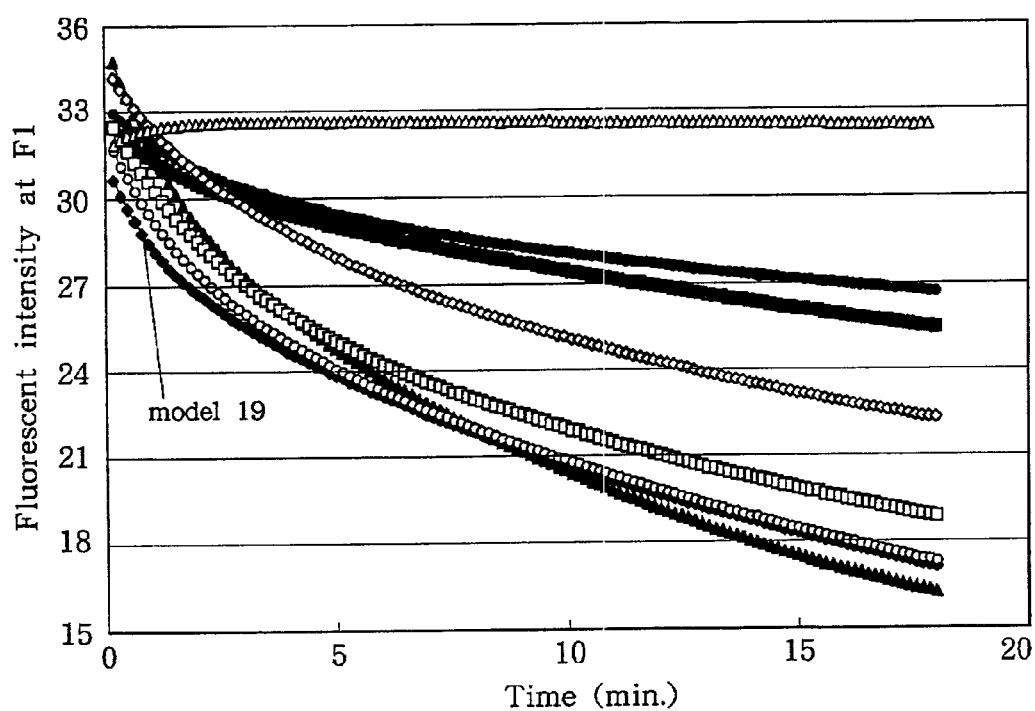

FIG. 21 illustrates an assay of a nucleic acid by making use of an interaction (FRET phenomenon) between two fluorescence-labeled nucleotides: changes in the fluorescence at F1 of Models 17 to 24.

| | |
|---|---|
| -●- | Model 17 |
| -■- | Model 18 |
| -♦- | Model 19 |
| -▼- | Model 20 |
| -○- | Model 21 |
| -□- | Model 22 |
| -◇- | Model 23 |
| -△- | Model 24 |

Figure 22:
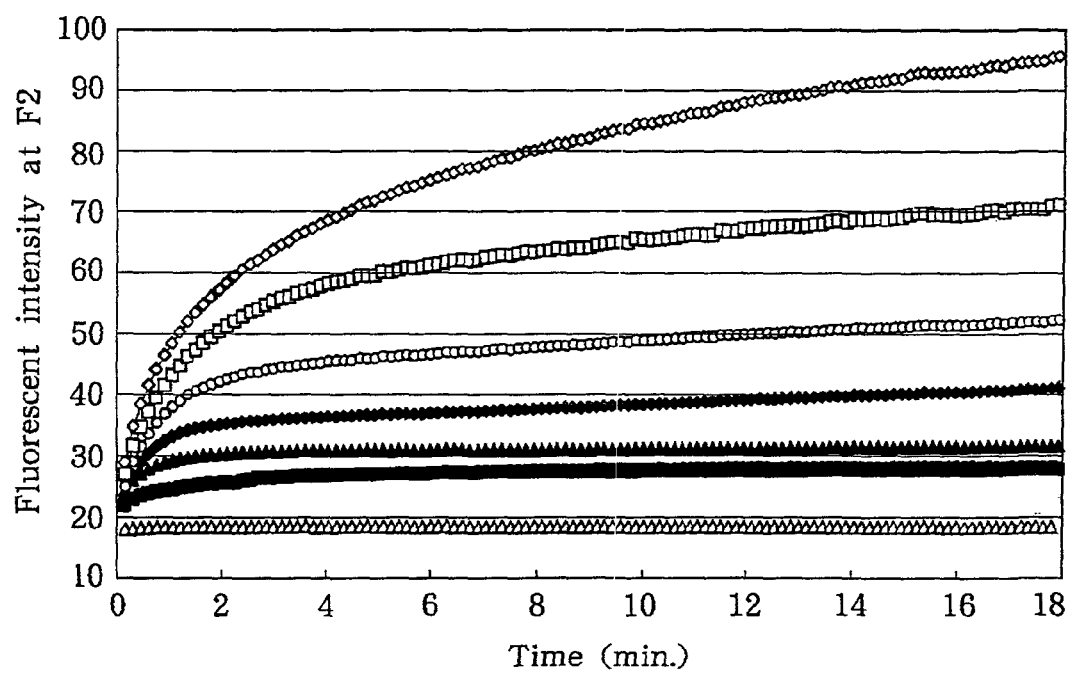

FIG. 22 illustrates an assay of a nucleic acid by making use of an interaction (FRET phenomenon) between two fluorescence-labeled nucleotides: changes in the fluorescence at F2 of Models 17 to 24.

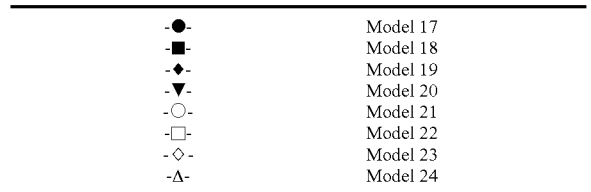

Figure 23:
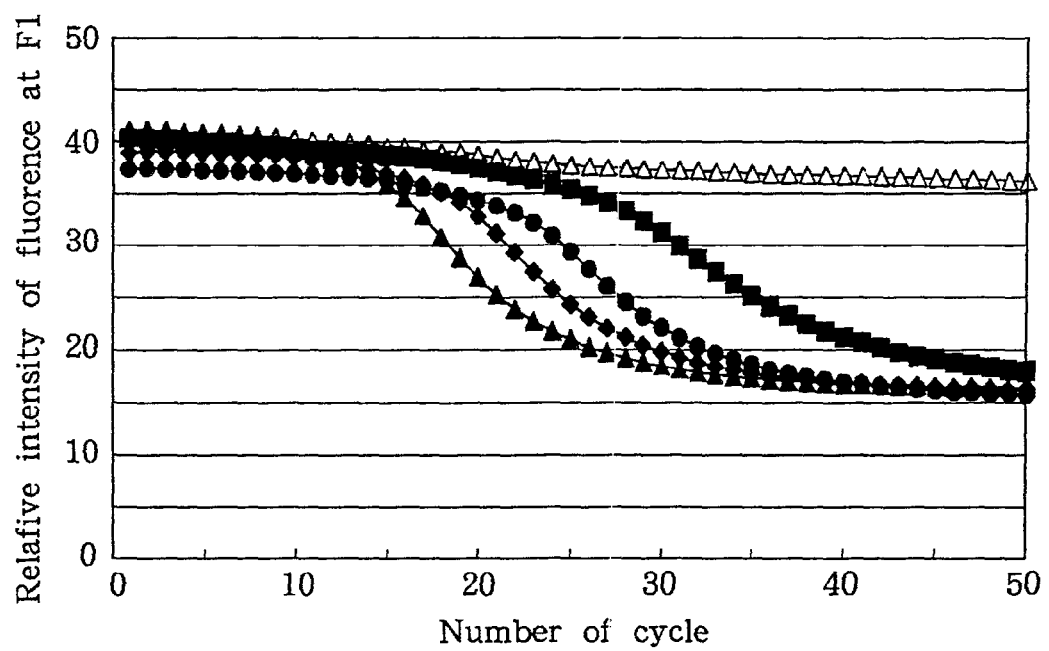

FIG. 23 illustrates real-time monitoring of PCR amplification product by making use of two fluorescence-labeled nucleotides (changes in the fluorescence at F1).

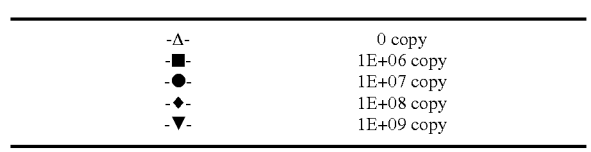

Figure 24:
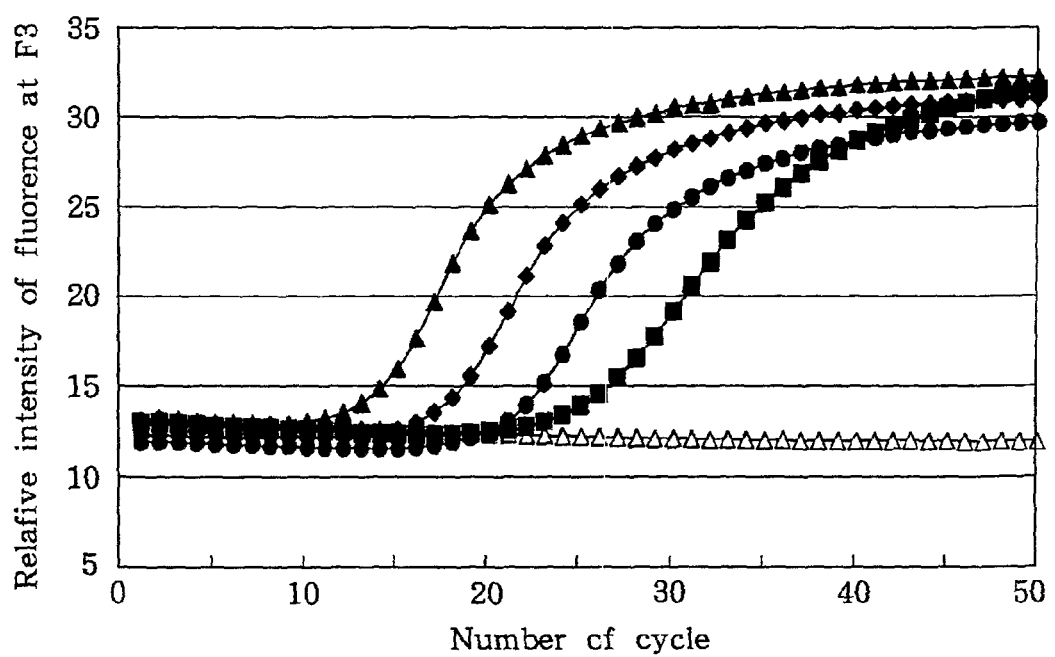

FIG. 24 illustrates real-time monitoring of PCR amplification product by making use of two fluorescence-labeled nucleotides (changes in the fluorescence at F3).

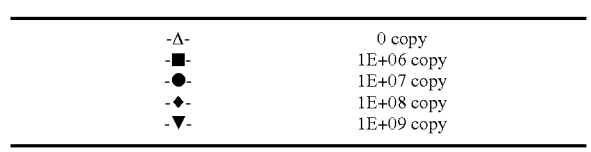

Figure 25:
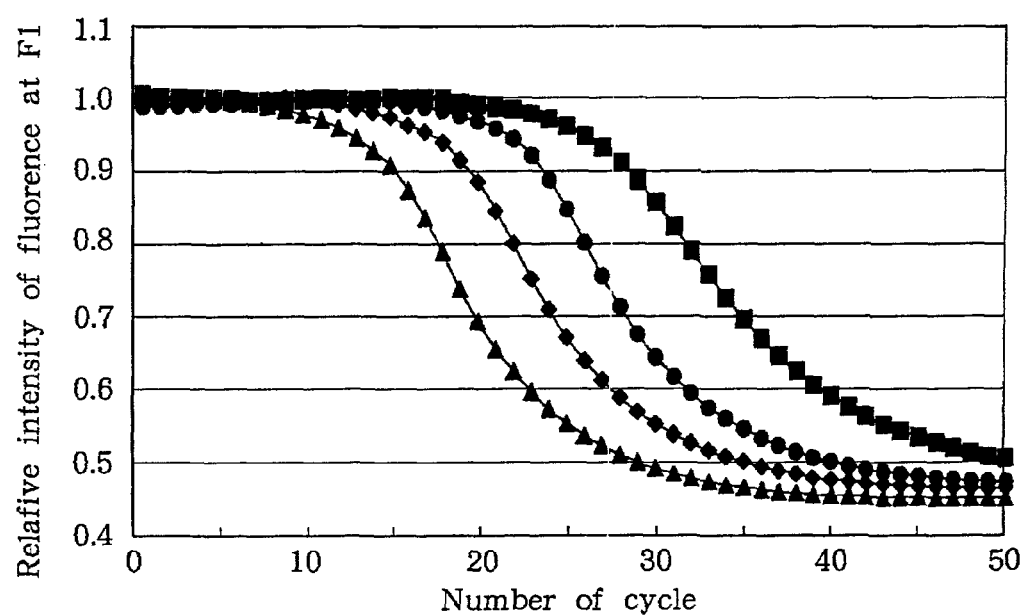

FIG. 25 illustrates real-time monitoring of PCR amplification product by making use of two fluorescence-labeled nucleotides (changes in the fluorescence at F1 after data processing).

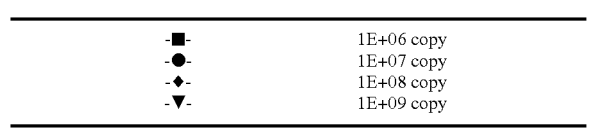

Figure 26:
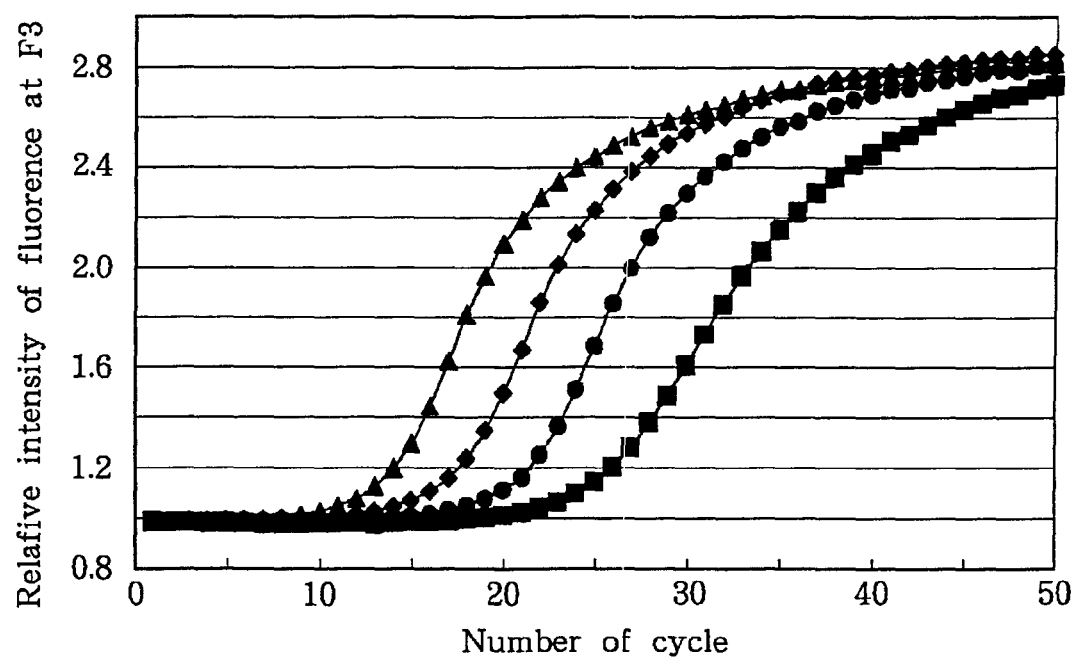

FIG. 26 illustrates real-time monitoring of PCR amplification product by making use of two fluorescence-labeled nucleotides (changes in the fluorescence at F3 after data processing).

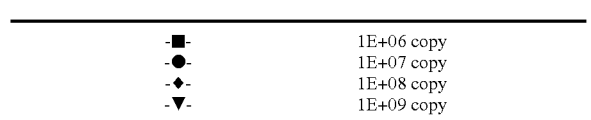

Figure 27:
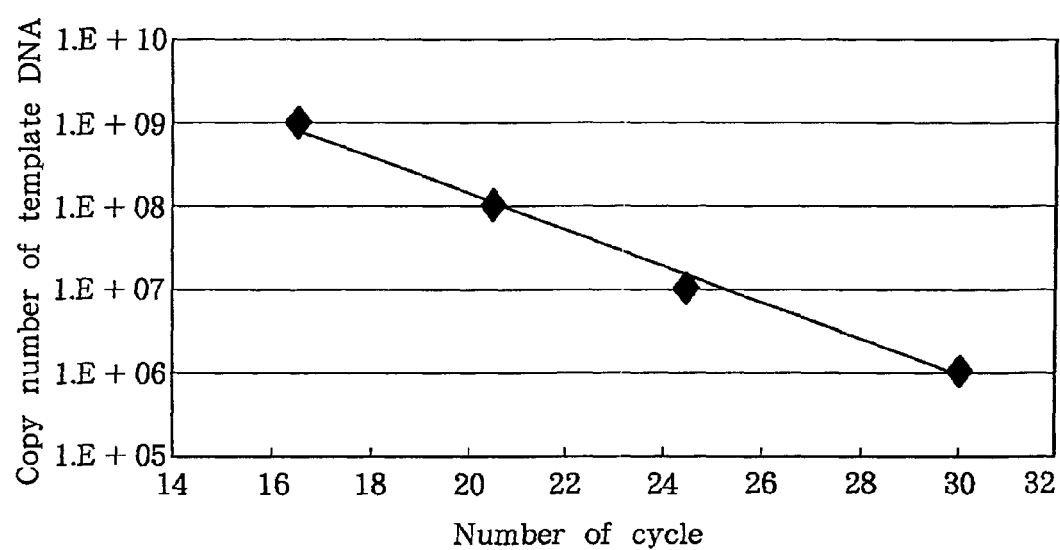

FIG. 27 illustrates a calibration line by a real-time quantitative PCR method making use of two fluorescence-labeled nucleotides (data employed for the preparation of the calibration line: fluorescence values at F1 after data processing).

Figure 28:
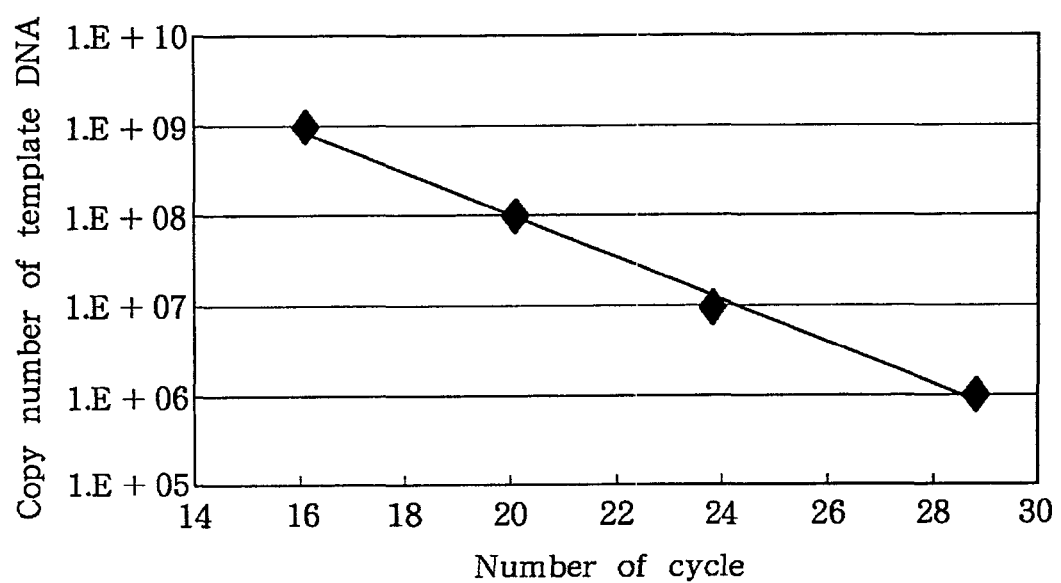

FIG. 28 illustrates a calibration line by a real-time quantitative PCR method making use of two fluorescence-labeled nucleotides (data employed for the preparation of the calibration line: fluorescence values at F3 after data processing).

Figure 29:
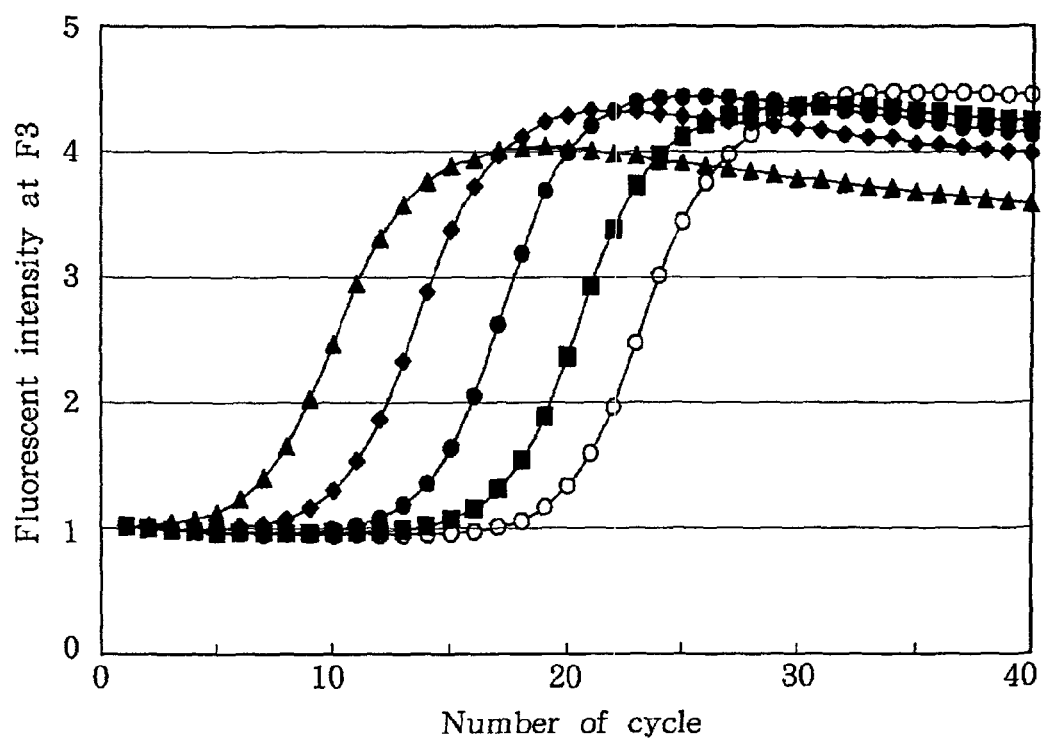

FIG. 29 illustrates real-time monitoring of PCT amplification product by using a double-stranded-nucleic-acid-specific fluorescent dye and a fluorescence-labeled nucleotide (changes in the fluorescence at F3 after data processing).

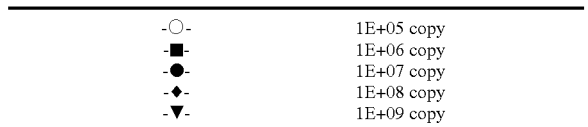

Figure 30:
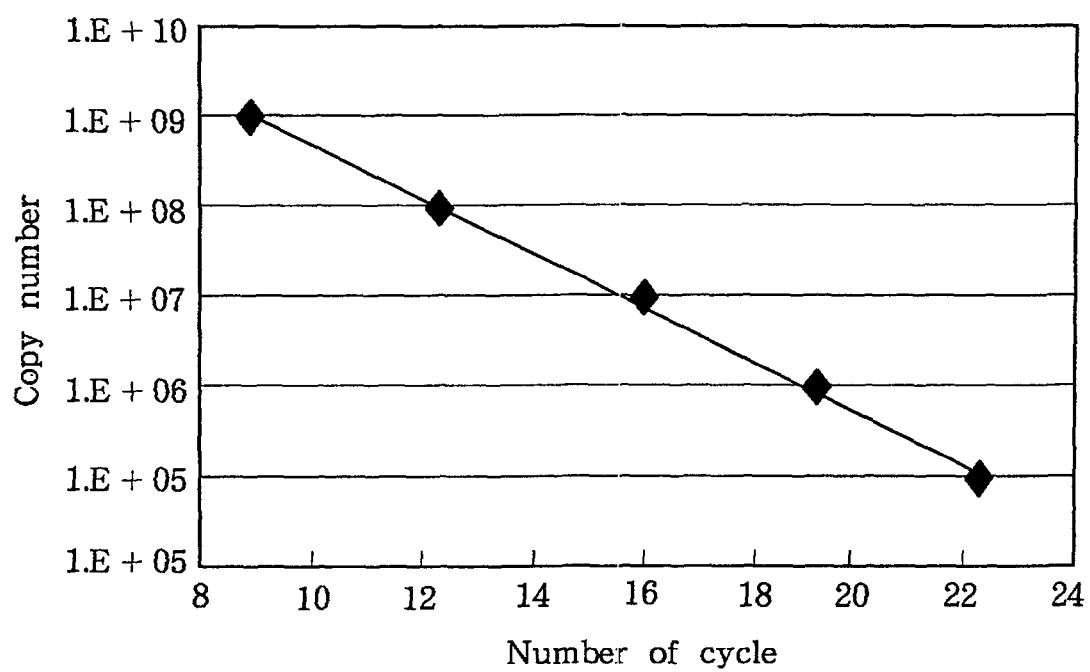

FIG. 30 illustrates a calibration line by a real-time quantitative PCR method making use of a double-stranded-nucleic-acid-specific fluorescent dye and a fluorescence-labeled nucleotide (changes in the fluorescence at F3 after data processing).

Figure 31:
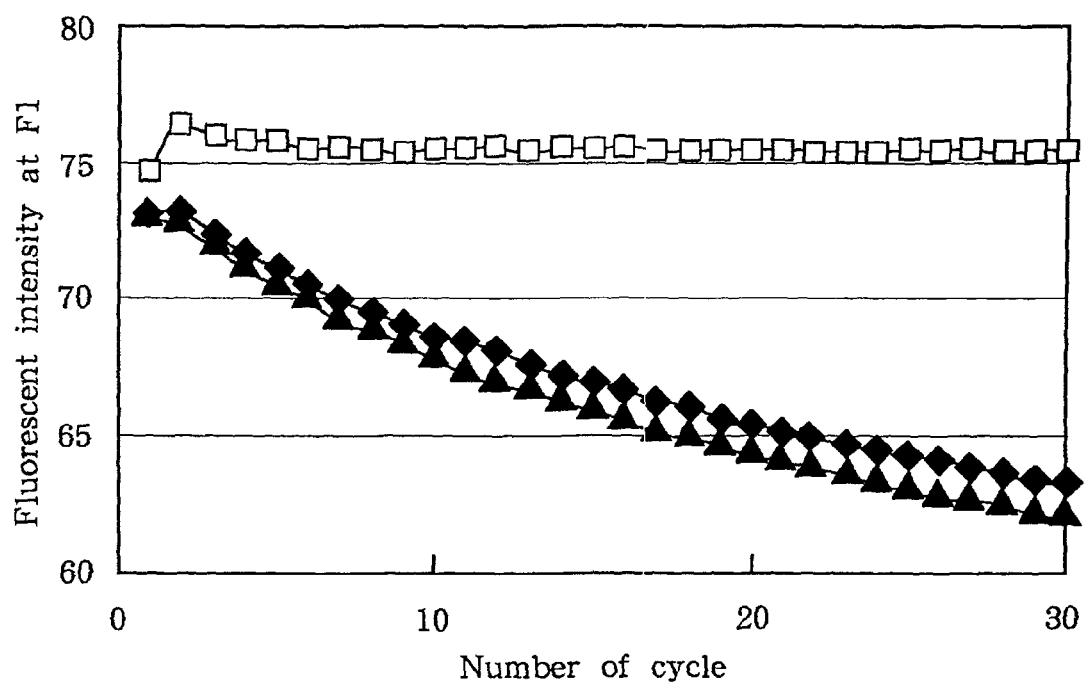

FIG. 31 is a diagram illustrating changes in the fluorescence intensity of FITC when primers 6 of three genotypes (-♦- C-allele homozygote, -□- T-allele homozygote, -▲-heterozygote) were used.

Figure 32:
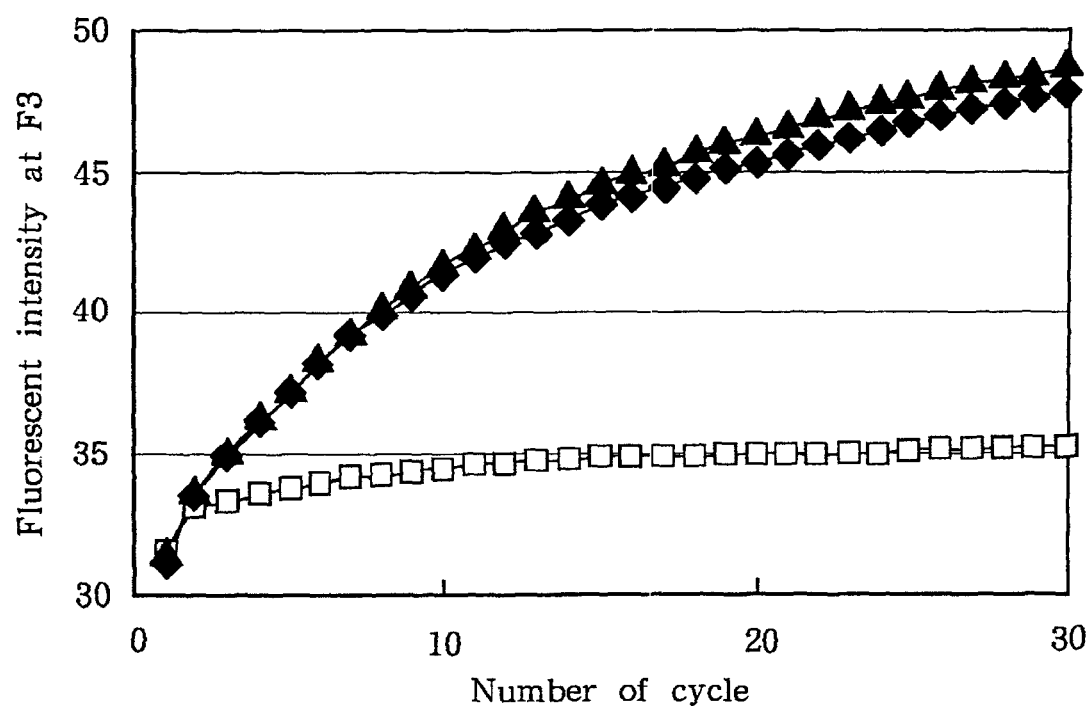

FIG. 32 is a diagram illustrating changes in the fluorescence intensity of CY5 when primers 6 of three genotypes (-♦- C-allele homozygote, -□- T-allele homozygote, -▲- heterozygote) were used.

Figure 33:
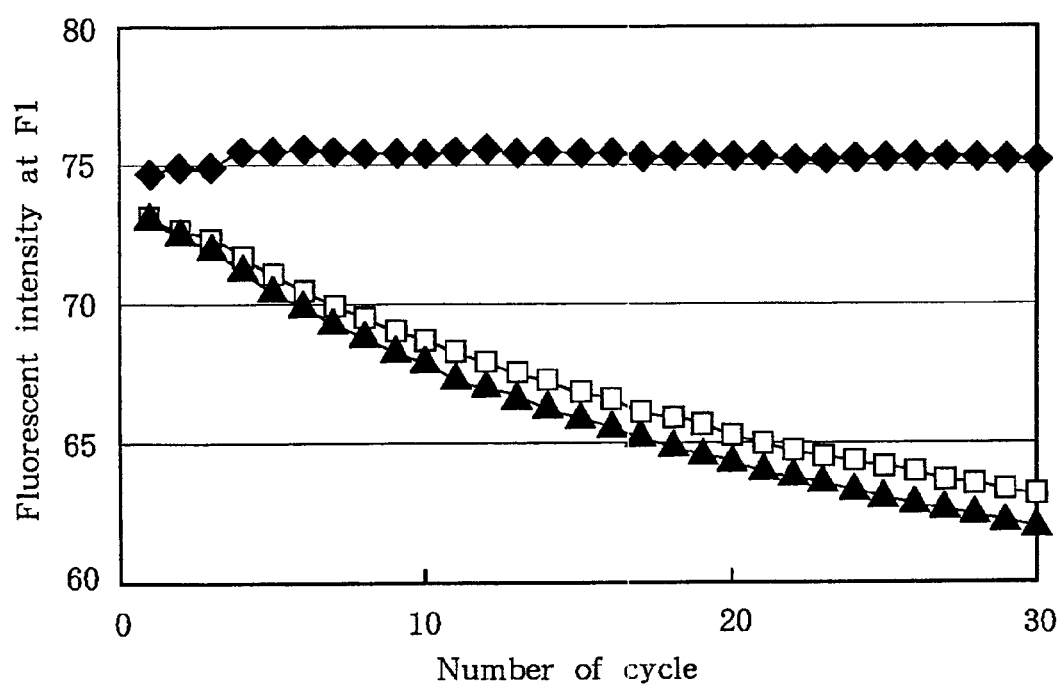
Figure 34:
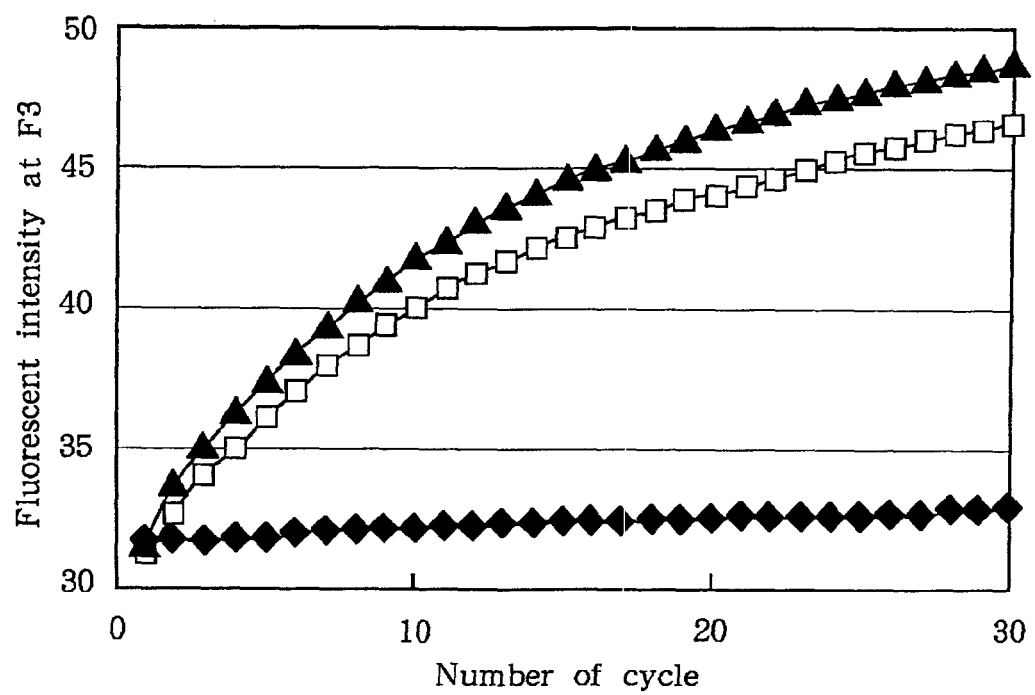

FIG. 33 is a diagram illustrating changes in the fluorescence intensity of FITC when primers 7 were used. -♦- C-allele homozygote, -□- heterozygote, -▲- T-allele homozygote FIG. 34 is a diagram illustrating changes in the fluorescence intensity at CY5 of FITC when primers 7 were used. -♦- C-allele homozygote, -□- heterozygote, -▲- T-allele homozygote

LEGEND

N: Nucleotide monomer

BEST MODES FOR CARRYING OUT THE INVENTION

The present invention will hereinafter be described in detail. Before describing the present invention in detail, however, definitions will be provided for certain terms used throughout the application including the claims. It is to be noted that the terms employed in the present invention have the same meanings as those used commonly in biology, molecular biology, genetics or genetic engineering, or microbiology or microbial engineering unless otherwise specifically indicated.

The term "nucleotide monomer" means a nucleotide which can be incorporated into a nucleic acid polymer by at least one nucleic acid-synthesizing enzyme . It can preferably be a mononucleotide of a nucleic acid constituent of an oligonucleotide.

Preferred examples can include nucleoside monophosphates (NMPs), nucleoside diphosphates (NDP), and nucleoside triphosphate (NTPs), with nucleoside triphosphates being more preferred. As a base, one contained in a nucleic acid constituent, specifically adenine, guanine, uracil, cytosine, thymine, a derivative thereof, a trace component contained in RNA, or the like can be mentioned. A sugar can be ribose or deoxyribose. Insofar as the above-described oligonucleotide is hybridizable with a template nucleic acid, it can be incorporated into a nucleic acid polymer in a nucleic acid polymerization system by using a nucleic acid-synthesizing enzyme having no exonuclease activity (for example, DNA polymerase) and ligase.

As a reason for the usability of a nucleoside monophosphate or diphosphate, a nucleic acid polymerization system may contain a kinase or phosphorylase, which converts the phosphate into the corresponding triphosphate, or a production system therefor. For example, an unpurified crude template nucleic acid or crude nucleic acid-synthesizing enzyme contain such an enzyme and/or its production system in many instances. When ATP is excessively contained in a nucleic acid polymerization system, the formation of triphosphates other than ATP is facilitated. The term "nucleic acid polymerization system" in the present invention is, therefore, defined such that it can encompass these enzymes and/or their production systems. This also applies equally to labeled nucleotides and nucleotides labeled with immune related substances, and hence, their triphosphates are more preferred. This also applies likewise to dideoxynucleotide monomers and labeled or unlabeled dideoxynucleotides, and accordingly, their triphosphates are more preferred.

The term "labeled nucleotide" means a nucleotide monomer labeled with at least one of fluorescent dyes, quencher substances and the like, which will be described subsequently herein. A nucleotide labeled with a fluorescent dye is called a "fluorescence-labeled nucleotide", while a nucleotide labeled with a quencher is called a "quencher-labeled nucleotide". Further, a fluorescent-labeled nucleotide labeled with a donor fluorescent dye is called a "donor-labeled nucleotide", while a fluorescent-labeled nucleotide labeled with an acceptor fluorescent dye is called an "acceptor-labeled nucleotide". About these labeled nucleotides, a detailed description will be made subsequently herein.

The term "unlabeled nucleotide" means a nucleotide monomer not labeled with such a labeling substance as described above.

The term "nucleic acid primer" means a primer which specifically hybridizes to a template nucleic acid. Nucleic acid primers labeled with a fluorescent dye and a quencher are called a "fluorescence-labeled nucleic acid primer" and a "quencher-labeled nucleic acid primer", respectively. Collectively, they are also called "labeled nucleic acid primers". Adenine, guanine, uracil, cytosine and thymine re designated "A" or "a", "G" or "g", "U" or "u", "C" or "c", or "T" or "t", respectively. A fluorescent dye, which emits fluorescence when bound to a nucleic acid, is defined as a nucleic-acid-specific fluorescent dye.

The term "template nucleic acid" means one that can serve as a template for a nucleic acid polymer. In the present invention, it indicates a nucleic acid which is unknown (which may also be called an "unknown nucleic acid"), a known nucleic acid (which may also be called a "target nucleic acid"), or a mixture thereof. It is a DNA and/or RNA. The term "template nucleic acid" used in the present invention, therefore, is not only limited to any specific nucleic acid(s) (target nucleic acid(s)) to be assayed, but also includes non-specific nucleic acid(s). Needless say, it encompasses genes and the like. These nucleic acids may exist together. In addition, no limitation is imposed on the concentration or size of the template nucleic acid. Accordingly, the term "template nucleic acid" also means one or more specific and/or non-specific nucleic acids existing in a single system. Specifically, the term "template nucleic acid" means a nucleic acid which can be detected or assayed by polymerization and/or amplification in accordance with the method of the present invention.

A nucleic acid-synthesizing enzyme can be any synthase insofar as it has ability to synthesize a nucleic acid polymer by polymerizing the above-described unlabeled nucleotide and/or labeled nucleotide while using the above-described nucleic acid template as a template. Representative examples can include DNA polymerases, RNA polymerases, reverse transcriptases, ligases, various kinases, nucleotide triphosphate production systems, and enzymes containing their modified proteins obtained by genetic engineering. These DNA polymerases, RNA polymerases and reverse transcriptases, ligases, various kinases, and enzymes containing nucleotide triphosphate production systems are suitably usable in the present invention. In the present invention, these nucleic acid-synthesizing enzyme can be used either singly or in combination.

Of course, these enzymes may or may not contain various factors which allow the enzymes to fully exhibit their activities. In the case of DNA polymerases, they may or may not be provided with the exonuclease activity, and they may be either in a purified form or in the form of an unpurified, crude enzyme. No particular limitation is imposed on the origin (microorganism, animal or plant) of the enzyme. However, those having heat resistance are preferred. Preferred specific examples can include VENT(EXO)DNA POLYMERASE (derived from Thermococcus litoralis), TGO(EXO)DNA POLYMERASE, "THERMOSEQUENASE DNA POLYMERASE" (product of Amersham Biosciences Corp.), AMPLITAGGOLD POLYMERASE, and T7Sequenase DNA polymerase, all of which have been rendered deficient in 3'→5' exonuclease activity.

A hybridization complex between a nucleic acid polymer or nucleic acid primer labeled with a florescent dye or the like and a corresponding nucleic acid such as a template or nucleic acid polymer is called a "hybrid (or hybrid) complex", "nucleic acid polymer-template complex", "nucleic acid primer-template complex", or "nucleic acid primer-nucleic acid polymer complex".

The expression "to assay a nucleic acid" or "to measure the concentration of a nucleic acid" as used herein means to perform a quantitative detection of the nucleic acid, to perform a qualitative detection of the nucleic acid, to simply measure or simply monitor the intensity of fluorescence from a nucleic acid polymerization system, to perform a simple detection of fluorescence, to analyze or study the nucleic acid, to measure, study and/or analyze a polymorphism (including SNP) and/or mutation, or to perform a like detection, measurement, study or analysis, to say nothing of quantitatively measuring the concentration of the target nucleic acid. The above expression should also be interpreter to encompass an operation or the like that the data obtain as described above is studied by the known method of Kurata et al. (EP 1 046 717 A9) to determine the concentration (the number of copies or the like) of a nucleic acid existing in a single system. Further, the above expression should also be interpreted to encompass an operation or the like that the sequence of a base is determined by a known method ("KISO SEIKAGAKU JIKKENHO (Fundamental Biochemical Experiments)", Vol. 4 (Experiments on Nucleic Acids and Genes), Compiled by the Japanese Biochemical Society, Published by Tokyo Kagaku Dojin Kabushiki Kaisha) or the like.

The term "polymerization reaction of a nucleic acid" encompasses not only mere polymerization (synthesis or elongation) reactions but also amplification reactions of the nucleic acid, for example, PCR techniques, real-time quantitative PCR techniques, ICAN techniques, LAMP techniques, NASBA techniques, TAMA techniques, LCR techniques, and hybridization reaction, elongations, modifications and the like making use of such techniques. As specific examples of the polymerization reaction, the following examples can be mentioned:

(1) a reaction in which a template nucleic acid is a DNA, a nucleic acid-synthesizing enzyme is a DNA polymerase or modified RNA polymerase, a nucleotide monomer or a fluorescence-labeled nucleotide or quencher-labeled nucleotide is a deoxyribonucleotide, and a nucleic acid polymer is a DNA;

(2) a reaction in which a template nucleic acid is a DNA, a nucleic acid-synthesizing enzyme is an RNA polymerase or modified DNA polymerase, a nucleotide monomer or a fluorescence-labeled nucleotide or quencher-labeled nucleotide is a ribonucleotide, and a nucleic acid polymer is an RNA;

(3) a reaction in which a template nucleic acid is an RNA, a nucleic acid-synthesizing enzyme is a reverse transcriptase, a nucleotide monomer or a fluorescence-labeled nucleotide or quencher-labeled nucleotide is a deoxyribonucleotide, and a nucleic acid polymer is a DNA;

(4) a reaction in which a template nucleic acid is an RNA, a nucleic acid-synthesizing enzyme is a reverse transcriptase or RNA polymerase, a nucleotide monomer or a fluorescence-labeled nucleotide or quencher-labeled nucleotide is a ribonucleotide or deoxyribonucleotide, and a nucleic acid polymer is an RNA, that is, a reaction which proceeds through a DNA synthesis reaction;

(5) a reaction system making combined use of a ligase in the above-described reaction system; and (6) a reaction system making combined use of one of various kinases and nucleotide triphosphate production systems in the above-described reaction system.

Among the above-described reaction systems, preferred are the reaction systems (1) to (4), more preferred are the reaction systems (1) to (3), and particularly preferred are the reaction systems (1) and (2).

The term "optical character" means one of various absorption spectra and fluorescence emission spectrum of a fluorescent dye, quencher or the like, with which a nucleotide is labeled, or its optical characteristic or the like such as absorption intensity, polarization, fluorescence emission, fluorescence intensity, fluorescence lifetime, fluorescence polarization or fluorescence anisotropy (these optical characteristics will be collectively called "fluorescence intensity"). It may also mean a characteristic determined by totally analyzing one or more measurement values of at least one fluorescent dye or the like, with which a labeled nucleotide or the like is labeled, as measured at least one measurement wavelength. For example, a fluorescence intensity curve or the like of a modification reaction of a nucleic acid can be used as an optical character.

In the present invention, the expression "from a change or an amount of a change in fluorescence intensity" shall embrace not only a change in fluorescence intensity on the basis of a nucleic acid polymer synthesized in the present invention, but also a change or an amount of a change in fluorescence intensity when a nucleic acid probe for a homogeneous solution system, said nucleic acid probe having been labeled with a fluorescent dye and/or quencher, is hybridized with the nucleic acid polymer.

A nucleic acid polymerization system may contain a labeled or unlabeled dideoxynucleotide together with a labeled or unlabeled nucleotide. When the dideoxynucleotide is used in the reaction, the polymerization of a nucleic acid in this system terminates as soon as the use of the dideoxynucleotide takes place. When a single species of target nucleic acid serves as a template, many nucleic acid polymers of different chain lengths are obtained using the target nucleic acid as their template. By analyzing and studying these nucleic acid polymers by electrophoresis, liquid chromatography or the like, important information can be obtained on the target nucleic acid. In such an analysis and study, a change in the intensity of fluorescence from the labeling substance is also used.

A detailed description will now be made about fluorescence-labeled nucleotides, quencher-labeled nucleotides, and nucleic-acid-specific fluorescent dyes. The term "fluorescent dye (which may also be called 'fluorescent substance')" as used in the present invention generally means a fluorescent dye which is generally used to label a nucleic acid probe to assay or detect the nucleic acid. Illustrative are fluoresce in and its derivatives [for example, fluorescein isothiocyanate (FITC) and its derivatives], Alexa 488, Alexa 532, CY3, CY5, 6-JOE, EDANS, rhodamine 6G (R6G) and its derivatives [for example, tetramethylrhodamine (TMR), tetramethylrhodamine isothiocynate (TMRITC), and x-rhodamine], TEXAS RED, "BODIPY FL" ("BODIPY" is a trademark, "FL" is a tradename; product of Molecular Probes Corporation, U.S.A.; this will hereinafter apply equally), "BODIPY FL/C3", "BODIPY FL/C6", "BODIPY 5-FAM", "BODIPY TMR", and their derivatives (for example, "BODIPY TR", "BODIPY R6G", and "BODIPY 564"). Among the above-exemplified fluorescent dyes, FITC, EDANS, TEXAS RED, 6-JOE, TMR, Alexa 488, Alexa 532, "BODIPY FL/C3", "BODIPY R6G", "BODIPY FL", Alexa 532, "BODIPY FL/C6", "BODIPY TMR", 5-FAM, "BODIPY 493/503", "BODIPY 564", "BODIPY 581", CY3, CY5, TEXAS RED, x-Rhodamine, and the like can be mentioned as preferred ones The term "quencher" means a substance, which acts on the above-described fluorescent dye and reduces or quenches the emission of fluorescence from the fluorescent dye. Illustrative are Dabcyl, "QSY7" (product of Molecular Probes Corporation), "QSY33" (product of Molecular Probes Corporation), Ferrocene and its derivatives, methyl viologen, and N,N'-dimethyl-2,9-diazopyrenium, with Dabcyl being preferred.

The term "fluorescence-labeled nucleotide" as used in the present invention means a nucleotide monomer labeled with at least one fluorescent dye. The labeling can be on the 5'-position of the sugar moiety and/or on the position of its phosphate group, on the position of the base, or on the 3'-position of the sugar moiety and/or on the position of its phosphate group. The term "fluorescent dye" means such a dye as exemplified above, which can act as a donor dye or an acceptor dye. Likewise, the term "quencher-labeled nucleotide" means a nucleotide monomer labeled with such a quencher as exemplified above. It is to be noted that a fluorescence-labeled nucleotide and a quencher-labeled nucleotide may also be collectively called "a labeled nucleotide". This applies equally to fluorescence-labeled dideoxynucleotides and quencher-labeled dideoxynucleotides. There is, however, no OH group at the 3'-position of the sugar moiety in such a dideoxynucleotide. When the dideoxynucleotide is used in the polymerization of a nucleic acid, the polymerization reaction, therefore, terminates as soon as the use of the dideoxynucleotide takes place.

When the 3'-OH group of the sugar moiety is labeled in the labeled nucleotide and the nucleotide is used in the polymerization reaction of the nucleic acid, the polymerization of the nucleic acid terminates as soon as the use of the nucleotide takes place. When a single species of target nucleic acid is used as a template, many nucleic acid polymers of different chain lengths are obtained using the target nucleic acid as their template. By analyzing and studying these nucleic acid polymers by electrophoresis, liquid chromatography or the like, important information can be obtained on the target nucleic acid. In such an analysis and study, a change in the intensity of fluorescence from the labeling substance is also used.

To label a nucleotide monomer with a fluorescent dye or a quencher, any desired one of conventionally known labeling methods can be used. The position to be labeled can be one of the OH groups in the 5'-phosphate group or an OH group or amino group in the base. When labeling the amino group, it is convenient to use a kit reagent, for example, "UNI-LINK AMINOMODIFIER" (product of CLONTECH LABORATORIES, INC., U.S.A.) or "FLUOROREPORTER KIT F-6082", "FLUOROREPORTER KIT F-6083", "FLUOROREPORTER KIT F-6084" or "FLUOROREPORTER KIT F-10220" (all, products of Molecular Probes Corporation, U.S.A.). By a method known per se in the art, molecules of the labeling substance can be bonded to the nucleotide monomer.

When labeling the OH group, "5'AMINO-MODIFIER C6 KIT" (Glen Research Corporation, U.S.A.) or the like is used. When bonding a molecule of the labeling substance, for example, to an OH group of a base, —$(CH_2)_n$—SH is firstly introduced as an illustrative spacer to the OH group by a method known per se in the art. In this case, n stands for 3 to 8, preferably for 6. A labeled nucleotide monomer can be synthesized by binding the labeling substance, which has reactivity to the SH group, or a derivative thereof to the spacer. This procedure can be followed likewise upon labeling the amino group. The 3'-OH groups of ribose and deoxyribose, the 2'-OH group of ribose and the OH group in the 5'-phosphate group can be labeled in a similar manner as described above. A variety of nucleotide monomers synthesized as described above and labeled with the above-described labeling substances can be purified by chromatography such as reverse phase chromatography to provide labeled nucleotides which are useful the present invention. Needless to say, they can also be obtained by relying upon custom synthesis services.

The term "nucleic acid primer for use in the present invention" means a primer which can serve as a precursor for a nuclear acid polymer. It can be either in a deoxyribose form or in a ribose form. No particular limitation is imposed on its chain length insofar as it can be used for the synthesis of a known nucleic acid. The chain length can be, for example, from 2 to 50 bases, more preferably from 3 to 40 bases, still more preferably from 5 to 30 bases. It is possible to use either a nucleic primer having such a base sequence as permitting specific hybridization to a template nucleic acid or a nucleic primer having a common base sequence or consensus sequence. A nucleic acid polymer making use of a specific nucleic acid template as a template can be obtained in the former case, while a non-specific nucleic acid polymer can be obtained in the latter case.

The primer in the present invention is usable no matter whether it is labeled with the above-described fluorescent dye or quencher. The labeling is required to have been effected by at least one of such labeling substances. A preferred nucleic acid primer is one labeled at the 5' end and/or the base in the chain but not labeled on the 3'-OH group at the 3' end of the sugar moiety. In this case, the resulting nucleic acid polymer is in a form labeled with the labeling substance employed to label the primer. Needless to say, it is also possible to use such a nucleic acid primer that the 3'-OH group at the 3' end of the sugar moiety has been labeled. In this case, the primer is used simply as a nucleic acid probe.

The oligonucleotide which makes up the nucleic acid primer for use in the present invention can be produced by a process commonly employed for producing general nucleotides. It can be produced, for example, by a chemical synthesis process, a biological process making use of a plasmid vector, phage vector or the like, or the like. The use of a nucleic acid synthesizer currently available on the commercial market is suited.

Labeling of an oligonucleotide with a fluorescent dye or quencher can be conducted in a similar manner as in the case of the above-described labeled nucleotide monomer. In this case, the target of labeling is the base at the 5' end of the oligonucleotide, the base at its 3' end, the phosphate group at its 5' end, or the ribose or deoxyribose at its 3' end. Concerning the synthesis of the oligonucleotide and that of the labeled nucleic acid primer, it is simplest to rely upon custom synthesis services.

The term "nucleic-acid-specific fluorescent dye" as used in the present invention means a substance which emits fluorescence when bound to a nucleic acid. No particular limitation is imposed on the species of the nucleic acid to which the substance is bound, insofar as it is a nucleic acid such as a labeled or unlabeled nucleic acid primer-template complex, a single-stranded DNA, a single-stranded RNA, a double-stranded nucleic acid formed of a DNA and an RNA, or a double-stranded RNA. Examples of the nucleic-acid-specific fluorescent dye include intercalators such as ethidium bromide, SYBR GREEN 1 SYBR GREEN 2, YOYO, TOTO, and YO-PRO-1. It is, however, to be noted that any substance can be applied to the method of the present invention insofar as it emits fluorescence when bound to a nucleic acid.

The present invention is directed to a method for assaying a nucleic acid, which comprises the following procedure:

1) To initiate a nucleic acid polymerization reaction (alone) or a nucleic acid polymerization reaction and nucleic acid amplification reaction (both) in any one of the following nucleic acid polymerization systems (1) to (8), preferably (6), (7) and (8), more preferably (6) and (7):

(1) a nucleic acid polymerization system containing a template nucleic acid, at least one labeled nucleotide, and a nucleic acid-synthesizing enzyme, (2) a nucleic acid polymerization system similar to the nucleic acid polymerization system (1) except for the additional inclusion of an unlabeled nucleotide, (3) a nucleic acid polymerization system containing a template nucleic acid, at least one labeled dideoxynucleotide, and a nucleic acid-synthesizing enzyme, (4) a nucleic acid polymerization system similar to the nucleic acid polymerization system (3) except for the additional inclusion of at least one nucleotide selected from the group consisting of labeled nucleotides and unlabeled nucleotides, (5) a nucleic acid polymerization system containing a template nucleic acid, an unlabeled dideoxynucleotide, a labeled nucleotide, and a nucleic acid-synthesizing enzyme, (6) a nucleic acid polymerization system similar to any one of the nucleic acid polymerization system (1) to (5) except for the additional inclusion of a labeled nucleic acid primer or an unlabeled nucleic acid primer, (7) a nucleic acid polymerization system containing a template nucleic acid, an unlabeled nucleotide, a labeled nucleic acid primer, and a nucleic acid-synthesizing enzyme, and (8) a nucleic acid polymerization system similar to any one of the nucleic acid polymerization system (1) to (7) except for the additional inclusion of a nucleic-acid-specific fluorescent dye.

2) To measure a change in the intensity of fluorescence from a nucleic acid polymerization system or the amount of the change. This change takes place because the labeled nucleotide and/or nucleic-acid-specific fluorescent dye is incorporated in the nucleic acid polymer as a reaction product in the course of the above-described reaction. When a nucleic acid probe caused to exist, the probe and the nucleic acid polymer are hybridized with each other so that the intensity of fluorescence from the nucleic acid polymerization system undergoes a unique change.

3) To analyze the reaction product by electrophoresis or HPLC as needed.

The above-described nucleic acid polymerization systems, especially in the nucleic acid polymerization system (6) which contains a nucleic acid primer, the assay method is suited when the nucleic acid as the output of the nucleic acid polymerization system is a DNA. The nucleic acid polymerization systems (1) and (2), on the other hand, are suited when the outputs of the nucleic acid polymerization systems are RNAs. Further, the nucleic acid polymerization systems each of which contains a labeled or unlabeled dideoxynucleotide are suited for use in assaying, analyzing or studying polymorphisms (including SNP) or mutations to be described subsequently herein.

The expression "in the presence or absence of at least one nucleic acid primer" is used in the present invention, because many of template nucleic acids (for example, crude template nucleic acids), samples each of which contains at least one template nucleic acid, and crude nucleic acid-synthesizing enzyme s each contains an oligonucleotide which may hybridize to the template nucleic acid to become a precursor for a nucleic acid polymer. It is also to be noted that many of such crude template nucleic acids and crude nucleic acid-synthesizing enzyme s contain an enzyme which synthesizes the precursor.

A nucleic acid polymerization reaction for the production of an RNA-type nucleic acid polymer may proceed even if the above-described nucleic acid primer is not allowed to exist.

When a nucleic acid synthesis system is contained in a template nucleic acid (for example, crude template nucleic acid) or in a sample containing at least one template nucleic acid (for example, a cell extract from one of various microorganisms), a nucleic acid polymerization reaction takes place even if no nucleic acid-synthesizing enzyme is added. In such a case, it is only necessary to initiate the reaction by causing at least one labeled nucleotide or nucleic-acid-specific fluorescent dye selected from the group consisting of fluorescence-labeled nucleotides, quencher-labeled nucleotides and nucleic-acid-specific fluorescent dyes.

The above-described reaction can be conducted under known reaction conditions. For example, the reaction temperature may be 10° C. or higher but lower than a nucleic acid denaturing temperature, and specifically relies upon the nucleic acid-synthesizing enzyme. When a DNA polymerase is used, for example, the reaction temperature can be 10° C. or higher but lower than the nucleic acid denaturing temperature, preferably from 30 to 90° C., more preferably from 30 to 80° C. When an RNA polymerase is used, the reaction temperature can be 30° C. to 60° C. When an reverse transcriptase is used, the reaction temperature can be 30° C. to 70° C. The reaction time is until the intensity of fluorescence from the nucleic acid polymerization system reaches an equilibrium when the intensity of fluorescence is monitored as a function of time. For example, the reaction time can be from 10 seconds to 10 hours, preferably from 10 seconds to 2 hours, more preferably from 10 seconds to 1 hour.

The above-described change in fluorescence intensity is presumably induced by at least one of phenomena in the below-described group. These phenomena interact with each other.

(1) Interaction between a nucleic-acid-specific fluorescent dye and a fluorescent dye [FRET (fluorescence resonance energy transfer) phenomenon], (2) Interaction between fluorescent dyes (FRET phenomenon), (3) Interaction (fluorescence quenching phenomenon) between a quencher and a fluorescent dye [same as the interaction (2)], and (4) Interaction between the guanine base and a fluorescent dye (fluorescence quenching phenomenon).

The term "interaction" as used in the present invention means a reaction in which excitation energy is transferred from one of the reactants to the other. "Fluorescence quenching phenomenon" may also be called simply "fluorescence quenching".

As a preferred, practical method for measuring a change in fluorescence intensity or the amount of the change, it is preferred and practical to measure in a real-time manner the intensity of fluorescence from a nucleic acid polymerization system and to determine the measurement value. In this method, it is desired to use a commercial measurement instrument which emits at least one incident light or excitation light and has at least one light-receiving surface such as a photomultiplier, in other words, which has multichannels. For example, "SMART CYCLER" (TAKARA BIO INC.), "ABI PRISM™ 7700 SEQUENCE DETECTION SYSTEM" (PE Applied Biosystems), "LIGHTCYCLER™ SYSTEM" (Roche Diagnostics, Mannheim, Germany), or the like can be used. To obtain an actual measurement value, at least one of the following measurements is conducted.

(1) Measurement of a nucleic acid polymerization system both before and after a nucleic acid polymerization reaction.

(2) Measurement of a nucleic acid polymerization system by using, as a control, a system in which no nucleic acid synthesis is allowed to proceed (for example, a system in which neither a template nucleic acid nor a nucleic acid-synthesizing enzyme is added).

(3) The intensity of fluorescence from a nucleic acid polymerization system in which the synthesis of a nucleic acid has reached equilibrium is measured firstly. The nucleic acid polymerization system is next subjected to nucleic acid denaturation treatment (for example, treatment at from 90 to 98° C.), followed by the measurement of the intensity of fluorescence from the nucleic acid polymerization system. By processing (analyzing) the measurement values, which have been obtained by the above-described method, in accordance with the below-described data analysis method, it is possible to ascertain the species of templates (unknown nucleic acids, a target nucleic acid) existing in a single system in the nature and also to determine their concentrations such as the numbers of their copies before the polymerization or amplification of these nucleic acids. As a result, still better data are obtained.

The characteristic features of the present invention will hereinafter be described with reference to the drawings.

Figure 1:
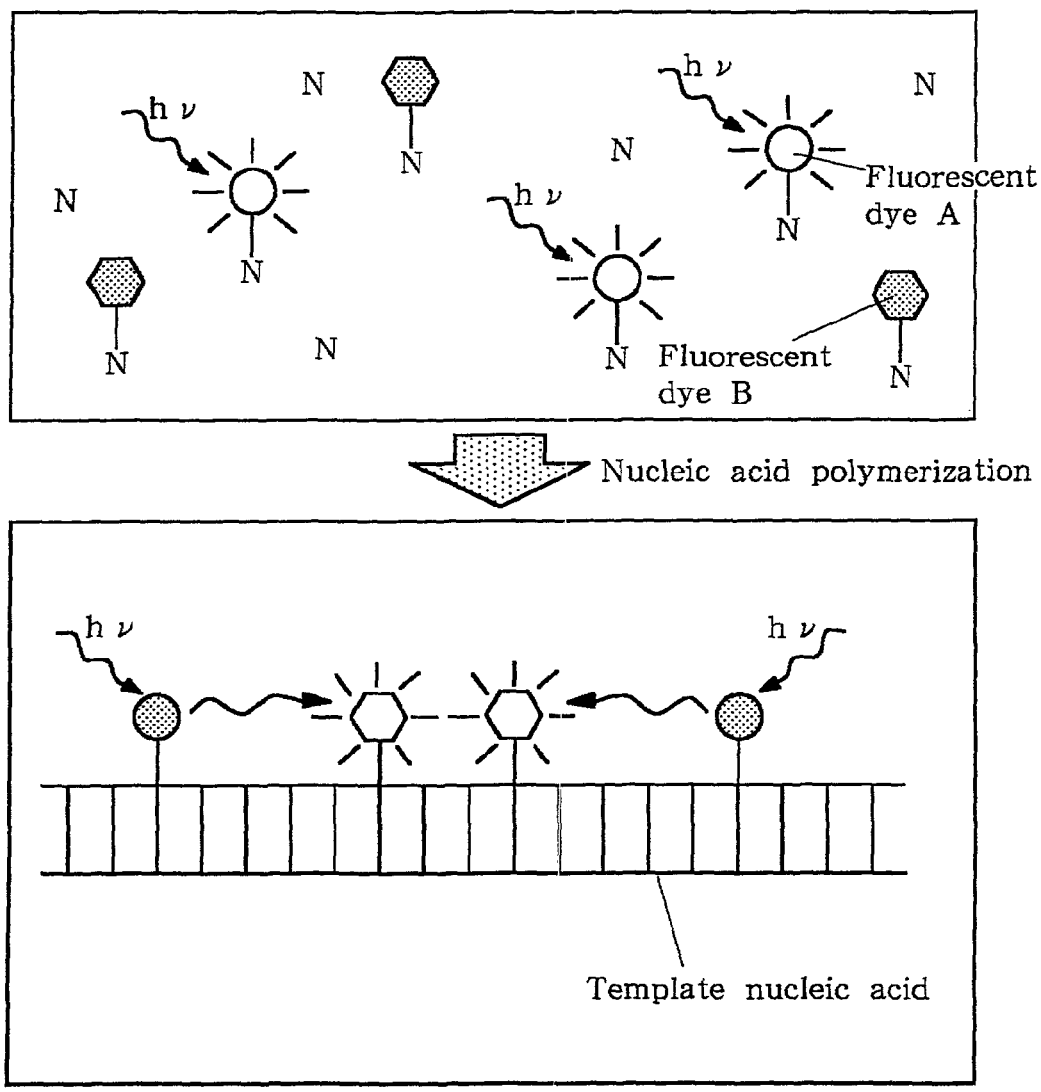
FIG. 1 illustrates an outline of a method A according to the present invention: a method of assaying a nucleic acid by making use of an interaction between florescent dyes.

1) Invention Method A (See FIG. 1)

(1) It is characterized in that a nucleic acid template or a nucleic acid polymer synthesized by using the nucleic acid template as a template is assayed by incorporating nucleotides—which are labeled by at least one fluorescent dyes, respectively—in the nucleic acid polymer and measuring a change in fluorescence character of a nucleic acid polymerization system due to an interaction between fluorescent dye (A) and fluorescent dye (B) in the incorporated fluorescence-labeled nucleotide or monitoring the change as a function of time (hereinafter simply called "monitoring"). This method is an illustrative method applicable when the nucleic acid polymerization system is the above-described nucleic acid polymerization system (1) or (2).

(2) In the above-described method (1), a nucleic acid polymerization reaction is conducted in a nucleic acid polymerization system with a nucleic acid primer contained therein. In this case, the nucleic acid primer is used as a precursor (primer) for a nucleic acid polymer. This method is an illustrative method applicable when the nucleic acid polymerization system is the above-described nucleic acid polymerization system (6).

When a fluorescence-labeled nucleotide is incorporated in a nucleic acid polymer as in the methods (1) and (2), the distance between the fluorescent dyes (A,B) in the incorporated fluorescence-labeled nucleotide significantly decreases so that an interaction takes place between the fluorescent dyes although this interaction did not occur in the state that the fluorescence-labeled nucleotide was dispersed in the solution (see FIG. 1). The nucleic acid template or the nucleic acid polymer synthesized by using the nucleic acid template as a template can be assayed by measuring or monitoring a change in fluorescence intensity due to the interaction between the fluorescent dyes or the amount of the change.

Of the fluorescent dyes interacting with each other in the above-described method, one of the fluorescent dyes is a dye which donates excitation energy for the FRET phenomenon, and is called a "donor dye" (A). The other fluorescent dye is a dye which emits fluorescence upon acceptance of the energy, and is called an "acceptor dye" (B).

The acceptor dye can generally be any dye insofar as it can act as an acceptor dye in the FRET phenomenon when paired with a donor dye or it can accept a transfer of energy from a donor dye (in other words, can give quenching effect to the donor dye). The donor dye, on the other hand, can be any dye insofar as it can transfer excitation energy to the acceptor dye. They can be suitably chosen from the above-described dyes.

Preferred examples of donor dyes can include FITC, "BODIPY FL", the above-described "BODIPY FL" series dyes, "BODIPY 493/503", "5-FAM", "BODIPY 5-FAM", tetramethylrhodamine, and 6-TAMRA, with FITC, "BODIPY FL", "BODIPY 493/503", "BODIPY 5-FAM", tetramethylrhodamine, and 6-TAMRA being more preferred.

A preferred acceptor dye varies depending upon the donor dye to be paired. When "BODIPY FL", the above-described "BODIPY FL" series dyes, "BODIPY 493/503", "5-FAM", "BODIPY 5-FAM", tetramethylrhodamine, (6-TAMRA and the like are used as donor dyes, for example, rhodamine X, "BODIPY 581/591" and the like can be used as acceptor dyes. This method measures an increase or decrease in the intensity of fluorescence at a particular wavelength from fluorescent dye(s) in a labeled nucleotide, that is, from a nucleic acid polymerization system. A decrease in fluorescence intensity is measured upon determining the intensity of fluorescence from a donor dye, and an increase in fluorescence intensity is measured upon determining the intensity of fluorescence from an acceptor dye.

Figure 2:
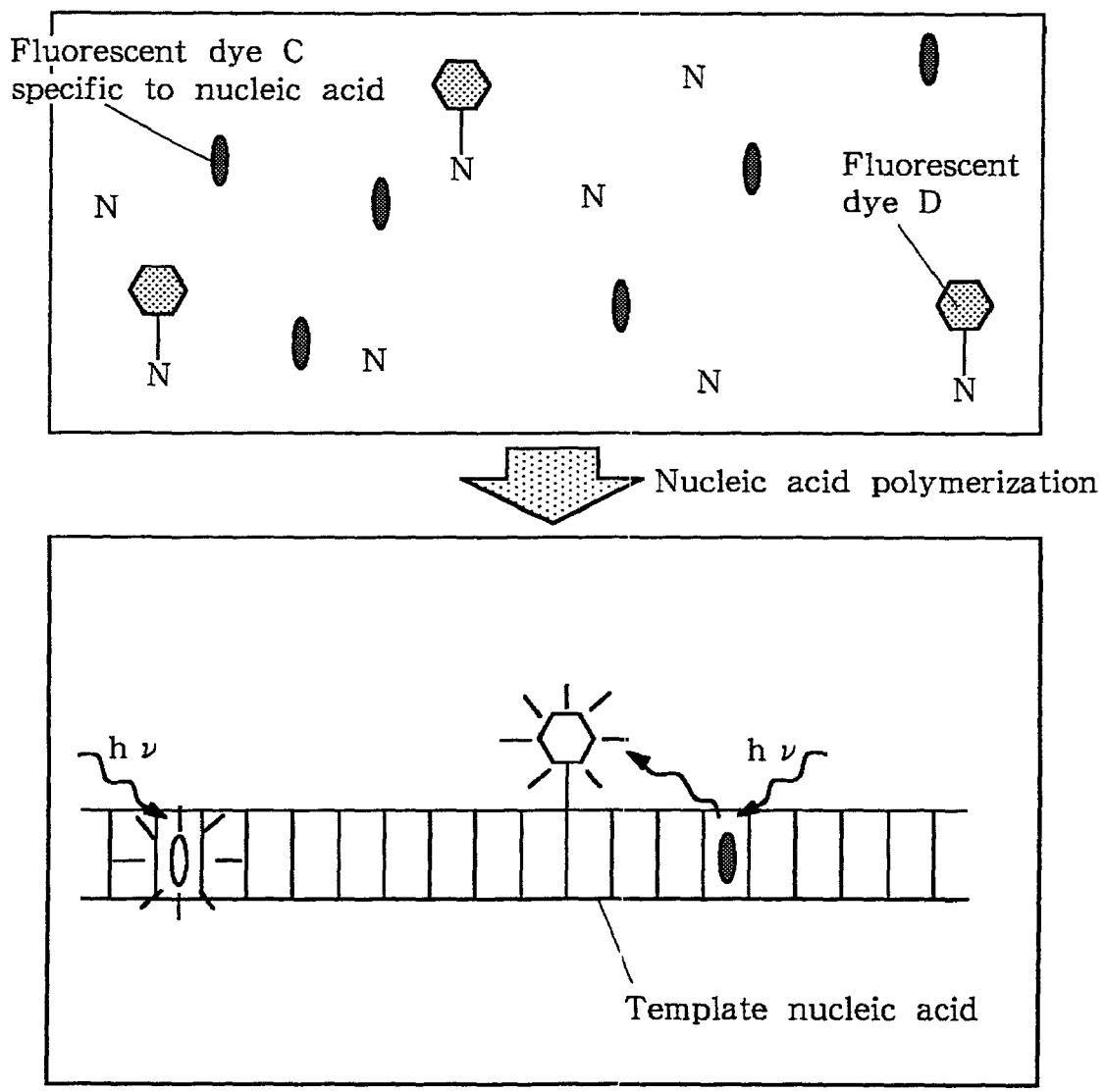
FIG. 2 illustrates an outline of a method B according to the present invention: a method of assaying a nucleic acid by making use of an interaction between a fluorescent dye specific to a nucleic acid (hereinafter referred to as "nucleic-acid-specific fluorescent dye") and a florescent dye.

2) Invention Method B (See FIG. 2)

This method is an illustrative method applicable when a nucleic acid polymerization system, to which the present invention can be applied, contains a nucleic-acid-specific fluorescent dye. Specifically, this method is an illustrative method applicable when the nucleic acid polymerization system is the above-described nucleic acid polymerization system (8). The nucleic-acid-specific fluorescent dye (C) binds to a nucleic acid polymer, a nucleic acid polymer-template complex, or a nucleic acid primer-template complex. An interaction takes place between fluorescent dye (D) in a fluorescence-labeled nucleotide, which has been incorporated in the nucleic acid polymer, and the nucleic-acid-specific fluorescent dye (C). The template nucleic acid or the nucleic acid polymer synthesized by using the template nucleic acid as a template can be assayed by measuring or monitoring a change in fluorescence intensity due to the interaction. This method measures a decrease in the intensity of fluorescence from the nucleic-acid-specific fluorescent dye (C) or an increase in the intensity of fluorescence from the fluorescent dye (D) in the labeled nucleotide. Specifically, an increase or decrease in the intensity of fluorescence at a particular wavelength from the nucleic acid polymerization system is measured.

In the course of conducting a reaction to incorporate a fluorescence-labeled nucleotide in a nucleic acid polymer in the presence of a nucleic-acid-specific fluorescent dye (C), the nucleic-acid-specific fluorescent dye (C) binds to the synthesized nucleic acid polymer, and therefore, the distance between the fluorescent dye (C) and a fluorescent dye (D) in the fluorescence-labeled nucleotide incorporated in the course of the reaction significantly decreases as described above (see FIG. 2). Accordingly, a similar interaction takes place between the fluorescent dyes.

As the fluorescent dye (D) in this method, the above-described fluorescent dyes are all usable, and preferred examples can include FITC, EDANS, 6-joe, TMR, Alexa 488, Alexa 532, "BODIPY FL/C3", "BODIPY R6G", "BODIPY FL", Alexa 532, "BODIPY FL/C6", "BODIPY TMR", 5-FAM, "BODIPY 493/503", "BODIPY 564", "BODIPY 581", CY3, CY5, TEXAS RED, and x-Rhodamine. The above-described examples of the nucleic-acid-specific fluorescent dye (C) are also all usable, with SYBR GREEN 1 and YO-PRO-1 being preferred. Preferred examples of the combination of fluorescent dyes can include the combinations between SYBR GREEN and TEXAS RED, 6-JOE, TMR, Alexa 532, BODIPY R6G, Alexa 532, BODIPY TMR, BODIPY 564, BODIPY 581, CY3, CY5 and x-Rhodamine; and the combinations between YO-PRO-1 and TEXAS RED, 6-JOE, TMR, Alexa 532, "BODIPY R6G", Alexa 532, "BODIPY TMR", "BODIPY 564", "BODIPY 581", CY3, CY5, TEXAS RED, x-Rhodamine.

3) Invention Method C

This is an assay method of a nucleic acid, which is characterized by conducting a nucleic acid polymerization reaction in a nucleic acid polymerization system—which contains a fluorescence-labeled nucleotide, one or more unlabeled nucleotides, a nucleic acid template and a nucleic acid-synthesizing enzyme with or without an unlabeled nucleic acid primer—and assaying the nucleic acid template or a nucleic acid polymer, which has been synthesized using the nucleic acid template as a template, from a decrease in the intensity of fluorescence from the nucleic acid polymerization system or from the amount of the decrease. It is preferred that at least one of the unlabeled nucleotides contains guanine (g) an/or the template nucleic acid contains at least one guanine (g). Described specifically, the base of the template nucleic acid, said base corresponding to the base of the fluorescent-labeled nucleotide incorporated in the nucleic acid polymer, forms a gc (GC) pair, or the template nucleic acid contains G at a position 1 to 3 bases apart from the base of the fluorescence-labeled nucleotide (said corresponding base being counted as "one" base) or the nucleic acid polymer contains an unlabeled nucleotide the base of which is G. This assay method of the nucleic acid relies upon a change in fluorescence intensity based on an interaction between the fluorescent dye (E) and G. This method is an illustrative method applicable when the nucleic acid polymerization system is the above-described nucleic acid polymerization system (2).

The decrease in the intensity of fluorescence from the polymerization reaction system takes place in any one of the following situations:

(1) The base of a fluorescence-labeled nucleotide is cytosine (c) or guanine (g), (2) The base of at least one fluorescence-labeled nucleotide is guanine (g), and (3) The template nucleic acid contains at least one guanine (g).

Figure 3:
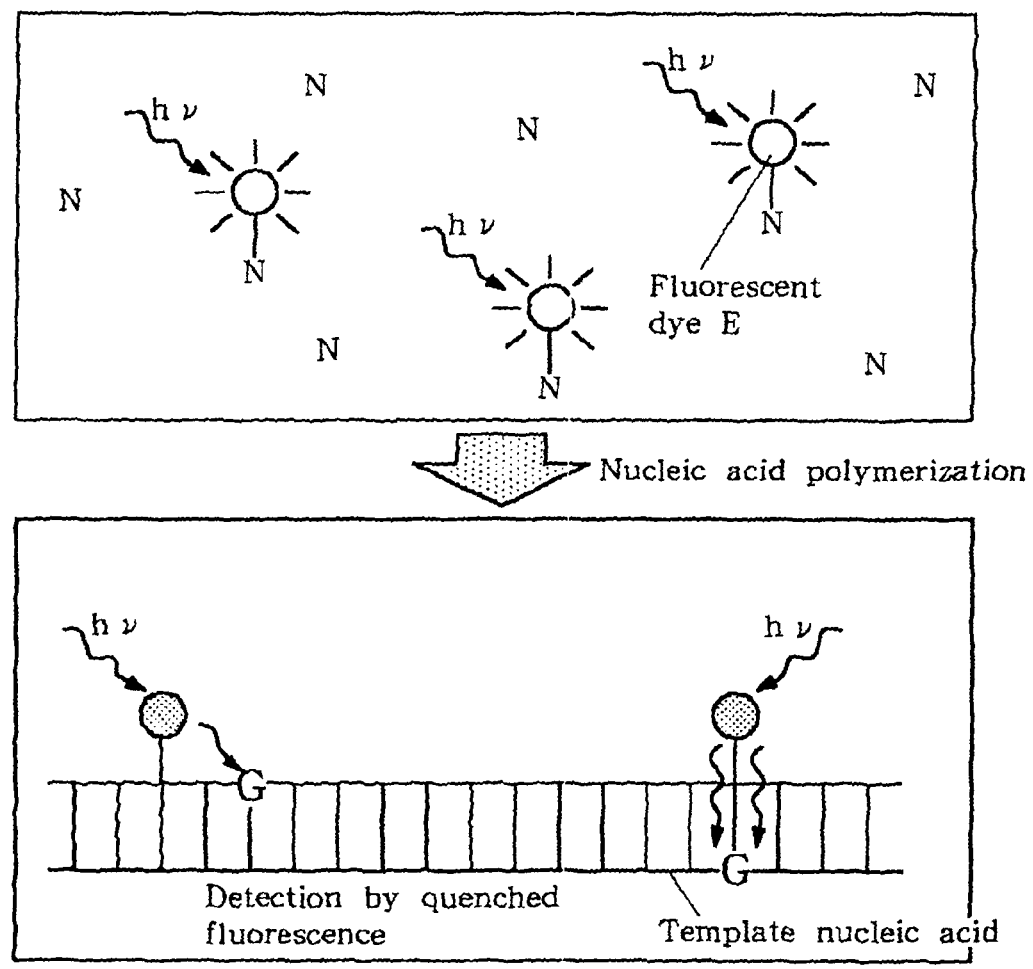
FIG. 3 illustrates an outline of a method C according to the present invention: a method of assaying a nucleic acid by making use of an interaction between the base G and a florescent dye.

In the course of conducting a nucleic acid polymerization reaction by using a fluorescence-labeled nucleotide and/or an unlabeled nucleotide, the distance between the guanine (g) in the template or the guanine (g) in the guanine (g)-containing unlabeled nucleotide incorporated in the synthesized nucleic acid polymer and the fluorescent dye (E) in the incorporated, fluorescence-labeled nucleotide significantly decreases as described above (see FIG. 3). Accordingly, excitation energy is transferred from the fluorescent dye (E) to the guanine (b) base although such a transfer did not take place in the state that the fluorescence-labeled nucleotide and/or an unlabeled nucleotide and the template were dispersed in the solution.

As the fluorescent dye (E) labeling the fluorescence-labeled nucleotide in this method, the above-described fluorescent dyes are all usable, and preferred examples can include FITC, EDANS, TEXAS RED, 6-JOE, TMR, Alexa 488, Alexa 532, "BODIPY FL/C3", "BODIPY R6G", "BODIPY FL", Alexa 532, "BODIPY FL/C6", "BODIPY TMR", 5-FAM, "BODIPY 493/503", "BODIPY 564", "BODIPY 581", CY3, CY5, TEXAS RED, and x-Rhodamine.

The preferred nucleotide monomer to be fluorescence-labeled may be a nucleotide monomer containing cytosine as a base (cytidylic acid, cytidine 5'-phosphate, cytidine 5'-diphosphate, cytidine 5'-triphosphate, or a polymer thereof, or a polymer containing cytidylic acid), and the position of labeling can be a base (amino group), phosphate group (OH group), or a ribose moiety (2'- or 3'-OH group). The preferred position is either a base or a phosphate group.

Figure 4:
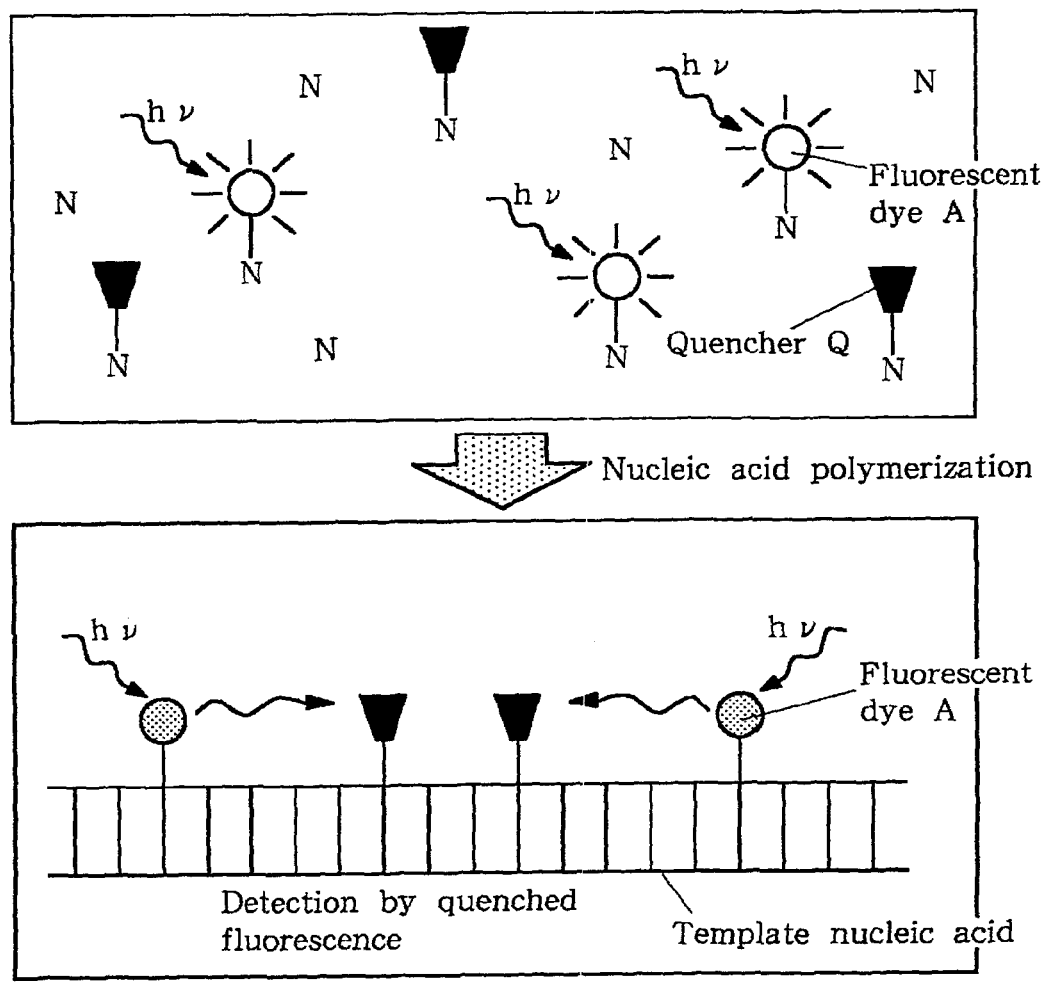
FIG. 4 illustrates an outline of a method D according to the present invention: a method of assaying a nucleic acid by making use of an interaction between a quencher and a florescent dye.

4) Invention Method D (See FIG. 4)

This method is an illustrative method similar to the method (1) or (2) of the invention method A except that a fluorescence-labeled nucleotide and quencher-labeled nucleotide are both used. Described specifically, when the fluorescence-labeled nucleotide and quencher-labeled nucleotide are incorporated in a nucleic acid polymer, a florescent dye (A) in the incorporated fluorescence-labeled nucleotide and a quencher (Q) in the quencher-labeled nucleotide come close to each other and interact with each other (see FIG. 4), resulting in a decrease in the intensity of fluorescence from the nucleic acid polymerization system. This method is characterized in that a template nucleic acid or a nucleic acid polymer synthesized by using the template nucleic acid as a template is assayed by measuring this decrease in fluorescence intensity or monitoring the decrease. This method is an illustrative method applicable when the nucleic acid polymerization system is the above-described nucleic acid polymerization system (1) or (2). Practically, a decrease in the intensity of fluorescence from the nucleic acid polymerization system is measured.

Examples of the quencher (also called "fluorescence quenching substance") usable in this method include Dabcyl, "QSY7" (product of Molecular Probes Corporation), "QSY33" (product of Molecular Probes Corporation), derivatives thereof, methyl viologen, and N,N'-dimethyl-2,9-diazopyrenium.

When the nucleic acid polymerization reaction is conducted in the presence of the fluorescence-labeled nucleotide and quencher-labeled nucleotide in the nucleic acid polymerization system, the fluorescence-labeled nucleotide and quencher-labeled nucleotide are incorporated in the nucleic acid polymer as described above. As a result of the incorporation in the nucleic acid polymer, the distance between the fluorescence-labeled nucleotide and quencher-labeled nucleotide significantly decreases so that the distance between the fluorescent dye (A) and the quencher (Q) also decreases significantly (see FIG. 4). Accordingly, an interaction (a transfer phenomenon of light-emitting energy) takes place between the quencher (Q) and the fluorescent dye (A) although such an interaction did not take place in the state that the fluorescence-labeled nucleotide and quencher-labeled nucleotide were dispersed in the solution.

Figure 5:
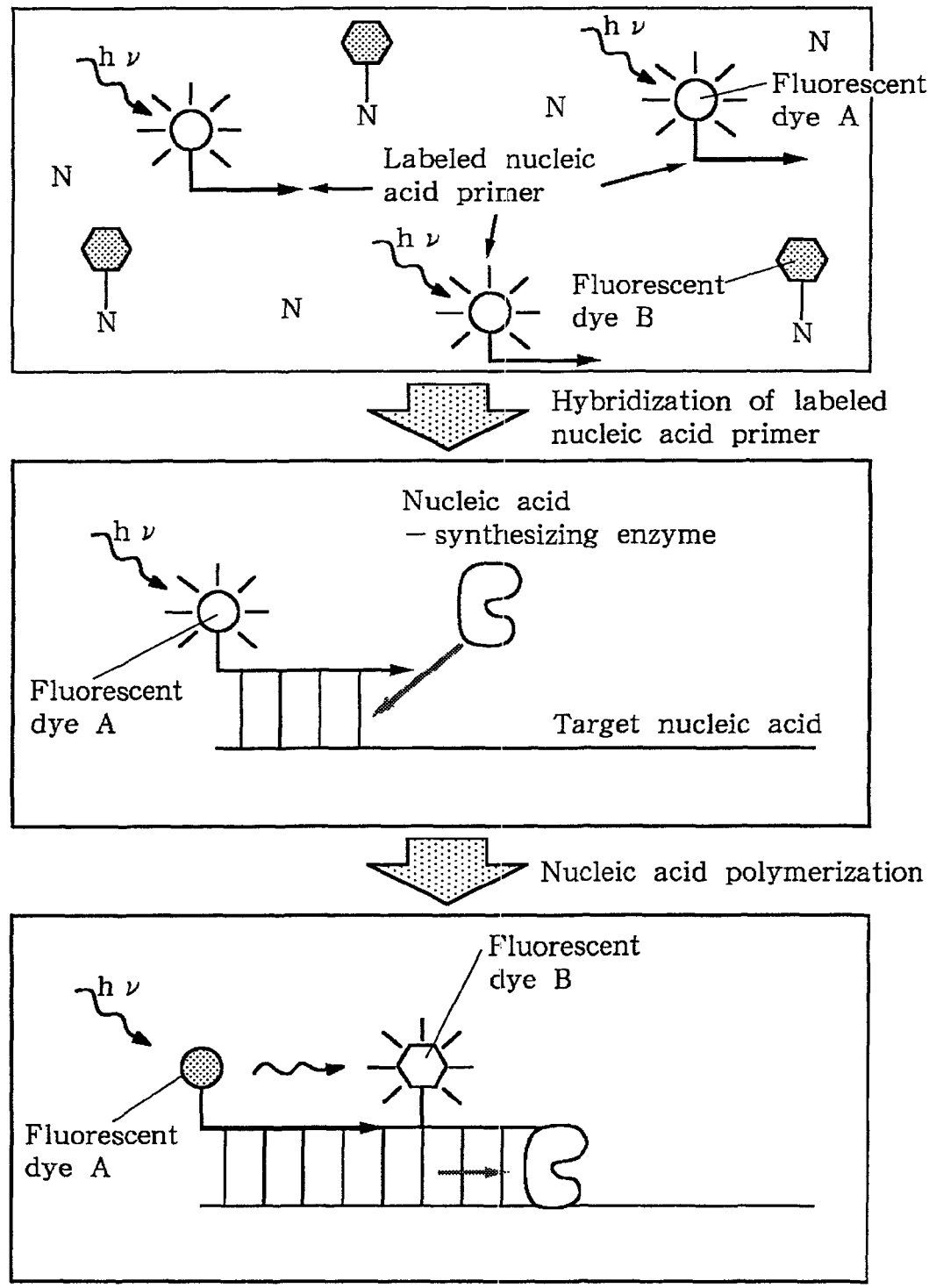
FIG. 5 illustrates an outline of a method E according to the present invention: (1) a method of assaying a nucleic acid by making use of a labeled specific primer.
Figure 6:
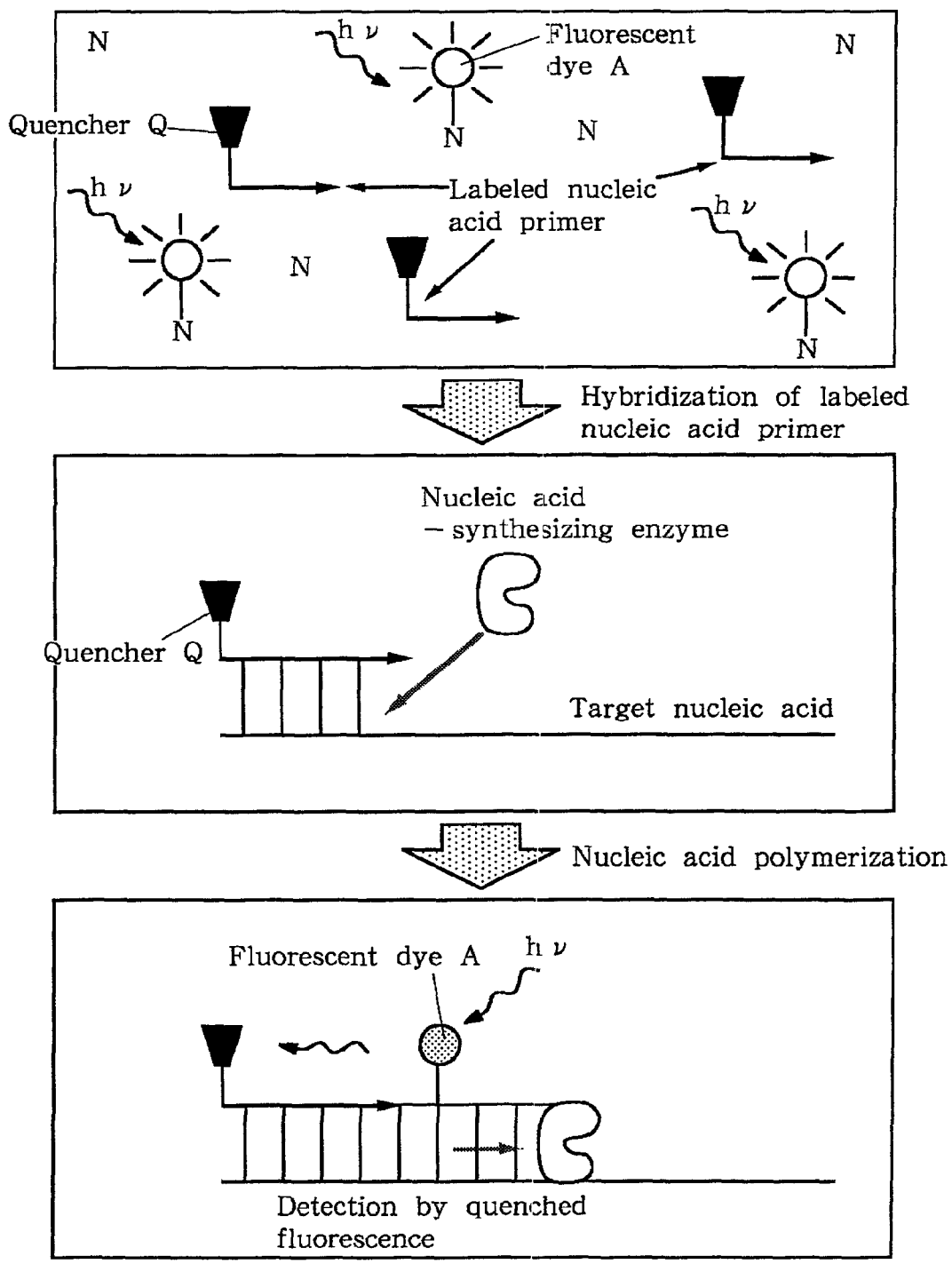
FIG. 6 illustrates an outline of the method E according to the present invention: (2) a method of assaying a nucleic acid by making use of a labeled specific primer.

5) Invention Method E (See FIG. 5 and FIG. 6)

This method is an illustrative method similar to the method (2) of the invention method A except that a labeled nucleic acid primer is used as a nucleic acid primer. In the course of conducting polymerization of a template nucleic acid, a labeled nucleotide is incorporated in the nucleic acid polymer. By an interaction between a fluorescent dye (A) or quencher (Q) in the labeled nucleic acid primer and a fluorescent dye (A) or quencher (Q) in the labeled nucleotide, the intensity of fluorescence changes. According to this method, this change is measured or monitored to assay the template nucleic acid or the nucleic acid polymer synthesized by using the template nucleic acid as a template. This method is an illustrative method applicable when the nucleic acid polymerization system is the above-described nucleic acid polymerization system (6). Practically, an increase or decrease in the intensity of fluorescence from the nucleic acid polymerization system is measured. In this case, the increase or decrease in florescence intensity varies depending upon the combination of fluorescent dye (A) or quencher (Q) in the labeled nucleotide and the fluorescent dye (A) or quencher (Q) as a label in the labeled nucleic acid primer. A donor dye and acceptor dye have a similar interaction as in the invention method A. A quencher and fluorescent dye have a similar interaction as in the invention method D.

When a nucleic acid polymerization reaction is conducted in a similar manner as in the invention method A except for the use of the labeled nucleic acid primer and the fluorescence-labeled nucleotide, the labeled nucleic acid primer and fluorescence-labeled nucleotide are incorporated in the nucleic acid polymer as described above. As a result of the incorporation in the nucleic acid polymer, the distance between the labeled nucleic acid primer and the fluorescent dye (A) or quencher (Q) in the fluorescence-labeled nucleotide significantly decreases (see FIG. 5 and FIG. 6). Accordingly, an interaction takes place between the fluorescent dye (A) or quencher (Q) in the labeled nucleic acid primer and the fluorescent dye (A) or quencher (Q) in the labeled nucleotide although such an interaction did not take place in the state that the labeled nucleic acid primer and labeled nucleotide were dispersed in the solution.

As substance-substance interactions which may take place in the present invention, the following three cases can be contemplated: (1) an interaction between the fluorescent dye (A) in the labeled nucleic acid primer and the fluorescent dye (B) in the labeled nucleotide; (2) an interaction between the fluorescent dye (A) in the labeled nucleic acid primer and the quencher (Q) in the labeled nucleotide; and (3) an interaction between the quencher (Q) in the labeled nucleic acid primer and the fluorescent dye (A) in the labeled nucleotide [FIG. 5 illustrates the case (1), while FIG. 6 depicts the case (3)]. Different from a nucleic acid probe for a homogeneous solution system according to the known technique, said nucleic acid probe being to be described subsequently herein, it is not necessary to design the above-described labeled nucleic acid primer in such a way that the intensity of fluorescence changes when hybridized to a template. This method, therefore, has an advantage in that the establishment of an experiment system is simple, easy and sure. Fluorescent dyes preferred for use in this method are similar to those exemplified above in connection with the invention method A. On the other hand, quenchers preferred for use in this method are similar to those exemplified above in connection with the invention method D.

Figure 7:
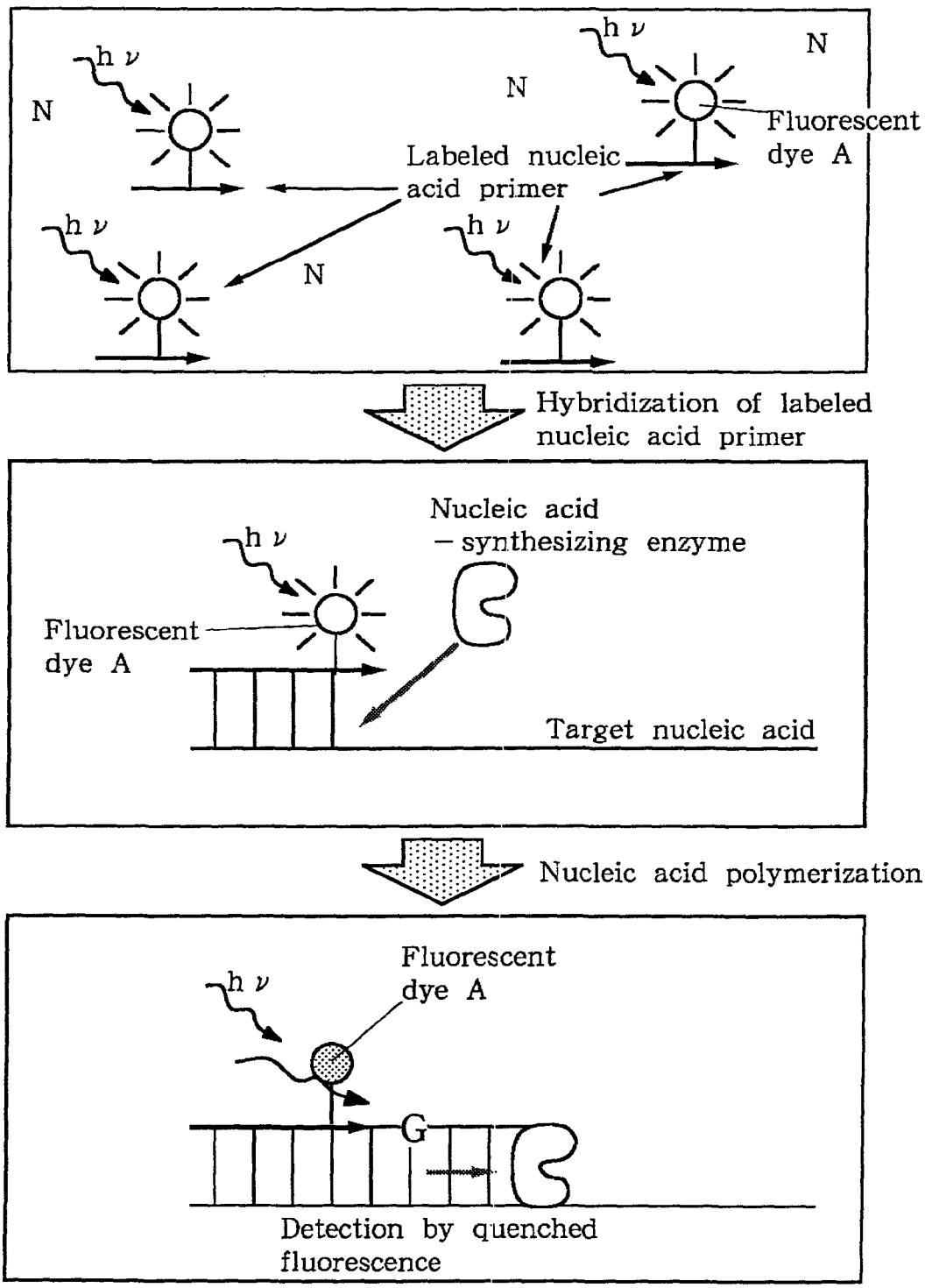
FIG. 7 illustrates an outline of a method F according to the present invention: a method of assaying a nucleic acid by making use of an interaction between a fluorescence dye labeled with a specific primer and the base G.

6) Invention Method F (See FIG. 7)

This is an illustrative method similar to the method (2) of the invention method A except that a labeled nucleic acid primer is used as a nucleic acid primer and an unlabeled nucleotide is used in place of a labeled nucleotide (in other words, no labeled nucleotide is used). By an interaction between a fluorescent dye (A) contained as a label in the labeled nucleic acid primer and the G base in the unlabeled nucleotide with the G base incorporated therein, the intensity of fluorescence from the nucleic acid polymerization system decreases. This method is characterized in that a template nucleic acid or a nucleic acid polymer synthesized by using the template nucleic acid as a template is assayed by measuring this decrease in fluorescence intensity or monitoring the decrease. This method is an illustrative method applicable when the nucleic acid polymerization system is the above-described nucleic acid polymerization system (7).

Described specifically, an interaction takes place when an unlabeled nucleotide contains G and moreover, when at a position 1 to 3 bases apart from the base labeled with the fluorescent dye (A) of the fluorescence-labeled nucleic acid primer in a synthesized nucleic acid polymer, said labeled base being counted as the $1^{st}$ base, a newly polymerized nucleic acid polymer contains at least one G (which is meant to be a base other than any one of the bases in the chain of the primer) (see FIG. 7). Different from a nucleic acid probe for a homogeneous solution system according to the known technique, it is not necessary to design the above-described labeled nucleic acid primer in such a way that the intensity of fluorescence changes when hybridized to a template. Similar to the invention method E, this method hence has an advantage in that the establishment of an experiment system is simple, easy and sure. Fluorescent dyes preferred for use in this method are similar to those exemplified above in connection with the invention method C.

Figure 8:
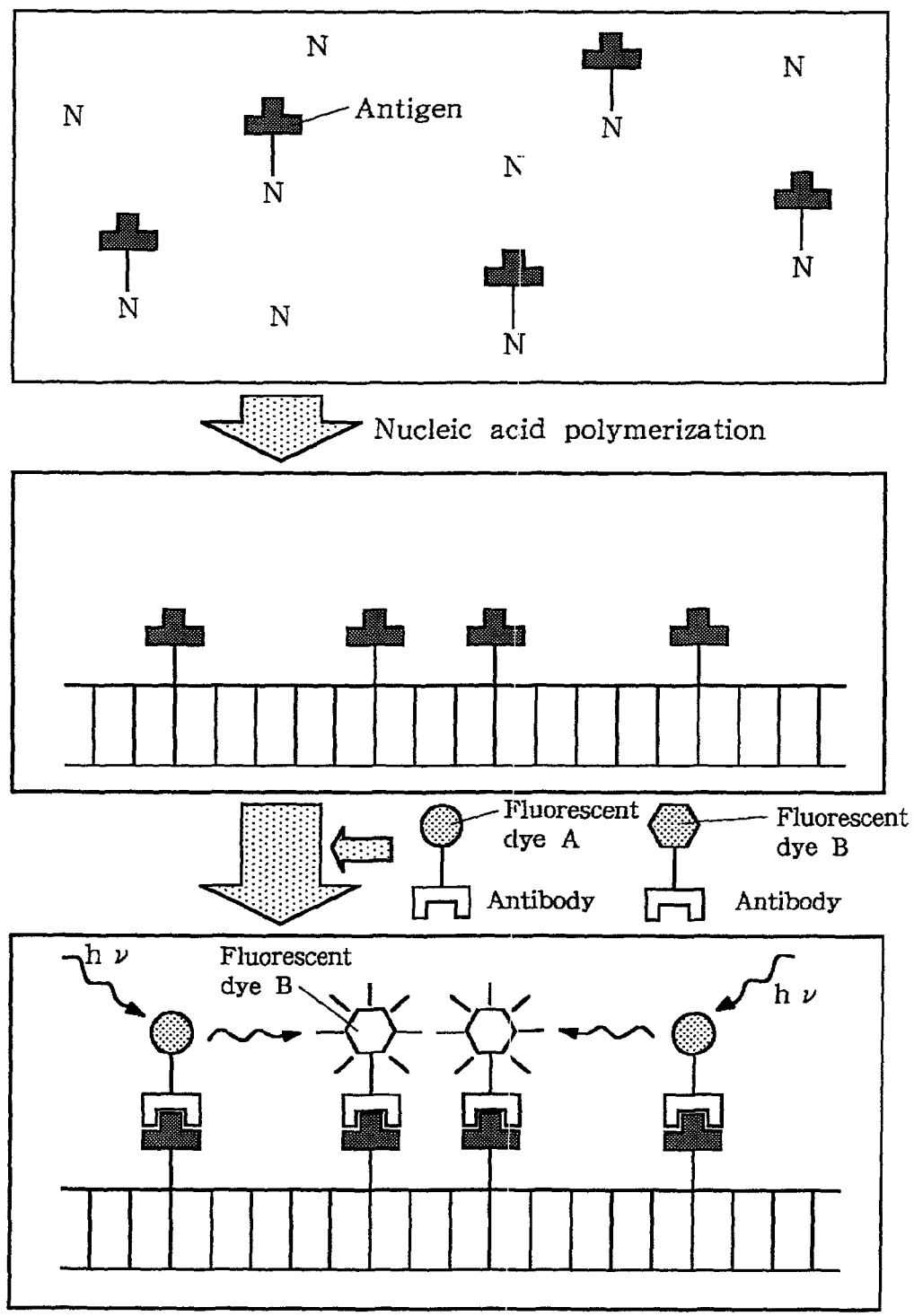
FIG. 8 illustrates an outline of the method G according to the present invention: a method of assaying a nucleic acid by making use of a nucleotide labeled with an antigen or antibody.

7) Invention Method G (See FIG. 8)

This is an illustrative method similar to any one of the invention methods A to F except that instead of using the fluorescence-labeled nucleotide or quencher-labeled nucleotide, a nucleotide monomer labeled with at least one immune-related substance selected from the group consisting of antigens, antibodies and anti-antibodies (immune-related, labeled nucleotide) is used. Describing based on an example, a fluorescent dye or quencher is bound on an antibody with which the nucleotide monomer is labeled. An antigen or anti-antibody corresponding to the above-described antibody is bound. As a result, the immune-related, labeled nucleotide acts in a similar manner as a fluorescence-labeled nucleotide or quencher-labeled nucleotide. To an antigen, an antibody with a fluorescent dye or quencher bound thereon binds. To an anti-antibody, an antibody with a fluorescent dye or quencher bound thereon binds. As a result, these immune-related, labeled nucleotides also act in a similar manner as a fluorescence-labeled nucleotide or quencher-labeled nucleotide.

To label a nucleotide with an immune-related substance, specifically with an immune-related substance selected from the group consisting of antigens, antibodies and anti-antibodies, the above-described, conventionally known method can be used to achieve the labeling. It is, however, more preferred to obtain it by relying upon custom synthesis services (NIHON GENE RESEARCH LABORATORIES, INC.; http://www.ngrl.co.jp) as described above.

Since this method is as described above, the immune-related, labeled nucleotide is paired with an immune-related substance corresponding to the immune-related substance in the immune-related, labeled nucleotide, the latter immune-related substance being labeled with the fluorescent dye or quencher. Even when a nucleotide is not labeled, the immune-related substance with which the immune-related, labeled nucleotide is labeled binds to the above-described immune-related substance to which the fluorescent dye or quencher is bound, so that a complex is formed as such a pair. This complex can be considered to have a structure with which the nucleotide is labeled. In the present invention, this complex is hence taken as being equivalent to a fluorescent dye or quencher for the sake of simplicity. The term "fluorescent dye" as used in the present invention is, therefore, defined to also embrace the complex, which contains the fluorescent dye, in addition to the fluorescent dye. Likewise, the term "quencher" as used in the present invention is defined to also embrace the complex, which contains the quencher, in addition to the quencher. A complex, that is, immune-related, labeled nucleotide, which contains a fluorescent dye, is included within the concept of a fluorescence-labeled nucleotide, and is also called "a fluorescence-labeled nucleotide". By applying a similar concept to a quencher, a nucleotide labeled with an immune-related substance, which contains the quencher, is called "a quencher-labeled nucleotide". Handling nucleic acid primers, which are labeled with immune-related substances, respectively, in a similar manner as the above-described nucleotide, a nucleic acid primer labeled with a fluorescent-dye-containing, immune-related substance is called "a fluorescence-labeled nucleic acid primer", and a nucleic acid primer labeled with a quencher-containing, immune-related substance is called "a quencher-labeled nucleic acid primer".

Therefore, the terms "immune-related, labeled nucleotide" and "immune-related, labeled nucleic acid primer" are defined such that the nucleotide and primer contain immune-related substances corresponding to the immune-related substances of the nucleotide and primer and carrying a fluorescent dye or quencher bound thereto. Specifically, the intensity of fluorescence from the nucleic acid polymerization system is measured by causing the nucleotide and/or primer and the immune-related substance, to which the fluorescent dye or quencher is bound, to exist together in the nucleic acid polymerization system.

In a similar manner as in the above-described invention methods A to F, the nucleic acid polymer or its template, or the template or the nucleic acid polymer synthesized by using the template as a template can be assayed. As appreciated from the foregoing, this method, including the methods to be described subsequently herein, corresponds to the present invention as defined in any one of the claims, and measures an increase or decrease in the intensity of fluorescence from the nucleic acid polymerization system.

As described above, a nucleotide is labeled with an antigen, antibody or anti-antibody, and in the course of a nucleic acid polymerization reaction, the nucleotide labeled with the antigen, antibody or anti-antibody is incorporated in a nucleic acid polymer such that any one of the substance-substance interactions described above in connection with the invention methods A to F, respectively, can take place. FIG. 8 illustrates the use of such an interaction between fluorescent dyes as described above in connection with the invention method A. Different from the conventional nucleic acid probe for homogeneous solution systems, said nucleic acid probe being to be described subsequently herein, it is not necessary to design a probe in such a manner that the intensity of fluorescence changes when hybridized to a template. This method, therefore, has an advantage in that the establishment of an experiment system is simple, easy and sure.

8) Invention Method H (No Diagrammatic Illustration)

This method corresponds to two aspects of the present invention.

i) This method is an illustrative method applicable when the nucleic acid polymerization system is the above-described nucleic acid polymerization system (3). This method is an assay method of a nucleic acid, which is characterized in that a nucleic acid polymerization reaction is conducted in a nucleic acid polymerization system, which contains a nucleic acid template, at least one dideoxynucleotide monomer labeled with at least one fluorescent dye and/or at least one quencher (the former being called "a fluorescence-labeled dideoxynucleotide" while the latter being called "a quencher-labeled dideoxynucleotide", and both of them being collectively called "labeled dideoxynucleotides"), and a nucleic acid-synthesizing enzyme, and the template nucleic acid or a nucleic acid polymer synthesized by using the template nucleic acid as a template is assayed from a change in fluorescence intensity or the amount of the change. The nucleic acid polymerization system contains at least one nucleotide selected from the group consisting of labeled nucleotides and unlabeled nucleotides. The nucleic acid polymerization system also contains an unlabeled nucleic acid primer.

ii) This method is an illustrative method applicable when the nucleic acid polymerization system is the above-described nucleic acid polymerization system (7). This method is an assay method of a nucleic acid, which is characterized in that a nucleic acid polymerization reaction is conducted in a nucleic acid polymerization system, which contains a nucleic acid template, at least one dideoxynucleotide monomer (will be called "an unlabeled dideoxynucleotide monomer"), a labeled nucleotide, an unlabeled nucleic acid primer, a nucleic-acid-specific fluorescent dye, and a nucleic acid-synthesizing enzyme, and the template nucleic acid or the nucleic acid polymer synthesized by using the template nucleic acid as a template is assayed from a change or the amount of the change. In the above method i) or ii) of the invention, the concepts of the fluorescent dye and quencher are similar to the those shown in the invention process G.

In combination with the single-base elongation reaction method, this method can suitably be used for the measurement, study or analysis of a polymorphism (including SNP) and/or mutation. Specifically, when a nucleic acid polymerization reaction or nucleic acid amplification reaction in the present invention is conducted using a nucleic acid primer, which has been designed such that the base at the 3' end of the nucleic acid primer is located adjacent to a base at the position of a target polymorphism (including SNP) and/or mutation in a template nucleic acid, and an unlabeled or labeled dideoxynucleotide having a base either complementary (capable of forming a hydrogen bond with) or non-complementary to the base at the position of the target polymorphism (including SNP) and/or mutation in the template nucleic acid, a difference in the intensity of fluorescence from the nucleic acid polymerization system arises depending upon whether or not the base at the position of the target polymorphism (including SNP) and/or mutation exists. Based on this difference, the objective can be achieved. This method is specifically described in Example 5 and Example 6.

Figure 9:
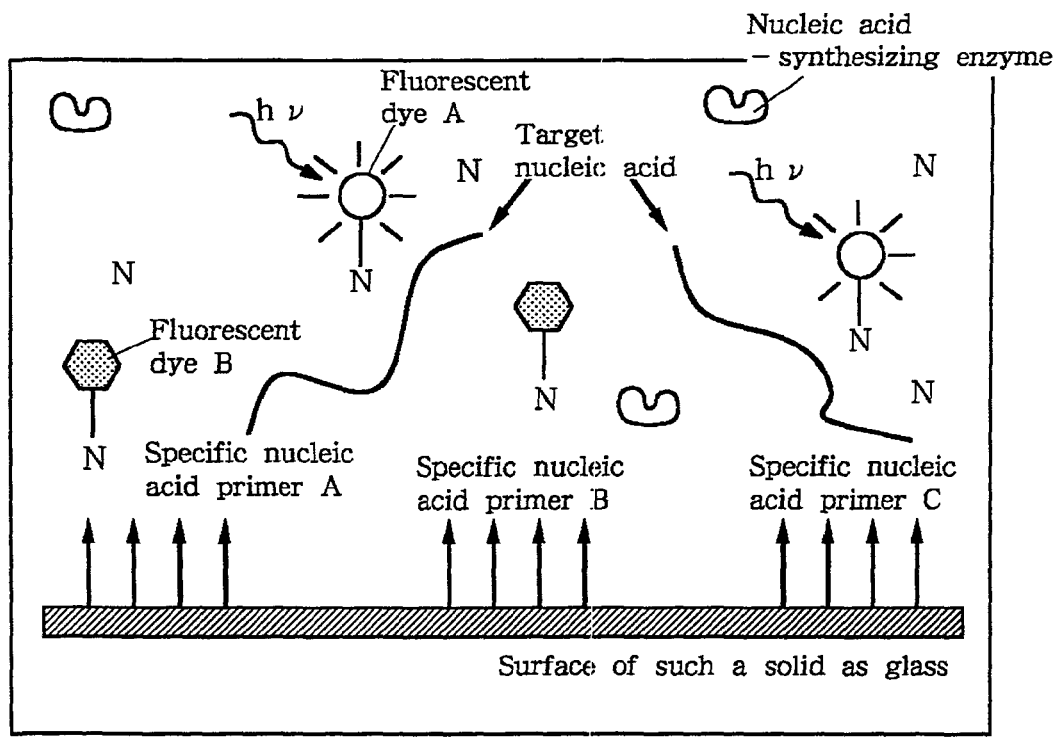
FIG. 9 illustrates an outline of the method H according to the present invention: a method of assaying a nucleic acid by making use of specific primers immobilized on a surface of a solid.
Figure 9:
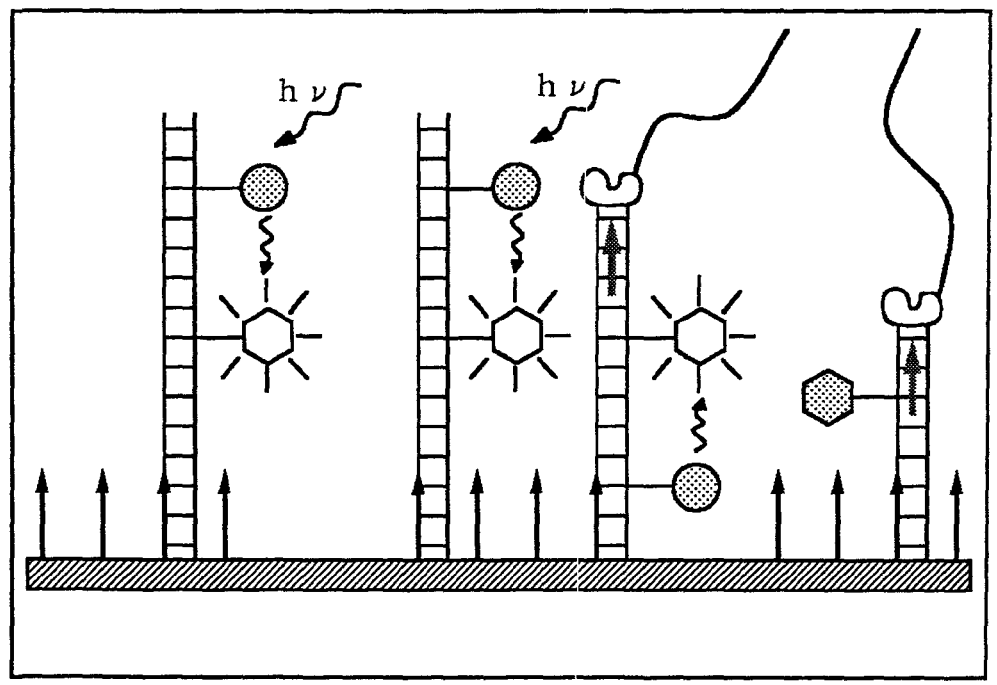

9) Invention Method I (See FIG. 9)

This method is similar to any one of the above-described invention methods A to G except that it is characterized by conducting the polymerization of a template nucleic acid from one or more nucleic acid primers, which are immobilized on a surface of a solid, with one of various nucleic acid-synthesizing enzyme s.

As described above, one or more nucleic acids are immobilized on a surface of a solid, and a polymerization reaction of a template nucleic acid is conducted with one of various nucleic acid-synthesizing enzyme s. Upon conducting the polymerization reaction, at least one of a nucleic acid primer, fluorescence-labeled nucleotide, a quencher-labeled nucleotide, a nucleic-acid-specific fluorescent dye and the like are provided such that the substance-substance interaction in any one of the above-described invention methods A to H takes place. By monitoring a change in fluorescence intensity, said change taking place upon occurrence of the interaction, or the amount of the change, the nucleic acid polymer alone or its template nucleic acid or the nucleic acid polymer synthesized by using the template nucleic acid as a template can be assayed (see FIG. 9; in the diagram, the interaction between the fluorescent dyes described above in connection with the invention method A is used).

When observed based on the single template nucleic acid or a single complex of the template nucleic acid and the newly-polymerized and synthesized nucleic acid polymer, the newly-polymerized and synthesize nucleic acid polymer contains plural fluorescent dyes as described above. This method is further improved in the sensitivity of an assay over the method that uses a nucleic acid probe for a homogeneous solution system and relies upon a change in the intensity of fluorescence from a single species of fluorescent dye. The sensitivity of an assay is considerably improved in this method, because this method is an assay method which is based on a change in fluorescence intensity due to a transfer of energy from the nucleic-acid-specific fluorescent dye, which has been incorporated in the complex between the template nucleic acid and the unlabeled or labeled nucleic acid primer or the newly-polymerized and synthesized nucleic acid polymer, to the fluorescent dye in the labeled nucleotide. Moreover, this method has another advantage in that it can assay one or more nucleic acids, including a target gene or the like, simply, easily and promptly.

In a method for the analysis of data obtained by the above-described method of the present invention, more preferred data can be obtained when the intensity of fluorescence from a fluorescent dye or nucleic-acid-specific fluorescent dye, which can play a role as a donor, in the FRET phenomenon of a nucleic acid polymerization system is divided by the intensity of fluorescence from another fluorescent dye capable of playing a role as an acceptor, or vice versa. This data processing method is also encompassed by the present invention.

The below-described, known nucleic acid probes (1) to (7) for homogeneous solution systems (oligonucleotides each of which hybridizes specifically to a template nucleic acid and is labeled with a fluorescent dye or quencher) and known nucleic acid assay methods can be preferably applied to the method of the present invention, especially to labeled nucleic acid primers. When used as such primers, they can be applied as described above. When used simply as the probes described in connection with the nucleic acid amplification method, it is preferred to use, as nucleic acid-synthesizing enzyme, an exonuclease-free DNA or RNA polymerase and a ligase. When a nucleic acid probe for a homogeneous solution system has hybridized to a template nucleic acid, it is indicated that the probe has been incorporated in the nucleic acid polymer in the present invention. If a DNA or RNA polymerase having exonuclease activity is used, however, the probe is degraded. After the degraded nucleotide is converted with kinase or the like into the triphosphate, the triphosphate is incorporated in the nucleic acid polymer in the present invention.

(1) Probes represented by the probe proposed by Morrison, et al. (Morrison et al., Anal. Biochem., 183, 231-244, 1989).
(2) Probes represented by the probe proposed by Mergney, et al. (Mergney et al., Nucleic Acid Res., 22, 920-928, 1994).
(3) Probes represented by the molecular beacon method (Tyagi et al., Nature Biotech., 14, 303-308, 1996; Schofield et al., Applied and Environ. Microbiol., 63, 1143-1147, 1997).
(4) Probes represented by the probe disclosed by Livak, et al. (U.S. Pat. No. 5,538,848).
(5) Probes represented by the probe proposed by Kurata, et al. (Kurata et al., Nucleic Acids Research, 2001, Vol. 29, No. 6, e34,). These probes are nucleic acid probes for homogeneous solution systems, in each of which a single-stranded oligonucleotide is labeled with a fluorescent dye. The base labeled with the fluorescent die is G or C, or there is G or C at a position 1 to 3 bases apart from a base in a target nucleic acid, said base corresponding to a labeled base and being counted as the $1^{st}$ base.
(6) Probes represented by the probe proposed by Davis et al. (Davis et al., Nucleic Acids Res., 24, 702-706, 1996).
(7) Probes represented by the probe proposed by Horn, et al. (U.S. Patent Application Publication No. US2001/0009760A1, Publn. Date: Jul. 26, 2001).

A description will hereinafter be made about the method of the present invention as applied to a nucleic acid amplification method instead of the above-described nucleic acid polymerization method. The expression "nucleic acid amplification method" as used in the present invention means a method for the in vitro amplification of a nucleic acid no matter whether it is known or unknown. The expression "nucleic acid amplification method" shall, therefore, be interpreted to include all nucleic acid amplification methods such as, for example, PCR, LCR (ligase chain reaction), TAS, ICAN (isothermal and chimeric primer-initiated amplification of nucleic acids), LAMP, NASRA, RCA, TAMA, and UCAN.

Further, the abbreviation "PCR" means various known PCR techniques. Examples shall include real-time monitoring quantitative PCR, RT-PCR, RNA-primed PCR, stretch PCR, reverse PCR, PCR making use of an Alu sequence, multiplex PCR, PCR making use of a mixed primer, PCR making use of PNA, and techniques for studying or analyzing melting curves on nucleic acids amplified by PCR.

Described specifically, the method of the present invention as applied to a nucleic acid amplification method is a method for assaying a nucleic acid by conducting a nucleic acid amplification reaction in the above-described nucleic acid polymerization system, especially in a system with a nucleic acid primer or nucleic acid probe contained therein under conventionally-known conditions (Kurata et al., Nucleic Acids Research, 2001, Vol. 29, No. 6, e34) while taking a hybridization reaction, a nucleic acid polymerization reaction (nucleic acid elongation reaction) and a denaturation reaction as 1 cycle, and then measuring a change in fluorescence intensity or relative fluorescence intensity or the amount of the change in each cycle successively to determine the concentration or copy number of a template nucleic acid before the nucleic acid amplification. By measuring the change in fluorescence intensity or the amount of the change in each cycle successively, it is possible to determine the number of cycles (Ct value) at which the change in fluorescence intensity or relative fluorescence intensity or the amount of the change begins to be observed (visually). From a relationship between concentrations or copy numbers of a standard template nucleic acid before the nucleic acid amplification and their corresponding Ct values, the concentration or copy number of the template nucleic acid in the sample before the nucleic acid amplification can be determined. The method of the present invention as applied to various nucleic acid amplifications will be described specifically in Examples 4 to 11.

The above-described nuclei acid probe for a homogeneous solution system can be suitably used as a nucleic acid primer (reverse and/or forward primer). In this case, an unlabeled nucleic acid primer obtained by removing the fluorescent dye and/or quencher from the nucleic acid probe for the homogeneous solution system can also be used suitably. As a nucleic acid polymer amplified by the nucleic acid amplification method contains at least one fluorescent dye, information available from a denaturation curve of the polymer by using at least one measurement wavelength is useful.

The nucleic acid amplification system useful in the present invention is any one of the nucleic acid polymerization systems (1) to (8), preferably (6), (7) and (8), more preferably (6) and (7).

The method according to the present invention also includes data processing methods to be described hereinafter. In the above-described method for analyzing the data obtained by the nucleic acid amplification method, preferred data can be obtained when the intensity of fluorescence from a nucleic acid polymerization system, which contains a template nucleic acid and/or nucleic acid-synthesizing enzyme, in each cycle is corrected by the intensity of fluorescence from a nucleic acid polymerization system, which does not contain any template nucleic acid and/or nucleic acid-synthesizing enzyme, in each corresponding cycle. Further, intensities of fluorescence from a fluorescent dye or nucleic-acid-specific fluorescent dye, which can play a role as a donor, in the FRET phenomenon of a nucleic acid polymerization system as measured successively may be divided by their corresponding intensities of fluorescence from a fluorescent dye, which can play a role as an acceptor, as measured successively or vice versa to correct the data. The thus-corrected data are useful as preferred data. It is to be noted that an electronic recording medium, on which a procedure including operational processing steps for such a correction (hereinafter called "correction processing steps") is recorded, is also embraced by the present invention. Needless to say, a measurement and/or data analysis system equipped with such an electronic recording medium as well as measurements making use of such a system shall all fall within the breadth of the present invention.

A specific description will hereinafter be made about a method for analyzing data obtained by real-time quantitative PCR which makes use of the nucleic acid polymerization reaction in the present invention. According to real-time quantitative PCR, data are measured in a real-time manner by a system which is now composed of a reactor for conducting PCR, an instrument for detecting fluorescence from a fluorescent dye, a user interface, namely, a computer-readable, recording medium with individual steps of a data analysis method recorded in the form of a program thereon (also called a "sequence detection software system"), and a computer for controlling them and analyzing data. It is also preferred to conduct the assay of the present invention by such a system.

The PCR reactor is an apparatus for repeatedly conducting a thermal denaturation reaction and annealing reaction of a template nucleic acid and an elongation reaction of a nucleic acid (for example, the temperature can be controlled to 95° C., 60° C. and 72° C. in cycles). The detection instrument is composed of a fluorescence-inducing argon laser, spectrograph and CCD camera. The computer-readable recording medium with the individual steps of the data analysis method recorded in the form of the program thereon is installed in the computer, is used to control the above-described system via the computer, and contains the program for analyzing or processing data outputted from the detection instrument.

The data analysis program recorded on the computer-readable recording medium comprises a step of measuring the intensity of fluorescence in each cycle, a step of displaying the thus-measured intensity of fluorescence as a function of its cycle, that is, a PCR amplification plot on a display of the computer, a step of calculating the cycle number of PCR (threshold cycle number: Ct) at which a change in fluorescence intensity or relative fluorescence intensity or the amount of the change begins to be detected, a step of preparing a calibration line to permit the determination of the copy number of a nucleic acid in a sample from a Ct value, and a step of printing data and plot values in each of the above steps. While PCR is exponentially proceeding, a linear relationship is established between the logarithmic values of copy numbers of a target nucleic acid at the time of the initiation of PCR and Ct values. By preparing a calibration line based on known copy numbers and detecting the Ct of a sample in which an unknown copy number of a template nucleic acid is contained, the initial copy number of the template nucleic acid at the time of the initiation of PCR can be calculated accordingly.

A description will hereinafter be made about a method for measuring or analyzing a polymorphism and/or mutation by using the method of the present invention. This method is a method for assaying a nucleic acid, which is characterized by conducting a nucleic acid polymerization reaction or nucleic acid amplification reaction in any one of the nucleic acid polymerization systems (1) to (9), preferably (6), (7) and (8), more preferably (6) and (7) for a nucleic acid polymerization method or nucleic acid amplification method, measuring a change in the intensity of fluorescence from the nucleic acid polymerization system or the amount of the change successively or non-successively, and assaying, studying or analyzing a polymorphism (including SNP) and/or mutation from the measurement value. It is preferred to combine the method with a sequence-specific extension method. This method will be described specifically in Example 7 to Example 10.

In this case, it is preferred to conduct the nucleic acid polymerization reaction or nucleic acid amplification reaction in a nucleic acid polymerization system containing at least one unlabeled or labeled nucleic acid primer prepared such that a base at the 3' end of the primer or the $2^{nd}$ base from the 3' end (said base at the 3' end being counted as the $1^{st}$ base) does not complement to the base of a target polymorphism (including SNP) and/or mutation in the template nucleic acid (both of the bases can form a hydrogen bond) although the remaining bases complement. When the nucleic acid polymerization reaction or nucleic acid amplification reaction does not proceed by using the primer as a precursor in the nucleic acid polymerization system in which the primer is contained, no change takes place in the intensity of fluorescence from the nucleic acid polymerization system. When the nucleic acid polymerization reaction or nucleic acid amplification reaction proceeds conversely, a change takes place in the intensity of fluorescence. In general, the reaction temperature may preferably be equal to of higher than the TM value of the primer, but lower than its denaturation reaction temperature (for example, 95° C.). By choosing a base, which does not complement to the base of the template nucleic acid, as the $3^{rd}$ base from the 3' end of the primer and forming an artificial mismatch between the template nucleic acid and the primer, any non-specific elongation reaction can be inhibited. In other words, it becomes possible to perform a more accurate determination of a polymorphism. The reaction temperature in this case may preferably range from a temperature about 5° C. lower than the TM value of the primer to a temperature lower than a denaturation reaction temperature. When a primer having a base, which does not complement to a base of a polymorphism or mutation in a template nucleic acid, is called "an A-type primer" in the present invention, the primer having a base which does complement shall be called "a B-type premier". The combined use of the A-type primer and the B-type primer in this assay method makes it possible to obtain surer data.

Specifically, the method can be carried out in the following manner.

In the following polymerization systems, a nucleic acid polymerization reaction or nucleic acid amplification reaction is conducted. A detailed description about this method will be made in Examples 7 and 8.

1) Any one of the above-described nucleic acid polymerization systems (1) to (8), preferably (6), (7) and (8), more preferably (6) and (7) for the nucleic acid polymerization method or nucleic acid amplification method. This nucleic acid polymerization system may preferably contain at least one A-type primer as a labeled or unlabeled nucleic acid primer.

2) The nucleic acid polymerization system described above under 1) contains at least one B-type primer as described above.

3) The nucleic acid polymerization system described above under 1) contains at least one A-type primer and at least one B-type primer as described above (with the proviso that an A-type primer and B-type primer labeled with the same fluorescent dye are excluded).

When an A-type primer and B-type primer labeled with the same fluorescent dye are used, a polymorphism (including SNP) or mutation can be assayed by conducting a nucleic acid polymerization reaction or nucleic acid amplification reaction in the reaction system 1) or 2), measuring a change in fluorescence intensity or the amount of the change successively or non-successively, and then comparing and studying the measurement values. When an A-type primer and B-type primer labeled with different fluorescent dyes are used, a nucleic acid polymerization reaction or nucleic acid amplification reaction can be suitably conducted in the reaction system 3). It is, however, to be noted that even in this case, a nucleic acid polymerization reaction or nucleic acid amplification reaction can also be conducted suitably in the reaction system 1) or 2).

As described above, the assay, study or analysis of a polymorphism (including SNP) and/or mutation is also feasible by using, instead of the above-described A-type primer or B-type primer, at least one unlabeled or labeled dideoxynucleotide having a base either complementary (capable of forming a hydrogen bond with) or non-complementary to the base in the target polymorphism (including SNP) and/or mutation in the template nucleic acid.

Therefore, the present invention also embraces reaction solutions and assay kits and devices for assaying, studying or analyzing polymorphisms (including SNP) and/or mutations, each of which is characterized by containing at least one A-type primer and/or at least one B-type primer as well as at least one substance selected from the group consisting of template nucleic acids, nucleic acid-synthesizing enzyme s, unlabeled nucleotides, labeled nucleotides, immune-related labeled nucleotides, labeled dideoxynucleotides and unlabeled dideoxynucleotides.

The assay method of the present invention for nucleic acids can be used in various fields such as medicine, legal medicine, anthropology, paleobiology, biology, genetic engineering, molecular biology, agriculture, and plant breeding. It can also be suitably applied to microorganism systems called "co-cultivation systems of microorganisms" or "symbiotic systems of microorganisms", in each of which various microorganisms exist together or at least one microorganism exists together with other animal- or plant-derived cells and they cannot be isolated from each other. Further, the present invention can also be suitably applied to various nucleic acid assay methods, for example, FISH, LCR, SD, and TAS.

The present invention can also include the following preferred embodiments:

[1] A method for assaying a nucleic acid, which is characterized by conducting a nucleic acid polymerization reaction in any one of the below-described nucleic acid polymerization systems, measuring a change in the intensity of fluorescence from the nucleic acid polymerization system or the amount of the change, and then assaying, studying or analyzing a polymorphism (including SNP) and/or a mutation from the measurement value.
  (1) A nucleic acid polymerization system containing a template nucleic acid, at least one labeled nucleotide, and a nucleic acid-synthesizing enzyme.
  (2) A nucleic acid polymerization system similar to the nucleic acid polymerization system (1) but additionally containing an unlabeled nucleotide.
  (3) A nucleic acid polymerization system containing at least one labeled dideoxynucleotide and a nucleic acid-synthesizing enzyme.
  (4) A nucleic acid polymerization system similar to the nucleic acid polymerization system (3) but additionally containing at least one nucleotide selected from the group consisting of labeled nucleotides and unlabeled nucleotides.
  (5) A nucleic acid polymerization system containing a template nucleic acid, unlabeled dideoxynucleotide, labeled nucleotide and nucleic acid-synthesizing enzyme.
  (6) A nucleic acid polymerization system similar to any one of the nucleic acid polymerization systems (1) to (5) but additionally containing a labeled nucleic acid primer or an unlabeled nucleic acid primer.
  (7) A nucleic acid polymerization system containing a template nucleic acid, unlabeled nucleotide, labeled nucleic acid primer, and nucleic acid-synthesizing enzyme.
  (8) A nucleic acid polymerization system similar to any one of the nucleic acid polymerization systems (1) to (7) but additionally containing a nucleic-acid-specific fluorescent dye.

[2] A method for assaying a nucleic acid, which is characterized by conducting, in any one of the below-described nucleic acid polymerization systems, a nucleic acid amplification reaction while taking a hybridization reaction (annealing reaction), a nucleic acid polymerization reaction (nucleic acid elongation reaction) and a denaturation reaction as 1 cycle, measuring a change in fluorescence intensity or the amount of the change in each cycle successively, and then determining the concentration or copy number of a template nucleic acid before the nucleic acid amplification.
  (1) A nucleic acid polymerization system containing a template nucleic acid, at least one labeled nucleotide, and a nucleic acid-synthesizing enzyme.
  (2) A nucleic acid polymerization system similar to the nucleic acid polymerization system (1) but additionally containing an unlabeled nucleotide.
  (3) A nucleic acid polymerization system containing at least one labeled dideoxynucleotide and a nucleic acid-synthesizing enzyme.
  (4) A nucleic acid polymerization system similar to the nucleic acid polymerization system (3) but additionally containing at least one nucleotide selected from the group consisting of labeled nucleotides and unlabeled nucleotides.
  (5) A nucleic acid polymerization system containing a template nucleic acid, unlabeled dideoxynucleotide, labeled nucleotide and nucleic acid-synthesizing enzyme.
  (6) A nucleic acid polymerization system similar to any one of the nucleic acid polymerization systems (1) to (5) but additionally containing a labeled nucleic acid primer or an unlabeled nucleic acid primer.
  (7) A nucleic acid polymerization system containing a template nucleic acid, unlabeled nucleotide, labeled nucleic acid primer, and nucleic acid-synthesizing enzyme.
  (8) A nucleic acid polymerization system similar to any one of the nucleic acid polymerization systems (1) to (7) but additionally containing a nucleic-acid-specific fluorescent dye.

[3] A method for assaying a nucleic acid as described above under [2], which comprises measuring a change in fluorescence intensity or the amount of the change in each cycle successively to determine the number of cycles (Ct value) at which the change in fluorescence intensity or the amount of the change begins to be observed, and then determining the concentration or copy number of a template nucleic acid before the nucleic acid amplification from a relationship between concentrations or copy numbers of the template nucleic acid before the nucleic acid amplification and their corresponding Ct values.

[4] A method for assaying a nucleic acid as described above under [2], which comprises conducting a nucleic acid amplification reaction in any one of the nucleic acid polymerization systems described above under [2], measuring a change in the intensity of fluorescence from the nucleic acid polymerization system or the amount of the change successively, and then assaying, studying or analyzing a polymorphism (containing SNP) and/or mutation from the measurement values.

[5] A method for assaying a nucleic acid as described above under [1] or [4], which comprises conducting a nucleic acid polymerization reaction or nucleic acid amplification reaction in a nucleic acid polymerization system, in which a base at the 3' end of an unlabeled or labeled nucleic acid primer or the second base from the 3' end (the base at the 3' end being counted as the $1^{st}$ base) contains an unlabeled or labeled nucleic acid primer corresponding to the base in a target polymorphism (including SNP) and/or mutation in a template nucleic acid, measuring a change in the intensity of fluorescence from the nucleic acid polymerization system or the amount of the change, and then assaying, studying or analyzing the polymorphism (including SNP) and/or mutation from the measurement value.

[6] A method for assaying a nucleic acid as described above under [1] or [4], which comprises conducting a nucleic acid polymerization reaction or nucleic acid amplification reaction in any one of the below-described nucleic acid polymerization systems, and then comparing and studying the resultant data to assay, study or analyze a polymorphism (including SNP) and/or a mutation.

1) A nucleic acid polymerization system similar to any one of the above-described nucleic acid polymerization systems (1) to (8) except that a base at the 3' end of an unlabeled or labeled nucleic acid primer or the second base from the 3' end (the base at the 3' end being courted as the $1^{st}$ base) contains at least one of primers (called "A-type primers") each having a base not complementary to the corresponding base in the template nucleic acid.

2) A nucleic acid polymerization system similar to the above-described nucleic acid polymerization system 1) except that a base at the 3' end of an unlabeled or labeled nucleic acid primer or the second base from the 3' end (the base at the 3' end being counted as the $1^{st}$ base) contains at least one of primers (called "B-type primers") each having a base complementary to the corresponding base in the template nucleic acid.

3) A nucleic acid polymerization system similar to the above-described nucleic acid polymerization system 1) except that at least one A-type primer and at least one B-type primer are contained (with the proviso that an A-type primer and B-type primer labeled with the same fluorescent dye are excluded).

[7] A method for processing or analyzing data obtained in the above-described method [1] and [3], which is characterized by dividing intensities of fluorescence from a fluorescent dye or nucleic-acid-specific fluorescent dye, which plays a role as a donor, in the FRET phenomenon of a nucleic acid polymerization system as measured successively or non-successively with the corresponding intensities of fluorescence from a fluorescent dye which plays a role as an acceptor in the FRET phenomenon of the nucleic acid polymerization system, or vice versa.

[8] A method for processing or analyzing data obtained in the above-described method [1] and [3], which is characterized by correcting the intensity of fluorescence from a nucleic acid polymerization system, which contains a template nucleic acid or nucleic acid-synthesizing enzyme, in each cycle with the intensity of fluorescence from a nucleic acid polymerization system, which does not contain any template nucleic acid or nucleic acid-synthesizing enzyme, in the corresponding cycle.

[9] A reaction solution or an assay kit or device for assaying, studying or analyzing a polymorphism (including SNP) and/ or a mutation, which is characterized by containing at least one A-type primer and/or at least one B-type primer as well as at least one substance selected from the group consisting of template nucleic acids, nucleic acid-synthesizing enzyme s, unlabeled nucleotides, labeled nucleotides, labeled dideoxynucleotides and unlabeled dideoxynucleotides.

[10] A method for assaying a nucleic acid as described in the above-described method [1] and [4], wherein the nucleic acid-synthesizing enzyme is Vent(exo-)DNA polymerase deficient in 3'→5' exonuclease activity (derived from *Thermococcus litoralis*), Tgo (exo-)DNA polymerase, "ThermoSequenase DNA Polymerase" (product of Amersham Biosciences Corp.), AmpliTagGold, or T7 Sequenase DNA polymerase.

[11] A method for assaying a nucleic acid as described above under [4], wherein the nucleic acid amplification method is PCR, ICAN, LAMP, NASBA, RCA, TAMA, or LCR.

[12] A method for assaying a nucleic acid as described above under [11], wherein PCR is real-time quantitative PCR.

[13] A device (DNA chip) characterized in that with a nucleic acid primer labeled with at least one labeled nucleic acid primer being immobilized on a surface of a solid, the method described in the above-described methods [1] and [2] can be conducted.

[14] A method for assaying a nucleic acid as described in the above-described methods [1] and [2], wherein the nucleic acid polymerization reaction of the template nucleic acid is conducted using the above-described device (DNA chip).

[15] An assay system capable of measuring fluorescence at varied temperatures to assay a template nucleic acid or a nucleic acid polymer or nucleic acid amplification product synthesized by using the template nucleic acid as a template in accordance with the method described in the above-described methods [1], [2] and [4], characterized by the incorporation of a computer-readable recording medium on which a procedure for allowing a computer to perform the steps of the data processing or analyzing method described in the above-described method [7] or [8] has been recorded as a program.

[16] A method for labeling a base at a desired position in a nucleic acid probe for a homogeneous solution system by using the method described in the above-described method [2].

EXAMPLES

The present invention will next be described more specifically based on examples and comparative examples, in which certain terms will be used in shortened or abbreviated forms as will be explained hereinafter.

1) A "template nucleic acid" may be referred to as a "template".

2) A "nucleic acid primer" will be referred to as a "primer".

3) "dNTSs", "dATP", "dGTP", "dTTP" and "dUTP" have the same meanings as they are currently used in molecular biology and the like.

The templates, labeled or unlabeled nucleotides, and labeled or unlabeled primers used in the examples were obtained by relying upon custom synthesis services (NIHON GENE RESEARCH LABORATORIES, INC.; http://www.ngrl.co.jp) unless otherwise specifically indicated.

The primers used in the examples and their base sequences are as will be described below. It is to be noted that in each base sequence, the right end is the 3' end while the left end is the 5' end.

(Base Sequences of Synthesized, Single-Stranded DNAs)
Primer 1: cagactcgac agtgtagacc cg
Primer 2: agagtttgat cctggctcag
Primer 3: ttgcatgtgt taggcctg On the other hand, Templates 1 to 9 had the following base sequences, respectively.

In each base sequence, the right side is the 3' side while the left side is the 5' side.

Template 1: acacacacac acacttcggg tctacactgt cgagtctg (SEQ ID NO: 4)

Template 2: tatctatcta tctatctatc tatctatctt cgggtctaca ctgtcgagtc tg (SEQ ID NO: 5)

Template 3: ttattcttat tcttattctt attcttattc ttattcttat tcttcgggtc tacactgtcg agtctg (SEQ ID NO: 6)

Template 4: ttatttcttt atttctttat ttctttattt cttttatttct ttatttcttt atttcttcgg gtctacactg tcgagtctg (SEQ ID NO: 7)

Template 5: ttattttctt tattttcttt attttctttta ttttctttat tttctttatt ttctttattt tcttcgggtc tacactgtcg agtctg (SEQ ID NO: 8)

Template 6: ttattttctt ttattttctt ttattttctt ttattttctt ttattttctt ttattttctt ttattttctt cgggtctaca ctgtcgagtc tg (SEQ ID NO: 9)

Template 7: ttattttttct tttattttttc tttattttttt cttttatttt tcttttatt ttctttattt ttctttattt ttcttcgg gtctacactg tcgagtctg (SEQ ID NO: 10)

Template 8: ttattttttct ttttattttt cttttattt ttctttttat ttttctttt atttttcttt ttattttttct ttttattttt cttcgggtct acactgtcga gtctg (SEQ ID NO: 11)

Template 9: ttatttttc ttttttatttt tttctttttt atttttttctt tttattttt tctttttat ttttcttttt ttattttatttt tttcttcggg tctacactgt cgagtctg (SEQ ID NO: 12)

Template 10: gcttcgggtc tacactgtcg agtctg (SEQ ID NO: 13)

Template 11: gctccgggtc tacactgtcg agtctg (SEQ ID NO: 14)

Example 1

Invention Method B(2)

Using the FRET phenomenon between a fluorescent dye specific to a double-stranded nucleic acid and a fluorescence-labeled nucleotide, each template nucleic acid was assayed.

(A) Various Methods

1) Synthesis of Template DNAs and Primers

Single-stranded DNAs (Templates 1 to 9), which were used as templates in this example, and a 22-base primer (Primer 1) were prepared by a DNA synthesizer, "ABI394" (manufactured by PerkinElmer Inc., U.S.A.). Templates 1 to 9 had on the 3' sides thereof a common sequence complementary to Primer 1. Those templates were each designed such that seven labeled dUTPs would be incorporated in the course of an elongation reaction. The combinations of the respective templates (i.e., the respective single-stranded DNAs) and Primer 1 have the following characteristics:

A combination of Template 1 and Primer 1: One fluorescence-labeled nucleotide is incorporated whenever one unlabeled nucleotide is incorporated.

A combination of Template 2 and Primer 1: One fluorescence-labeled nucleotide is incorporated whenever three unlabeled nucleotides are incorporated.

A combination of Template 3 and Primer 1: One fluorescence-labeled nucleotide is incorporated whenever five unlabeled nucleotides are incorporated.

A combination of Template 4 and Primer 1: One fluorescence-labeled nucleotide is incorporated whenever seven unlabeled nucleotides are incorporated.

A combination of Template 5 and Primer 1: One fluorescence-labeled nucleotide is incorporated whenever eight unlabeled nucleotides are incorporated.

A combination of Template 6 and Primer 1: One fluorescence-labeled nucleotide is incorporated whenever ten unlabeled nucleotides are incorporated.

A combination of Template 7 and Primer 1: One fluorescence-labeled nucleotide is incorporated whenever eleven unlabeled nucleotides are incorporated.

A combination of Template 8 and Primer 1: One fluorescence-labeled nucleotide is incorporated whenever thirteen unlabeled nucleotides are incorporated.

2) Polymerization (Amplification) Reaction Conditions

Used as a DNA polymerase was "VENT(EXO)DNA POLYMERASE" derived from Thermococcus litoralis and deficient in 3'→5' exonuclease activity (NEW ENGLAND BioLabs, Beverly, Mass.). Employed as fluorescence-labeled nucleotides, on the other hand, were Cyanine5-dUTP (650 nm/668 nm), LISSAMINE-5-dUTP (570 nm/588 nm) and TEXAS RED-5-dUTP (593 nm/612 nm) (the parenthesized values mean the maximum absorption wavelength/maximum fluorescence wavelength; Perkin Elmer Inc., U.S.A.). As a donor dye for inducing the FRET phenomenon on each labeled nucleotide incorporated by the DNA polymerase, was used "SYBR GREEN I NUCLEIC ACID GEL STRAIN" (Molecular Probes Corporation, U.S.A.) which binds specifically to a double-stranded nucleic acid, has a maximum excitation wavelength at 497 nm, and emits the maximum fluorescence around 520 nm A reaction solution was prepared as will be described below.

20 mM Tris-HCl (pH 8.8); 10 mM KCl; 10 mM $(NH_4)_2SO_4$;

2.5 mM $MgSO_4$; 0.1% Triton X-100; 0.25 mg/mL BSA;

200 nM dATP; 200 nM dGTP; 200 nM dCTP;

200 nM Cyanine5-dUTP, LISSAMINE-5-dUTP, or TEXAS RED(r)-5-dUTP; 1xSYBR GREEN I; 2 nM primer;

20 nM synthesized, single-stranded template DNA;

0.1 U (unit) VENT(EXO)DNA POLYMERASE.

The final volume of the reaction solution was 20 µL. The above reactant solutions were mixed into a homogeneous solution. Subsequent to thermal denaturation at 95° C. for 15 seconds, the solution was incubated at 65° C. for 15 minutes. LIGHTCYCLER SYSTEM" (Roche Diagnostics AG, Germany) was used for the detection of fluorescence. Upon conducting the detection, F1 (530 nm) in the system was used for the detection of SYBR GREEN I, F2 (640 nm) for the detection of LISSAMINE-5-dUTP or TEXAS RED-5-dUTP, and F3 (710 nm) for the detection of Cyanine5-dUTP. Further, the excitation intensity was fixed at 75%.

3) Details of used experiment systems

Models 1 to 9: Combinations of Primer 1 and Templates 1 to 9. Cyanine5-dUTP was used as a fluorescence-labeled nucleotide.

Model 10: A combination of Primer 1 and Template 9. As a fluorescence-labeled nucleotide, Cyanine5-dUTP was used, and VENT(EXO)DNA POLYMERASE was not added.

Models 11 to 19: Combinations of Primer 1 and Templates 1 to 9. As a fluorescence-labeled nucleotide, LISSAMINE-5-dUTP was used, and) VENT(EXO)DNA POLYMERASE was not added.

Model 20: A combination of Primer 1 and Template 9. As a fluorescence-labeled nucleotide, LISSAMINE-5-dUTP was used, and VENT(EXO)DNA POLYMERASE was not added.

Models 21 to 29: Combinations of Primer 1 and Templates 1 to 9. As a fluorescence-labeled nucleotide, TEXAS RED-5-dUTP was used.

Model 30: A combination of Primer 1 and Template 9. As a fluorescence-labeled nucleotide, TEXAS RED-5-dUTP was used, and VENT(EXO)DNA POLYMERASE was not added.

Models 31 to 39: Combinations of Primer 1 and Templates 1 to 9. No fluorescence-labeled nucleotide was used, and instead, dTTP was used.

Model 40: A combination of Primer 1 and Template 9. No fluorescence-labeled nucleotide was used, and instead, dTTP was used. VENT(EXO)DNA POLYMERASE was not added.

Figure 10:
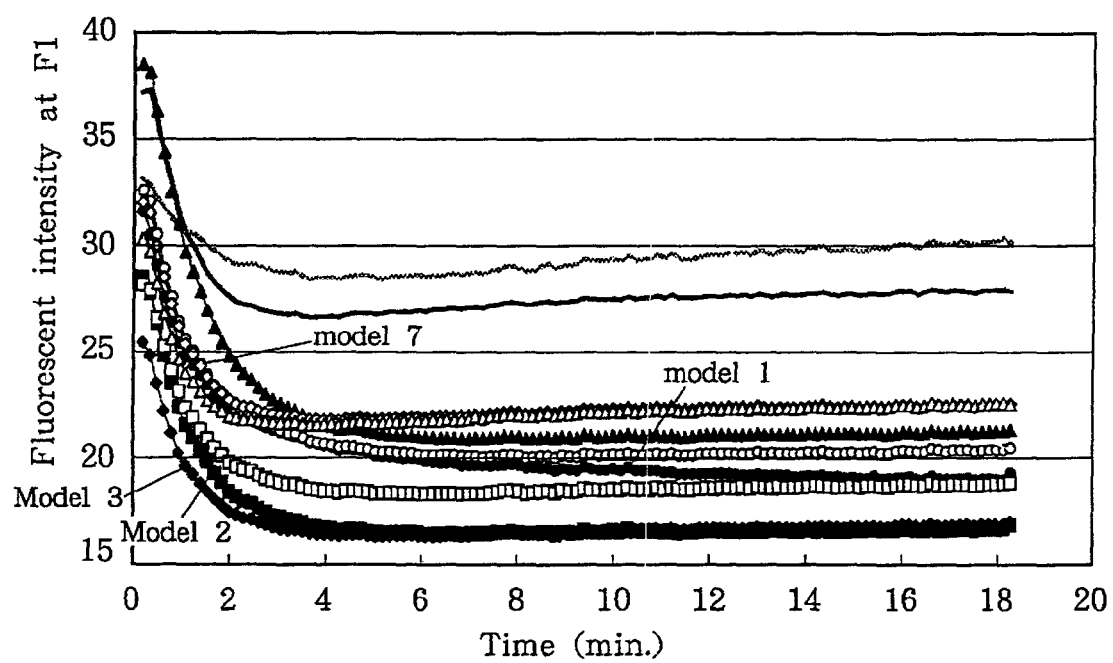
FIG. 10 illustrates an assay of a nucleic acid by making use of an interaction (FRET phenomenon) between fluorescent dye specific to a double-stranded nucleic acid (hereinafter referred to as "double-stranded-nucleic-acid-specific fluorescent dye") and a fluorescence-labeled nucleotide: changes in the fluorescence intensities at F1 of Models 1 to 10.

The results are shown in FIG. 10 to FIG. 16. Changes in the fluorescence intensities at F1 of Models 1 to 10 are shown in FIG. 10, and changes in the fluorescence intensities at F3 of Models 1 to 10 are shown in FIG. 11. Changes in the fluorescence intensities at F1 of Models 11 to 20 are shown in FIG. 12, and changes in the fluorescence intensities at F2 of Models 11 to 20 are shown in FIG. 13. Changes in the fluorescence intensities at F1 of Models 21 to 30 are shown in FIG. 14, and changes in the fluorescence intensities at F2 of Models 21 to 30 are shown in FIG. 15. Changes in the fluorescence intensities at F1 of Models 31 to 40 are shown in FIG. 16.

As a result, the fluorescence intensity at F1 decreased about 40% at the maximum in Models 1 to 9, while the fluorescence intensity at F3 increased about 4 times at the maximum in the same models. In the reaction of Model 10 in which no enzyme was added, no change was observed in the fluorescence intensity at F3 although the fluorescence intensity at F1 slightly decreased (FIG. 10, FIG. 11). In Models 11 to 19, the fluorescence intensity at F1 decreased about 40% at the maximum, while the fluorescence intensity at F2 increased about 2.5 times at the maximum. In Model 20 in which no enzyme was added, the fluorescence intensity at F2 did not change (FIG. 12, FIG. 13). In Models 21 to 29, the fluorescence intensity at F1 decreased about 40% at the maximum, while the fluorescence intensity at F2 increased about 8 times at the maximum. In Model 30 in which no enzyme was added, the fluorescence intensity at F2 did not change (FIG. 14, FIG. 15). In Models 31 to 39 in which SYBR(r)Green I alone was used, the fluorescence intensity at F1 increased 3 times at the maximum (FIG. 16).

As appreciated from the foregoing, the energy transfer phenomenon was observed between the fluorescent dye specific to double-stranded nucleic acids SYBR GREEN I in this example) and the corresponding fluorescence-labeled nucleotide, so that the corresponding template was successfully assayed. Described specifically, as a result of the supply of energy from the fluorescent dye, which is specific to double-stranded nucleic acids and served as a donor, the corresponding fluorescence nucleotide as an acceptor, the intensity of fluorescence (F1) from the donor decreased while the intensity of fluorescence (F2 or F3) increased. In the systems in which no enzyme was added, no change was observed in the intensity of fluorescence. In the system which contained only SYBR GREEN I without addition of any fluorescence-labeled nucleotide, no energy transfer took place so that only the intensity of fluorescence (F1) from SYBR GREEN I increased. This method made it possible to assay a template nucleic acid by measuring either a decrease in the intensity of fluorescence on the side of a donor or an increase in the intensity of fluorescence on the side of an acceptor in the energy transfer phenomenon.

Example 2

Invention Method A

Template nucleic acids were each assayed using the energy transfer phenomenon between its fluorescence-labeled nucleotides themselves.

1) Synthesis of Template DNAs and Primers

The primers and single-stranded DNAs employed in Example 1 were used. The combinations of the respective templates (i.e., the respective single-stranded DNAs) and Primer 1 have the following characteristics:

A combination of Template 1 and Primer 1: Fluorescence-labeled nucleotides and FITC-labeled nucleotides are alternately incorporated one by one.

A combination of Template 2 and Primer 1: Fluorescence-labeled nucleotides and FITC-labeled nucleotides are alternately incorporated one by one whenever one unlabeled nucleotide is incorporated.

A combination of Template 3 and Primer 1: Fluorescence-labeled nucleotides and FITC-labeled nucleotides are alternately incorporated one by one whenever two unlabeled nucleotides are incorporated.

A combination of Template 4 and Primer 1: Fluorescence-labeled nucleotides and FITC-labeled nucleotides are alternately incorporated one by one whenever three unlabeled nucleotides are incorporated.

A combination of Template 5 and Primer 1: After one FITC-labeled nucleotide is incorporated, three unlabeled nucleotides are incorporated. Next, one fluorescence-labeled nucleotide is incorporated, followed by the incorporation of four unlabeled nucleotides. These incorporations are repeated. In short, fluorescence-labeled nucleotides and FITC-labeled nucleotides are alternately incorporated one by one whenever four unlabeled nucleotides are incorporated.

A combination of Template 6 and Primer 1: Fluorescence-labeled nucleotides and FITC-labeled nucleotides are alternately incorporated one by one whenever four unlabeled nucleotides are incorporated.

A combination of Template 8 and Primer 1: Fluorescence-labeled nucleotides and FITC-labeled nucleotides are alternately incorporated one by one whenever five unlabeled nucleotides are incorporated.

A combination of Template 8 and Primer 1: Fluorescence-labeled nucleotides and FITC-labeled nucleotides are alternately incorporated one by one whenever six unlabeled nucleotides are incorporated.

2) Polymerization (Amplification) Reaction Conditions

As the fluorescence-labeled nucleotides, similar fluorescence-labeled nucleotides as in Example 1, specifically Cyanine5-dUTP, LISSAMINE-5-dUTP and TEXAS RED-5-dUTP were used. As the FITC-labeled nucleotide, FITC-dGTP (PerkinElmer Inc., U.S.A.) was used.

A reaction solution was prepared as will be described below.

20 mM Tris-HCl (pH 8.8); 10 mM KCl; 10 mM $(NH_4)_2SO_4$;

2.5 mM $MgSO_4$; 0.1% Triton X-100; 0.25 mg/mL BSA;

200 nM FITC-dGTP (donor dyes); 200 nM dCTP; 200 nM dATP;

200 nM Cyanine5-dUTP, LISSAMINE-5-dUTP, or TEXAS RED-5-dUTP (acceptor dye); 2 nM primer; 20 nM synthesized, single-stranded template DNA; 0.1 U (unit) VENT(EXO)DNA POLYMERASE.

The final volume of the reaction solution was 20 μL. The above reactant solutions were mixed into a homogeneous solution. Subsequent to thermal denaturation at 95° C. for 15 seconds, the solution was incubated at 65° C. for 15 minutes. "LIGHT CYCLER SYSTEM" was used for the detection of fluorescence. Upon conducting the detection, F1, F2 and F3 were used, and the excitation intensity was fixed at 75%.

3) Details of used experiment systems

Models 1 to 7: With the combinations of Primer 1 and Template 1, Primer 1 and Template 2, Primer 1 and Template 3, Primer 1 and Template 4, Primer 1 and Template 6, Primer 1 and Template 8, and Primer 1 and Template 9, Cyanine5-dUTP was used.

Model 8: Primer 1 and Template 6 were used, and as a fluorescence-labeled nucleotide, Cyanine5-dUTP was used. VENT(EXO)DNA POLYMERASE was not added.

Models 9 to 15: With the combinations of Primer 1 and Template 1, Primer 1 and Template 2, Primer 1 and Template 3, Primer 1 and Template 4, Primer 1 and Template 6, Primer 1 and Template 8, and Primer 1 and Template 9, LISSAMINE-5-dUTP was used.

Model 16: Primer 1 and Template 6 were used, and as a fluorescence-labeled nucleotide, LISSAMINE-5-dUTP was used. VENT(EXO)DNA POLYMERASE was not added.

Models 17 to 23: With the combinations of Primer 1 and Template 1, Primer 1 and Template 2, Primer 1 and Template 3, Primer 1 and Template 4, Primer 1 and Template 6, Primer 1 and Template 8, and Primer 1 and Template 9, TEXAS RED-5-dUTP was used. VENT (EXO) DNA POLYMERASE was not added.

The results are shown in FIG. 17 to FIG. 22. Changes in the fluorescence intensities at F1 of Models 1 to 8 are shown in FIG. 17, and changes in the fluorescence intensities at F3 of Models 1 to 8 are shown in FIG. 18. Changes in the fluorescence intensities at F1 of Models 9 to 16 are shown in FIG. 19, and changes in the fluorescence intensities at F2 of Models 9 to 16 are shown in FIG. 20. Changes in the fluorescence intensities at F1 of Models 17 to 24 are shown in FIG. 21, and changes in the fluorescence intensities at F2 of Models 17 to 24 are shown in FIG. 22.

As a result, the fluorescence intensity at F1 decreased about 50% at the maximum in Models 1 to 7, while the fluorescence intensity at F3 increased about 5 times at the maximum in the same models. In the reaction of Model 8 in which no enzyme was added, no change was observed in the fluorescence intensity (FIG. 17, FIG. 18). In Models 9 to 15, the fluorescence intensity at F1 decreased about 60% at the maximum, while the fluorescence intensity at F2 increased about 2.5 times at the maximum. In Model 16 in which no enzyme was added, the fluorescence intensity did not change (FIG. 19, FIG. 20). In Models 17 to 23, the fluorescence intensity at F1 decreased about 50% at the maximum, while the fluorescence intensity at F2 increased about 4.5 times at the maximum. In Model 24 in which no enzyme was added, the fluorescence intensity did not change (FIG. 21, FIG. 22).

As readily envisaged from the above results, the template nucleic acids were each successfully assayed based on a change in fluorescence intensity due to the energy transfer phenomenon between the fluorescence-labeled nucleotides synthesized by the DNA polymerase. Described specifically, the intensity of fluorescence (F1) from the FITC-labeled nucleotide as a donor dye decreased, while the intensity of fluorescence (at F2 or F3) from Cyanine5-, LISSAMINE- or TEXAS RED-labeled nucleotide as an acceptor fluorescent dye increased. In the systems in which no enzyme was added, no change was observed in fluorescence intensity. Similar to Example 1, it was possible to assay a template nucleic acid by measuring either a decrease in fluorescence intensity on the side of a donor fluorescent dye or an increase in fluorescence intensity on the side of an acceptor fluorescent dye. Therefore, the determination of the intensity of fluorescence from an acceptor fluorescent dye/the intensity of fluorescence from a donor fluorescent dye makes it possible to obtain a still higher S/N ratio. The invention method A has, therefore, been proven to be a high-sensitivity assay method for template nucleic acids.

Example 3

Invention Method A(2)

Real-time quantitative PCR making use of an FITC-labeled nucleotide and Cy5-labeled nucleotide 1) Synthesis of Template Employed as a template was a 1,400 bp DNA fragment obtained from *Pseudomonas fluorescens* DSM 50108 (RF) 16S ribosomal DNA. The template was prepared as will be described hereinafter. Using Primers 2 and 3, a PCR reaction was conducted with the PF genome as a template. After the resulting amplified fragment was purified by "MICROCON PCR(r)" (Millipore Corporation, U.S.A.), its concentration was measured and then converted into a corresponding copy number.

2) PCR Reaction Conditions

A reaction solution was prepared as will be described below. 20 mM Tris-HCl (pH 8.8); 10 mM KCl; 10 mM $(NH_4)_2SO_4$; 2.5 mM $MgSO_4$; 0.1% Triton X-100; 0.25 mg/mL BSA; 20 μM primer pair; template DNA having final concentrations of from $1 \times 10^9$ to $1 \times 10^5$ copies; 0.2 U VENT (EXO) DNA POLYMERASE; 6 μM dATP-dCTP-dGTP mixture; 2.5 μM dTTP; 0.25 μM Cy5 5-dUTP; 0.25 μM FITC-dUTP.

The final volume of the reaction solution was 20 μL. The above reactant solutions were combined into a homogeneous mixture. The reaction solution was thermally denatured at 95° C. for 30 seconds, and was then subjected to PCR 40 cycles each of which consisted of a denaturation reaction at 95° C. for 10 seconds, an annealing reaction at 56° C. for 10 seconds and an elongation reaction at 72° C. for 70 seconds. "LIGHT-CYCLER SYSTEM" was used for the detection of fluorescence. Upon conducting the detection, F1 and F3 were used. Further, the excitation intensity was fixed at 75%.

Under the above-described conditions, PCR was conducted, and the intensity of fluorescence in each cycle was actually measured. The results are plotted in FIG. 23 and FIG. 24. Specifically, with respect to the template ribosomal DNA of the respective copy numbers, the intensities of fluorescence during the annealing reactions in respective cycles were measured and plotted. It is observed that from the $6^{th}$ cycle or so, the intensity of fluorescence at F1 decreased while the intensity of fluorescence at F3 increased. It is also appreciated that the decrease in the intensity of fluorescence at F1 (the donor fluorescent dye) and the increase in the intensity of fluorescence at F3 (the acceptor fluorescent dye) takes place in the decreasing order of copy number. It is also observed that even in the blank of 0 copy as a result of no addition of the template DNA, the intensity of fluorescence at F1 progressively decreased as the cycle number increased. In this respect, the intensities of fluorescence from each sample were corrected. Specifically, the intensity of fluorescence at F1 from the sample in each cycle was divided by the intensity of fluorescence from the blank in the same cycle number.

$$Fn = fn(56° C.)/f'(56° C.)$$

where,
Fn: the corrected value of the fluorescence intensity in each cycle,
fn(56° C.): the intensity of fluorescence from the sample at 56° C. in each cycle, and
f'n(56° C.): the intensity of fluorescence from the blank at 56° C. in each cycle.

It is also appreciated that with concerning the individual copy numbers of the template ribosomal DNA, their fluorescence intensities in initial cycles are not the same. In this respect, the intensities of fluorescence from each sample were corrected. Specifically, assuming that the intensity of fluorescence in the $5^{th}$ cycle was 1, the intensity of fluorescence from each sample in each cycle was converted.

$$Cn = Fn(56° C.)/F5(56° C.)$$

where,
Cn: the converted value of the fluorescence intensity in each cycle,
Fn(56° C.): the intensity of fluorescence from the sample at 56° C. in each cycle, and
F5(56° C.): the intensity of fluorescence from the sample at 56° C. in the $5^{th}$ cycle.

The above-described two correction methods can each be applied to the fluorescence intensities either after the annealing (at 56° C. in the above-described methods) or after the elongation reaction (at 72° C.).

In accordance with the processing method, the intensity of florescence in each cycle was converted assuming that the intensity of fluorescence in the $5^{th}$ cycle was 1. The converted values were plotted against the corresponding cycle numbers. The data processed in the above-described manner are shown in FIG. 25 and FIG. 26. A threshold value was set. Cycle numbers reached the threshold value were plotted along the X-axis, copy numbers of the template ribosomal DNA before the initiation of the reaction were plotted along the Y-axis, and then, a calibration line was drawn. Actually, the threshold value was set at 0.85 when the Y-axis represents florescence intensities at F1, and the threshold value was set at 1.5 when the Y-axis represents fluorescence intensities at F3. Coefficients of correlation (R2) determined through the above-described processing were 0.9965 (FIG. 27) and 0.9931 (FIG. 28), respectively.

When PCR is performed using, as a substrate, dNTP with two kinds of fluorescence-labeled nucleotides contained therein, the resulting product is labeled by the two kinds of fluorescence-labeled nucleotides under the action of DNA polymerase. Relying upon this property, real-time quantitative PCR was performed using the energy transfer phenomenon between the two kinds of fluorescence-labeled nucleotides themselves labeled in the same molecule. Comparing the fluorescent intensity in the initial phase with that in the Plateau phase, the intensity of fluorescence (at F1 in this case) from the donor decreased about 50%, while the intensity of fluorescence (at F3 in this case) from the acceptor increased to about 3 times. Using those fluorescence intensities, corrections were made on quenching of the fluorescence dye and a difference of fluorescence intensity in the initial phase, both of which took place as a result of the performance of PCR in cycles. Those corrections made it possible to perform an accurate quantitation of the template nucleic acid. According to this method, the quantitation was feasible no matter which one of the donor and acceptor was chosen for the measurement of a change in fluorescence intensity. By dividing the fluorescence intensity at F3 with that at F1, it is also possible to improve the S/N ratio.

Example 4

Real-Time Quantitative PCR Making Use of a Fluorescent Dye Specific to a Double-Stranded Nucleic Acid and Cy5-Labeled Nucleotide A template and primers similar to those employed in Example 5 were used. The composition of a reaction solution will be shown below.
20 mM Tris-HCl (pH 8.8); 10 mM KCl; 10 mM $(NH_4)_2SO_4$; 2.5 mM $MgSO_4$; 0.1% Triton X-100; 0.25 mg/mL BSA; 20 µM primer pair.

The final volume of the reaction solution was 20 µL. The above reactant solutions were combined into a homogeneous mixture. The reaction solution was thermally denatured at 95° C. for 30 seconds, and was then subjected to PCR 40 cycles each of which consisted of a denaturation reaction at 95° C. for 10 seconds, an annealing reaction at 56° C. for 10 seconds and an elongation reaction at 72° C. for 70 seconds. "LIGHT-CYCLER SYSTEM" was used for the detection of fluorescence. Upon conducting the detection, F3 was used. Further, the excitation intensity was fixed at 75%. The results are shown in FIG. 29. In a similar manner as in Example 5, the fluorescence intensities were corrected. When the threshold value was set at 2, the coefficient of correlation (R2) was 0.9984 (FIG. 30).

When PCR is performed using, as a substrate, dNTP with one kind of fluorescence-labeled nucleotide contained therein, the resulting product is labeled by the one kind of fluorescence-labeled nucleotide under the action of DNA polymerase. Here, a fluorescent dye which binds to a certain kinds of template nucleic acids was mixed in advance, and real-time quantitative PCR was performed using the energy transfer phenomenon between the fluorescent dye and the fluorescence-labeled nucleotide in the molecule. Comparing the fluorescent intensity in the initial phase with that in the Plateau phase, the intensity of fluorescence from the acceptor was found to increase to about 4 times. Using those fluorescence intensities, corrections were made on quenching of the fluorescence dye and a difference of fluorescence intensity in the initial phase, both of which took place as a result of the performance of PCR in cycles. Those corrections made it possible to perform a measurement (quantitation) of the template nucleic acid.

Example 5

Assay of SNP by single-base elongation reaction making use of a labeled nucleotide 26-Base, single-stranded DNAs (templates 10 and 11) employed as a template in this example were prepared by a DNA synthesizer, "AB1394". Templates 10 and 11 contained T and C, respectively, as the fourth base as counted from the 5' end, and their remaining sequences were the same. Templates 10 and 11 can, therefore, be considered to be DNA fragments containing SNPs (single nucleotide polymorphism; hereinafter abbreviated as "SNP") which are T and C, respectively, at particular positions. Those templates were each designed such that it contained on its 3' side a base sequence complementary to Primer 1 and, when hybridized to the primer, the base at the 3' end of the primer would be located adjacent to the base at the SNP position of the template. As the fluorescence-labeled nucleotides, "TEXAS RED-5-ddATP" (PerkinElmer Inc., U.S.A.) and "CY5-5-ddGTP" (Amersham Biosciences Corp.) were used. Further, SYBR GREEN I was added to the nucleic acid polymerization system.

2) Single-base Elongation Reaction

A reaction solution was prepared as will be described below.
20 mM Tris-HCl(pH 8.8); 10 mM KCl; 10 mM $(NH_4)_2SO_4$; 2.5 mM $MgSO_4$; 0.1% Triton X-100; 0.25 mg/mL BSA; 200 nM TEXAS RED-5-ddATP; 200 nM CYANINNE5-5-ddGTP; 1×SYBR(r)Green I; 20 nM primer; 200 nM synthesized, single-stranded template DNA; 0.1 U VENT(EXO) DNA POLYMERASE.

The final volume of the reaction solution was 20 μL. The above reactant solutions were combined into a homogeneous mixture. The reaction solution was thermally denatured at 95° C. for 15 seconds, and was then incubated at 65° C. for 10 minutes. A fluorometer, "PERKINELMER LS-50B", was used for the detection of fluorescence. Measurements were conducted at 480 nm excitation wavelength and 610 nm and 670 nm fluorescence wavelengths. The slit width was set at 10 nm.

3) Details of Used Experiment Systems
Model 1: A combination of Primer 1 and Template 10, without addition of VENT(EXO) DNA POLYMERASE (Blank Control).
Model 2: A combination of Primer 1 and Template 10 (a homozygote of Template 10), with addition of VENT (EXO)DNA POLYMERASE.
Model 3: A combination of Primer 1 and Template 11 (a homozygote of Template 11), with addition of VENT (EXO)DNA POLYMERASE.
Model 4: A combination of Primer 1 and a 1:1 (100 nm, each) mixture of Templates 10 and 11 (a heterozygote of Templates 10 and 11), with addition of VENT(EXO) DNA POLYMERASE.

As a result, the intensity of fluorescence at 610 nm from Model 1 was 0.60, and the intensity of fluoresense at 670 nm from Model 1 was 0.10. The intensity of fluorescence at 610 nm from Model 2 was 2.40, and the intensity of fluorescence at 670 nm from Model 2 was 0.10. The intensity of fluoresecence at 610 nm from Model 3 was 0.59, and the intensity of fluorescence at 670 nm from Model 3 was 0.31. The intensity of fluorescence at 610 nm from Model 4 was 2.01, and the intensity of fluorescence at 670 nm from Model 4 was 0.21.

Model 2 which assumed a homozygote of Template 10 had an intensity of fluorescence at 610 nm about 4 times as high as the blank. It is presumed that as a result of the incorporation of the complementary TEXAS RED-labeled nucleotide to the SNP position of Template 10, an energy transfer took place with respect to SYBR GREEN I and the intensity of fluorescence at 610 nm from TEXAS RED increased. As the non-complementary CY5-labeled nucleotide is not incorporated to the SNP position, the intensity of fluorescence at 670 nm remained unchanged. Model 3 which assumed a homozygote of Template 11 had an intensity of fluorescence at 670 nm about 3 times as high as the blank. It is presumed that as a result of the incorporation of the complementary CY5-labeled nucleotide to the SNP position of Template 11, an energy transfer took place with respect to SYBR GREEN I and the intensity of fluorescence at 670 nm from CY5 increased. As the non-complementary TEXAS RED-labeled nucleotide is not incorporated to the SNP position, the intensity of fluorescence at 610 nm remained unchanged. With Model 4 of the heterozygotic system that Template 10 and Template 11 were included at 1:1, the intensity of fluorescence increased about two times at both 610 nm and 670 nm. Those increases took place as a result of the incorporation of both of the TEXAS RED-labeled nucleotide and CY5-labeled nucleotide. Even when two fluorescence-labeled nucleotides are incorporated per molecule as in the case of the measurement of SNP, it is also possible to measure a change in fluorescence intensity as described above. Further, the use of two kinds of fluorescence-labeled nucleotides makes it possible to assay two kinds of template nucleic acids within a single tube.

Example 6

Detection of a Single-base Polymorphism at the 282-bp Fragment of p53 Gene Codon by a Single-base Elongation Reaction (1) Synthesis of Template DNAs and Primers Using Primers 14 and 15, DNAs for use as templates in this example were prepared by PCR reaction.

(PCR Reaction Conditions)

A reaction solution was prepared as will be described below. 20 mM Tris-HCl(pH 8.0); 10 mM KCl; 10 mM $(NH_4)_2SO_4$; 2.5 mM $MgCl_2$; 0.1% Triton X-100; 200 nm primer pair; 50 ng human genome DNA; 1U AMPLI-TAQGOLD (Applied Biosystems); 200 μM dNTPs.

The final volume of the reaction solution was 25 μL. The above reactant solutions were combined into a homogeneous mixture. The reaction solution was thermally denatured at 95° C. for 10 minutes, and was then subjected to PCR 40 cycles each of which consisted of a denaturation reaction at 95° C. for 30 seconds, an annealing reaction at 60° C. for 30 seconds and an elongation reaction at 72° C. for 30 seconds.

(2) Purification of PCR Product

Since the PCR primer and dNTP were each contained in a large excess in the thus-prepared PCR product, the PCT product was purified by a "Quiagen PCR Product Purification Kit". As an alternative, shrimp alkaline phosphatase (usb) and exonuclease I (usb) were added in amounts of 4 U and 20 U, respectively to the PCR product, and subsequent incubation at 37° C. for 90 minutes, the resulting mixture was heated at 85° C. for 15 minutes to inactivate the enzymes. The purified or enzymatically-treated solution was provided as a template.

(3) Single-Base Elongation Reaction

As a genotyping primer, the oligonucleotide described above with respect to Primer 16 was used. The oligonucleotide had been designed such that, when hybridized to the template prepared by the PCR reaction, the base at its 3' end would be located adjacent to the SNP position.

A reaction solution was prepared as will be described below. 1 U THERMO SEQUENASE I DNA POLYMERASE (Amersham-Pharmacia Biotech); 10× THERMO SEQUENCE I DNA POLYMERASE buffer; 200 nM TEXAS RED-5-ddATP; 200 nM Cy5-5-ddGTP; 1×SYBR GREEN I; 200 nM primer; template DNA.

The final volume of the reaction solution was 20 μL. The above reactant solutions were combined into a homogeneous mixture. The reaction solution was thermally denatured at 95° C. for 30 seconds, and was then incubated at 50° C. for 1 minute. Taking those steps as 1 cycle, PCR was conducted 40 cycles. A fluorometer, "LS-50B" (PerkinElmer Inc.), was used for the detection of fluorescence. Measurements were conducted at 480 nm excitation wavelength and 610 nm and 670 nm fluorescence wavelengths. The slit width was set at 10 nm.

As a result, the intensity of fluorescence at 610 nm from the C-allele homozygote was 0.60, and the intensity of fluorescence at 670 nm from the C-allele homozygote was 2.10. The intensity of fluorescence at 610 nm from the T-allele homozygote was 2.40, and the intensity of fluorescence at 670 nm from the T-allele homozygote was 0.58. The intensity of fluorescence at 610 nm from the heterozygote was 1.60, and the intensity of fluorescence at 670 nm from the heterozygote was 1.23. The intensity of fluorescence at 610 nm in a blank test conducted without addition of any template DNA was 0.61, and the intensity of fluorescence at 670 nm in the blank test was 0.60. It is to be noted that the samples used in this example were those determined beforehand to be of the genotype by another method (a restriction fragment length polymorphism method).

The C-allele homozygote had an intensity of fluorescence at 670 nm about 5 times as high as the blank. It is presumed that as a result of the incorporation of the CY5-labeled nucleotide, an energy transfer took place with respect to SYBR GREEN I and the intensity of fluorescence at 670 nm from CY5 increased. As the non-complementary Texas-Red-labeled nucleotide is not incorporated to the SNP position, the intensity of fluorescence at 610 nm remained unchanged. When the T-allele homozygote was used as a template, the intensity of fluorescence at 610 nm was about 4 times as high as the blank. It is presumed that as a result of the incorporation of the complementary TEXAS RED-labeled nucleotide to the SNP position, an energy transfer took place with respect to SYBR GREEN I and the intensity of fluorescence at 610 nm from TEXAS RED increased. The non-complementary CY5-labeled nucleotide was not incorporated to the SNP position so that the intensity of fluorescence at 670 nm remained unchanged. With the heterozygote, the intensity of fluorescence increased about two times at both 610 nm and 670 nm. Those increases took place as a result of the incorporation of both of the TEXAS RED labeled nucleotide and CY5-labeled nucleotide. Even when a PCR product is used as a template as described above, it is also possible to detect two kinds of nucleic acids within a single tube by using the method of the present invention.

Example 7

Detection of a Single-base Polymorphism in Aldehyde Dehydrogenase 2 (ALDH2) Gene by a Sequence-specific Elongation Method Making Use of an Allele-specific Primer ALDH2 is one of the genes associated with alcohol metabolism, and is located on the long arm of chromosome 12. The mutation allele (ALDH2*2) frequently found on Japanese is a point mutation in that GAA, which encodes the $487^{th}$ amino acid, Glu (glutamic acid), in ALDH2 exon 12 has changed to AAA which encodes Lys (lysine).

(1) Synthesis of a Template

Using Primers 4 and 5, a template DNA for use in this example was prepared by PCR reaction from a human genome DNA. A reaction solution had the following composition.

20 mM Tris-HCl (pH 8.0); 10 mM KCl; 10 mM $(NH_4)_2SO_4$; 2.5 mM $MgCl_2$; 0.1% Triton X-100; 200 nm primer pair; 50 ng human genome DNA; 1 U AmpliTaqGold; 200 µM dNTPs mixture.

The final volume of the reaction solution was 25 µL. The above reactant solutions were combined into a homogeneous mixture. The reaction solution was thermally denatured at 95° C. for 10 minutes, and was then subjected to PCR 40 cycles each of which consisted of a denaturation reaction at 95° C. for 30 seconds, an annealing reaction at 60° C. for 30 seconds and an elongation reaction at 72° C. for 30 seconds.

(2) Purification of PCR Product

The thus-prepared PCT product was purified by a PCR product purification kit (Quiagen), or subjected to enzymatic treatment (shrimp alkaline phosphatase and exonuclease I were added in amounts of 4 U and 20 U, respectively to the PCR product, and subsequent incubation at 37° C. for 90 minutes, the resulting mixture was heated at 85° C. for 15 minutes to inactivate the enzymes. The purified or enzymatically-treated solution was provided as a template for use in an analysis of a single-base polymorphism.

(3) Sequence-Specific Elongation Reaction

Synthesized were allele-specific primers the 3' ends of which were complementary to their SNPs. Primer 3 was C-allelic at the 3' end, while Primer 7 was T-allelic at the 3' end. Except for these 3' ends, these primers had the same sequence which was complementary to the template. An analysis of a single-base polymorphism by a sequence-specific elongation reaction is based on the principle that an elongation reaction by a DNA polymerase is inhibited if any mismatch exists at the 3' end of a primer. When the 3' ends are complementary, FRET takes place by the two kinds of fluorescent-dye-labeled nucleotides incorporated by an elongation reaction so that the intensity of fluorescence changes. When the 3' ends are not complementary, no fluorescence-labeled nucleotide is incorporated so that the intensity of fluorescence remains unchanged.

A reaction solution was prepared as will be described below.

20 mM Tris-HCl (pH 8.8); 10 mM KCl; 10 mM $(NH_4)_2SO_4$; 2.5 mM $MgSO_4$; 2 µM dATP; 2 µM dTTP; 1.2 µM dCTP; 400 nM CY5-5-dCTP; 400 nm FITC-5-dCTP; 200 nM primer; purified PCT product.

The final volume of the reaction solution was 20 µL. The above reactant solutions were combined into a homogeneous mixture. The reaction solution was thermally denatured at 95° C. for 15 seconds, and was then subjected to PCR 20 cycles each of which consisted of an annealing reaction at 60° C. for 1 minute and an elongation reaction at 72° C. for 20 seconds. "LIGHTCYCLER SYSTEM" was used for the detection of fluorescence. Upon conducting the detection, F1 (530 nm) and F3 (710 nm) which the system was equipped with were used for the detection of FITC and CY5, respectively. Further, the excitation intensity was fixed at 75%.

Changes in the intensities of fluorescence from FITC and CY5 upon use of Primer 6 in the three kinds of gene forms (C-allele homozygote, T-allele homozygote, and heterozygote) are shown in FIG. 31 and FIG. 32, respectively. Changes of the intensities of fluorescence from FITC and CY5 upon use of Primer 7 are shown in FIG. 33 and FIG. 34, respectively. In the case of the C-allele homozygote, the fluorescence intensity changed only when Primer 6 the 3' end of which was C-allelic was added. Specifically, the intensity of fluorescence from FITC as a donor decreased, while the intensity of fluorescence from CY5 as an acceptor increased. When Primer 7 the 3' end of which was T-allelic was added, no change in the fluorescence intensity was observed. It is presumed that an elongation reaction took place only when Primer 6 the 3' end of which was complementary to the template was added. In the case of the T-allele homozygote, only when Primer 7 the 3' end of which was T-allelic was added, the intensity of fluorescence from FITC decreased and the intensity of fluorescence from CY5 as the acceptor increased. In the case of the heterozygote, on the other hand, a change in fluorescence intensity was observed no matter which one of Primer 6 and Primer 7 was added. It is to be noted that the samples used in this example were those determined beforehand to be of the genotype by another method (a restriction fragment length polymorphism method). It has, therefore, been demonstrated that a combination of the method of the present invention with the sequence-specific elongation method permits an analysis of a single-base polymorphism.

Example 8

Detection of a Single-base Polymorphism in ALDH2 Gene by a Sequence-specific Elongation Method Making use of a Template Prepared by the ICAN Method (Isothermal and Chimeric Primer-initiated Amplification of Nucleic Acids)

A template DNA for use in this example was prepared by an isothermal gene amplification method, which made use of an RNA-DNA chimeric primer, a DNA polymerase having strand displacement activity and template exchange activity, and RNaseH. The primer used upon preparation of the template DNA had the same base sequence as Primers 4 and 5, and the three bases at its 3' end had been replaced by a ribonucleotide.

(1) Synthesis of a Template DNA (ICAN reaction conditions)
 35 mM Tris-HCl(pH 7.8); 10 mM $MgSO_4$; 5% DMSO; 1 μM primer pair; 200 ng human genome DNA; 2.2U "BCABEST DNA POLYMERASE" (TAKARA SHUZO CO., LTD.); 15U RNASE H (TAKARA SHUZO CO., LTD.); 1 mM dNTPs.
 The final volume of the reaction solution was 20 μL. The above reactant solutions were combined into a homogeneous mixture. The reaction solution was reacted at 55° C. for 60 minutes, and was then heated at 90° C. for 5 minutes to inactivate the enzymes.

(2) Enzymatic Treatment of ICAN Amplification Product
 Shrimp alkaline phosphatase and exonuclease I were added in amounts of 4 U and 20 U, respectively to the ICAN amplification product, and subsequent incubation at 37° C. for 90 minutes, the resulting mixture was heated at 85° C. for 15 minutes to inactivate the enzymes.

(3) Sequence-specific Elongation Reaction
 A reaction solution was prepared as will be described below.
 20 mM Tris-HCl(pH 8.8); 10 mM KCl; 10 mM $(NH^4)_2SO_4$; 2.5 mM $MgSO_4$; 2 μM dATP; 2 μM dGTP; 2 μM dTTP; 1.2 μM dCTP; 400 nM CY5-5-dCTP; 400 nm FITC-5-dCTP; 100 nM Primers 6 and 7; ICAN amplification product; 0.1 U VENT(EXO)DNA POLYMERASE.
 As a result, in the case of the C-allele homozygote, the fluorescence intensity changed only when Primer 6 the 3' end of which was C-allelic was added. Specifically, the intensity of fluorescence from FITC as a donor in the FRET phenomenon decreased, while the intensity of fluorescence from CY5 as an acceptor increased. When Primer 7 the 3' end of which was T-allelic was added, no change was observed. In the case of the T-allele homozygote, only when Primer 7 the 3' end of which was T-allelic was added, the intensity of fluorescence changed. In the case of the heterozygote, on the other hand, a change in fluorescence intensity was observed no matter which one of Primer 6 and Primer 7 was added. It has, therefore, been confirmed that the detection of a single-base polymorphism is feasible even when an ICAN amplification product is used as a template.

Example 9

Detection of a Single-base Polymorphism in a Prostate-specific Antigen by a Sequence-specific Elongation Method Making Use of a Template Prepared by an LAMP (Loop-Mediated Isothermal Amplification) Method A template DNA for use in this example was prepared by an isothermal gene amplification method making use of four primers and also, a strand-displacing DNA polymerase as an enzyme.

(1) Synthesis of a Template DNA
LAMP Reaction Conditions
 10× Thermopol Buffer (NEB); 2 mM $MgSO_4$; 200 ng human genome DNA; 8 U Bst DNA polymerase; 4 M betaine (Sigma Chemicals Company); 10 mM dNTPs; 40 pmol Primer 8; 40 pmol Primer 9; 5 pmol Primer 10; 5 pmol Primer 11.
 The final volume of the reaction solution was 25 μL. The above reactant solutions were combined into a homogeneous mixture. The reaction solution was reacted at 65° C. for 60 minutes, and was then heated at 80° C. (for 10 minutes to inactivate the enzymes.

(2) Enzymatic Treatment of LAMP Amplification Product
 Shrimp alkaline phosphatase and exonuclease I were added in amounts of 4 U and 20 U, respectively to the LAMP amplification product, and subsequent incubation at 37° C. for 90 minutes, the resulting mixture was heated at 85° C. for 15 minutes to inactivate the enzymes.

(3) Sequence-specific elongation reaction
 A reaction solution was prepared as will be described below.
 20 mM Tris-HCl(pH 8.8); 10 mM KCl; 10 mM $(NH_4)_2SO_4$; 2.5 mM $MgSO_4$; 400 nM CY5-5-dCTP; 400 nm FITC-5-dCTP; 2 μM dATP; 2 μM dGTP; 2 μM dTTP; 1.2 μM dCTP; 100 nM Primer 12 and Primer 13; LAMP amplification product; 0.1 U VENT(EXO)DNA POLYMERASE.
 The final volume of the reaction solution was 20 μL. The above reactant solutions were combined into a homogeneous mixture. The reaction solution was thermally denatured at 95° C. for 15 seconds, and was then subjected to a PCR reaction 20 cycles each of which consisted of an annealing reaction at 60° C. for 1 minute and an elongation reaction at 72° C. for 20 seconds. "LIGHTCYCLER SYSTEM" was used for the detection of fluorescence. Upon conducting the detection, F1 (530 nm) and F3 (710 nm) which the system was equipped with were used for the detection of FITC and CY5, respectively. Further, the excitation intensity was fixed at 75%.
 As a result, in the case of the C-allele homozygote, the fluorescence intensity changed only when Primer 12 the 3' end of which was C-allelic was added. Specifically, the intensity of fluorescence from FITC decreased, while the intensity of fluorescence from CY5 increased. In the case of the T-allele homozygote, only when Primer 13 the 3' end of which was T-allelic was added, the intensity of fluorescence changed. In the case of the heterozygote, on the other hand, a change in fluorescence intensity was observed no matter which one of Primer 12 and Primer 13 was added. It has, therefore, been demonstrated that the detection of a single-base polymorphism is feasible even when a product amplified by the LAMP method is used as a template.

Example 10

Analysis of a Single-base Polymorphism by an Allele-specific Elongation Reaction Making use of a Reverse Transcriptase Single-base polymorphisms of LCHAD (long-chain 3-hydroxyacyl coenzyme A dehydrogenase) and OAT (organic anion transporter) were analyzed by a sequence-specific elongation method making use of a reverse transcriptase.

(1) Synthesis of a Template RNA

An RNA for use as a template in this example was prepared as will be described below.

Using the primers of the below-descried SEQ ID NOS: 17, 18, 21 and 22, duplex PCR was performed. One of the primers in each pair was provided with the 5'RNA polymerase promoter sequence. As reaction conditions for the multiplex PCR, AMPLITAQGOLD 1U (200 nM), primer pairs (50 ng), human genome DNA, AMPLITAQGOLD (200 μM) and dNTPs were combined into a homogeneous mixture, and the final volume was adjusted to 20 μL. The resulting reaction solution was thermally denatured at 95° C. for 10 minutes, and was then subjected to PCR 40 cycles each of which consisted of a denaturation reaction at 95° C. for 30 seconds, an annealing reaction at 65° C. for 30 seconds and an elongation reaction at 72° C. for 30 seconds. Subsequently, a transcription reaction was conducted using a "T7 AMPLISCRIBE KIT" (Epicentre Technologies).

(3) Preparation of Microarrays

For microarrays, standard microscope glass slide were used. After the glass slides were activated at the surfaces thereof with isothiocyanate, NH$_2$-modified oligonucleotides (SQ ID NOS: 19, 20, 23, 24) were immobilized on the surfaces, respectively. Each oligonucleotide was dissolved with 400 mM sodium carbonate buffer (pH 9.0) such that its concentration was adjusted to 20 μM. The resulting oligonucleotide solutions were dropped onto their corresponding glass slides in the form of spots of 2 mm in diameter, exposed to vaporized ammonia, and then washed three times with distilled water.

(3) Sequence-Specific Elongation Method

The template RNA prepared as described above was dissolved in a mixture of 10 mM Tris-HCl (pH 7.4), 1 mM EDTA, 0.2 M NaCl and 0.1% Triton X-100, and the resulting solution was added in an amount of 10 μL per spot to the arrays. The arrays were then incubated at 37° C. for 20 minutes to effect annealing. After the arrays were washed with 0.1 M NaCl, a reverse transcriptase "MMLV" (Epicenter Technologies) (6 U), dNTPs (dATP, dGTP, FITC-dUTP, CY5-dCTP) (6 μM) and a buffer furnished together with those enzymes were added, followed by a reaction at 52° C. for 1 hour.

(4) Detection of Signals

Using a "CONFOCAL SCAN ARRAY 400" (GSI Lumonics), the microscope glass slides were scanned at 480 nm excitation wavelength and 650 nm fluorescence wavelength. Values obtained by subtracting background fluorescence intensities were used for the determination of genotypes.

The slide with Primer 19, a primer specific to the C-allele of LCHAD, immobilized thereon showed a high signal intensity of about 900 only when the template containing the C-allele zygote of LCHAD was added as spots, and signals were all 100 or lower when the template free of the C-allele zygote was added as spots. The slide with Primer 20, a primer specific to the G-allele of LCHAD, immobilized thereon showed a high signal intensity (at around 800) only when the template containing the G-allele zygote of LCHAD was added as spots, and signals were all 100 or lower when the template free of the G-allele zygote was added as spots. The slide with Primer 23, a primer specific to the C-allele of OAT, immobilized thereon showed a high signal intensity of about 1200 only when the template containing the C-allele zygote of OAT was added as spots, and signals were all 100 or lower when the template free of the C-allele zygote was added as spots. As appreciated from the foregoing, it has been demonstrated that the nucleic acid assay method of the present invention permits an analysis of a single-base polymorphism by using a reverse transcriptase.

Example 11

Using fluorescein chlorotriazinyl-4-dC(deoxycytidine) nucleotide monomer, a nucleic acid was detected based on the quenching phenomenon by guanidine.

1) Template DNA and primer
   Primer 1 and Template 12 were used.
   Model 1: A combination of Primer 1 and Template 12.
   Model 2: A combination of Primer 1 and Template 12, without addition of VENT(EXO)DNA POLYMERASE.

2) Amplification reaction conditions
   A reaction solution was prepared as will be described below.
   20 mM Tris-HCl (pH 8.8); 10 mM KCl; 10 mM (NH$_4$)$_2$SO$_4$; 2.5 mM MgSO$_4$; 0.5% Triton X-100; 5% DMSO; 0.25 mg/mL BSA; 200 nM fluorescein chlorotriazinyl-4-dC; 200 nM dGTP; 200 nM dATP; 200 nM dUTP; 2 nM primer; 50 nM synthesized, single-stranded DNA; 0.1 VENT(EXO)DNA POLYMERFASE.

The final volume of the reaction solution was 20 μL. The above reactant solutions were combined into a homogeneous mixture. The reaction solution was thermally denatured at 95° C. for 15 seconds, and was then incubated 65° C. for 15 minutes. "LIGHTCYCLER SYSTEM" was used for the detection of fluorescence. F1 was used for the detection of fluorescence, and the excitation intensity was fixed at 75%.

As a result, in Model 1, the intensity of fluorescence at F1 decreased 24% at the maximum. In the reaction of Model 2 in which no enzyme was added, no change was observed in the intensity of fluorescence. From the above results, it is considered that the intensity of fluorescence decreased as a result of an interaction between the dc-FITC-labeled nucleotide, which had been incorporated into the strands under synthesis by the DNA polymerase, and guanine existing in the complementary chain.

[Base sequences of primers]
Primer 4: gtgtaaccca taaccccaa ga (SEQ ID NO: 15)
Primer 5: caccagcaga ccctcaagc (SEQ ID NO: 16)
Primer 6: cccacactca cagttttcac ttc (SEQ ID NO: 17)
Primer 7: cccacactca cagttttcac ttt (SEQ ID NO: 18)

Primer 8: tgttcctgat gcagtgggca gctttagtct gcggcggtgt tctg (SEQ ID NO: 19)

Primer 9: tgctgggtcg gcacagcctg aagctgacct gaaatacctg gcctg (SEQ ID NO: 20)

Primer 10: tgcttgtggc ctctcgtg (SEQ ID NO: 21)

Primer 11: ggggtggga agctgtg (SEQ ID NO: 22)

Primer 12: tgatcttgct gggtcggcac agc (SEQ ID NO: 23)

Primer 13: tgatcttgct gggtcggcac agt (SEQ ID NO: 24)

Primer 14: acctgatttc cttactgcct cttgc (SEQ ID NO: 25)

Primer 15: gtcctgcttg cttacctcgc ttagt (SEQ ID NO: 26)

Primer 16: tgtgcctgtc ctgggagaga c (SEQ ID NO: 27)

Primer 17: ttctaatacg actcactata gggagaccct tgccaggtga ttggc (SEQ ID NO: 28)

Primer 18: gcggtcccaa aagggtcagt gtttctgtgg tcacgaagtc (SEQ ID NO: 29)

Primer 19: ctctaatagt gctggctc (SEQ ID NO: 30)

Primer 20: ctctaatagt gctggctc (SEQ ID NO: 31)

Primer 21: ttctaatacg actcactata gggagacctt tgtagctggg aacttc (SEQ ID NO: 32)

Primer 22: gcggtcccaa aagggtcagt accaaaacct ggtaaatacg g (SEQ ID NO: 33)

Primer 23: gagatagcag acaacgtcc (SEQ ID NO: 34)

Primer 24: gagatagcag acaacgtcg (SEQ ID NO: 35)

Template 12: ttgttttgtt ttgttttgtt ttgttttgtt ttgttttgtt ttgttttgtt ttgttttgtt ttgttttgtt cgggtctaca ctgtcgagtc tg (SEQ ID NO: 36).

INDUSTRIAL APPLICABILITY

Without needing such a nucleic acid probe for a homogeneous solution system that changes in fluorescence intensity upon hybridization, a simple, easy, fast, low-cost, high-sensitivity assay method of a nucleic acid is realized by monitoring a change in the intensity of fluorescence from a nucleic acid polymerization system upon conducting a nucleic acid polymerization reaction to incorporate a labeled nucleotide in a nucleic acid polymer. This method has made it possible to assay all nucleic acids such as genes existing in a single system in the nature.

---

The invention claimed is:

1. A method of quantifying at least one nucleic acid, which comprises:
   conducting a nucleic acid polymerization reaction in a nucleic acid polymerization reaction system that is a reaction solution comprising:
   (A) said at least one nucleic acid as a template,
   (B)(a) a fluorescent dye capable of emitting fluorescence upon binding to a nucleic acid; and (b) a nucleotide monomer labeled with an acceptor fluorescent dye, and
   (C) at least one nucleic acid-synthesizing enzyme,
   measuring in real-time during the nucleic acid polymerization a change or an amount of a change in an optical character of said nucleic acid polymerization system as the reaction solution; and
   determining the quantity of said template nucleic acid or nucleic acid, being synthesized using said template nucleic acid as a template based on the measured change or the measured amount of the change in the optical character.

2. The method according to claim 1, wherein said nucleic acid polymerization system further comprises (D) a nucleic acid primer capable of specifically hybridizing to said template nucleic acid.

3. The method according to claim 2, wherein said nucleic acid primer (D) is a single unlabeled nucleic acid primer, which is selected from the group consisting of a forward primer, a reverse primer, and a primer that is both a forward and reverse primer.

4. The method according to claim 1, wherein said fluorescent dye (B)(a) is an intercalator.

5. The method according to claim 1, wherein said optical character comprises an optical character derived from said fluorescent dye (B)(a) and said acceptor fluorescent dye, with which said nucleotide monomer (B)(b) is labeled.

6. The method according to claim 1, wherein said nucleotide monomer (B)(b) comprises at least two kinds of nucleotide monomers which differ in base from each other, wherein said two kinds of nucleotide monomers are labeled with different acceptor fluorescent dyes, respectively, wherein said optical character is derived from said acceptor fluorescent dyes.

7. A method of detecting a single nucleotide polymorphism in a nucleic acid template, the method comprising:
   conducting a single-base elongation reaction in a nucleic acid polymerization reaction system that is a reaction solution, wherein the system comprises
   (A) the nucleic acid as a template,
   (B) (a) a fluorescent dye capable of emitting fluorescence upon binding to a nucleic acid; and (b) a dideoxynucleotide monomer labeled with an acceptor fluorescent dye,
   (C) at least one nucleic acid-synthesizing enzyme, and
   (D) a nucleic acid primer,
   measuring in real-time during the single-base elongation reaction a change or an amount of change in an optical character of the nucleic acid polymerization reaction system as the reaction solution; and
   detecting the single nucleotide polymorphism based on the measured change or the measured amount of the change in the optical character.

8. The method according to claim 7, wherein said nucleic acid primer (D) is designed such that the 3' end of the primer is complementary to a single nucleotide polymorphism site of the nucleic acid template.

9. The method according to claim 7, wherein said nucleic acid primer (D) is a single unlabeled nucleic acid primer, which is selected from the group consisting of a forward primer, a reverse primer, and a primer that is both a forward and reverse primer.

10. The method according to claim 7, wherein said fluorescent dye (B)(a) is an intercalator.

11. The method according to claim 7, wherein said optical character comprises an optical character derived from said fluorescent dye (B)(a) and said acceptor fluorescent dye, with which said dideoxynucleotide monomer (B)(b) is labeled.

12. The method according to claim 7, wherein said dideoxynucleotide monomer (B)(b) comprises at least two kinds of dideoxynucleotide monomers which differ in base from each other, wherein said two kinds of dideoxynucleotide monomers are labeled with different acceptor fluorescent dyes, respectively, wherein said optical character is derived from said acceptor fluorescent dyes.

* * * * *